US 10,945,634 B2

(12) United States Patent
Kusumoto

(10) Patent No.: US 10,945,634 B2
(45) Date of Patent: *Mar. 16, 2021

(54) MODULAR ELECTROPHYSIOLOGY MAPPING SYSTEM AND METHOD

(71) Applicant: Walter Kusumoto, Chico, CA (US)

(72) Inventor: Walter Kusumoto, Chico, CA (US)

(*) Notice: Subject to any disclaimer, the term of this patent is extended or adjusted under 35 U.S.C. 154(b) by 411 days.

This patent is subject to a terminal disclaimer.

(21) Appl. No.: 15/851,415

(22) Filed: Dec. 21, 2017

(65) Prior Publication Data

US 2018/0132754 A1    May 17, 2018

Related U.S. Application Data

(63) Continuation-in-part of application No. 15/819,745, filed on Nov. 21, 2017, and a continuation-in-part of application No. 15/713,307, filed on Sep. 22, 2017.

(60) Provisional application No. 62/516,556, filed on Jun. 7, 2017, provisional application No. 62/453,854, filed on Feb. 2, 2017, provisional application No. 62/437,847, filed on Dec. 22, 2016, provisional application No. 62/424,863, filed on Nov. 21, 2016, (Continued)

(51) Int. Cl.
| | |
|---|---|
| *A61B 5/06* | (2006.01) |
| *A61B 5/042* | (2006.01) |
| *A61B 5/00* | (2006.01) |
| *A61M 25/10* | (2013.01) |

(52) U.S. Cl.
CPC ............ *A61B 5/065* (2013.01); *A61B 5/0422* (2013.01); *A61B 5/062* (2013.01); *A61B 5/063* (2013.01); *A61B 5/6848* (2013.01); *A61B 5/6851* (2013.01); *A61B 5/6852* (2013.01); *A61B 5/7445* (2013.01); *A61B 2562/0223* (2013.01); *A61B 2562/0257* (2013.01); *A61M 25/104* (2013.01)

(58) Field of Classification Search
CPC .............................. A61B 5/065; A61B 5/0422
See application file for complete search history.

(56) References Cited

U.S. PATENT DOCUMENTS

| | | | | |
|---|---|---|---|---|
| 2002/0198521 A1* | 12/2002 | Maguire | ................. | A61N 7/02 606/41 |
| 2012/0130230 A1 | 5/2012 | Eichler | | |

(Continued)

*Primary Examiner* — Alyssa M Alter
(74) *Attorney, Agent, or Firm* — Heisler & Associates

(57) ABSTRACT

An electrophysiology mapping system is provided with modules which can be attached thereto, each module including an item of subcutaneous interventional equipment and information about the item of subcutaneous interventional equipment, including shape information and size information. At least one sensor is placed upon the item of subcutaneous interventional equipment at a known location thereon. This sensor allows for position, and also preferably orientation, of the item within an image presented on a display of the electrophysiology mapping system. The at least one sensor can be at least one electrode or two or more electrodes, with different known positions for the electrode, or electrodes. The at least one sensor can be one or more magnetic field sensors interacting with a magnetic field associated with the electrophysiology mapping system. Transthoracic ultrasound fitted with sensors thereon can also be utilized as a further module attachable to the electrophysiology mapping system.

14 Claims, 21 Drawing Sheets

Related U.S. Application Data provisional application No. 62/398,394, filed on Sep. 22, 2016.

(56) References Cited

U.S. PATENT DOCUMENTS

| | | |
|---|---|---|
| 2013/0190747 A1* | 7/2013 | Koblish ............. A61B 18/1492 606/33 |
| 2013/0296691 A1 | 11/2013 | Ashe |
| 2014/0243640 A1 | 8/2014 | O'Dea |
| 2015/0011995 A1 | 1/2015 | Avitall et al. |
| 2015/0208948 A1* | 7/2015 | Wei ........................ A61B 5/066 600/424 |

* cited by examiner

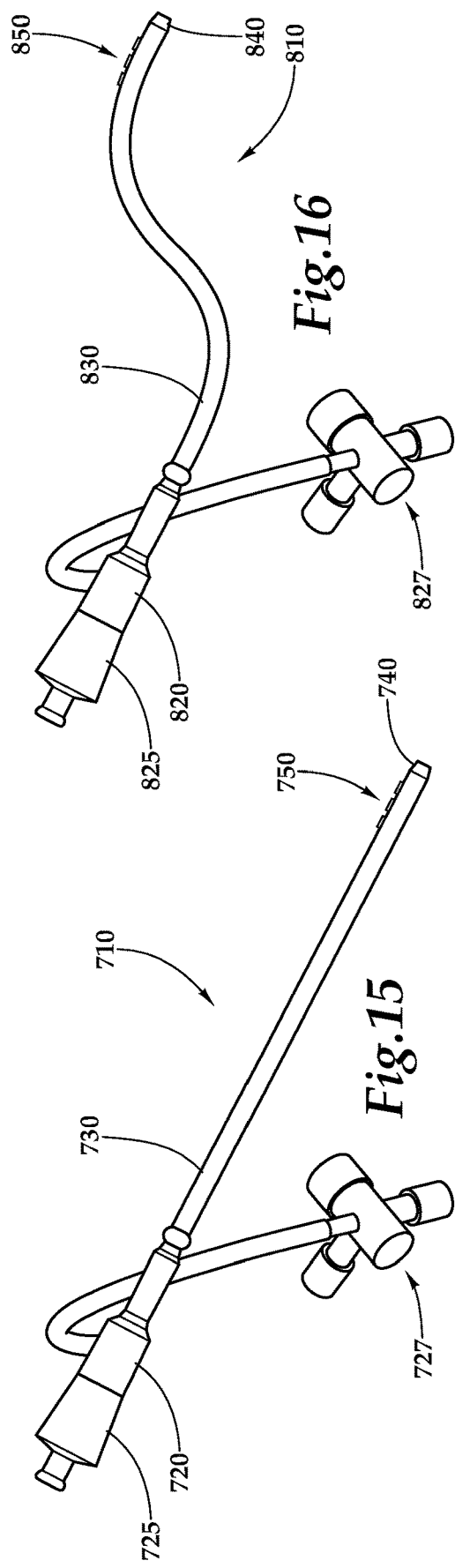
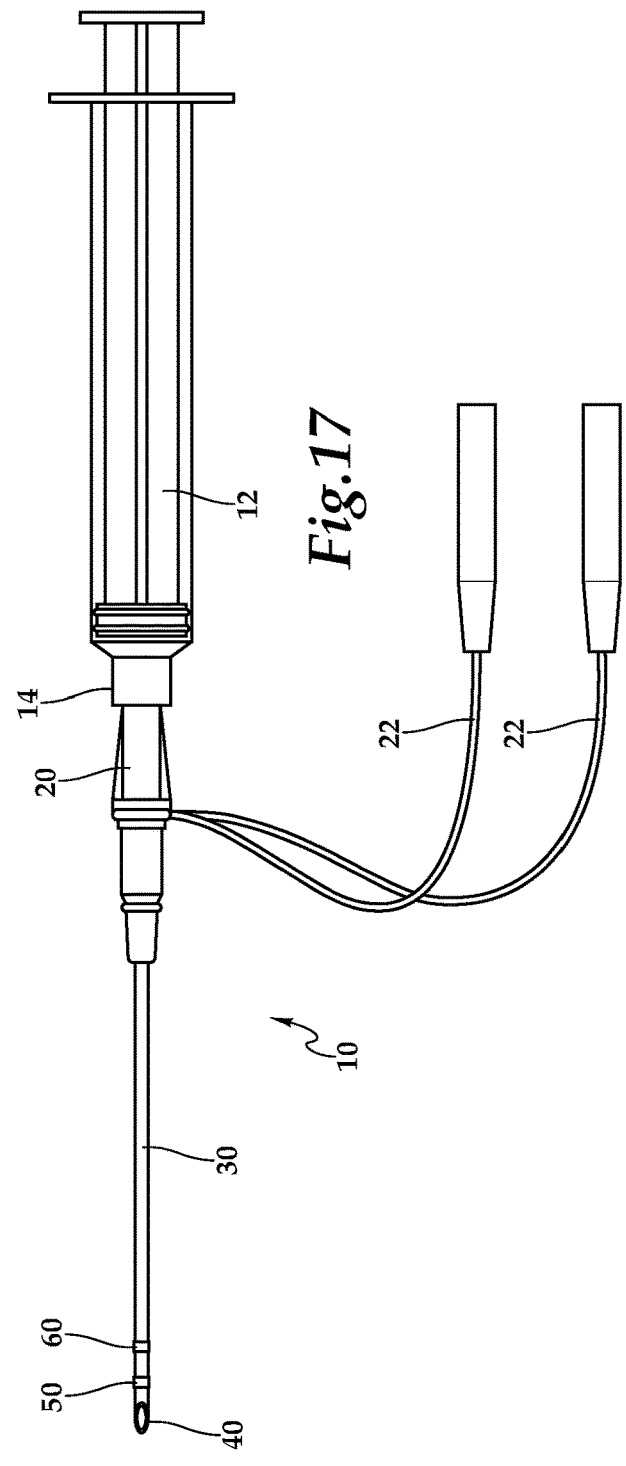
Fig.15
Fig.16
Fig.17

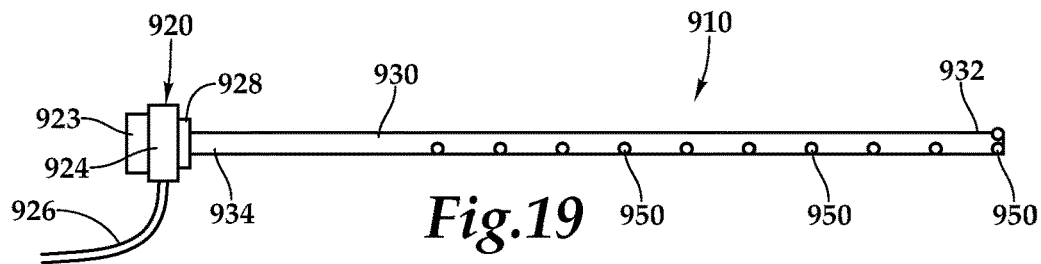
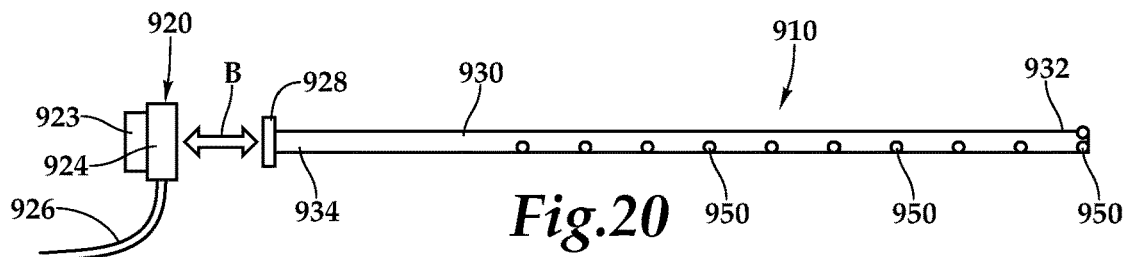
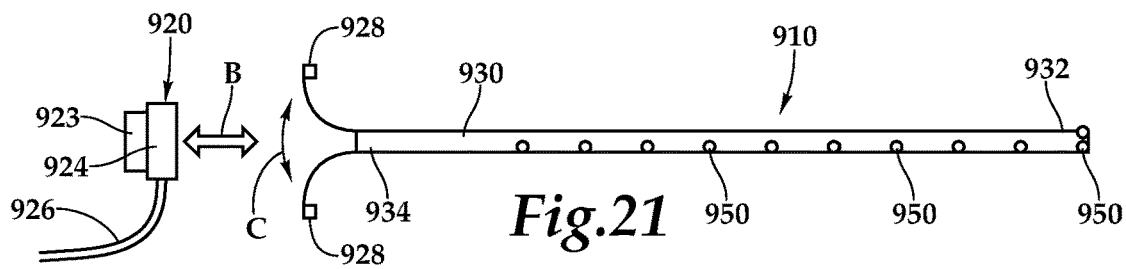
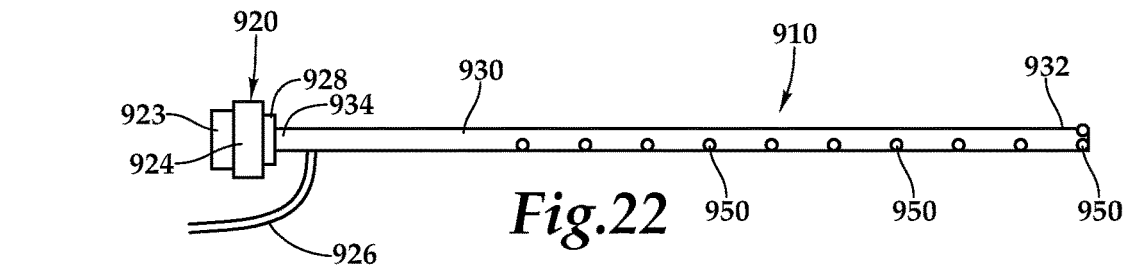
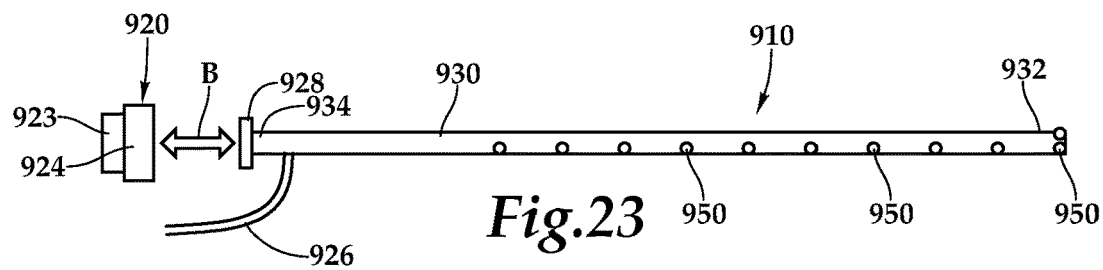
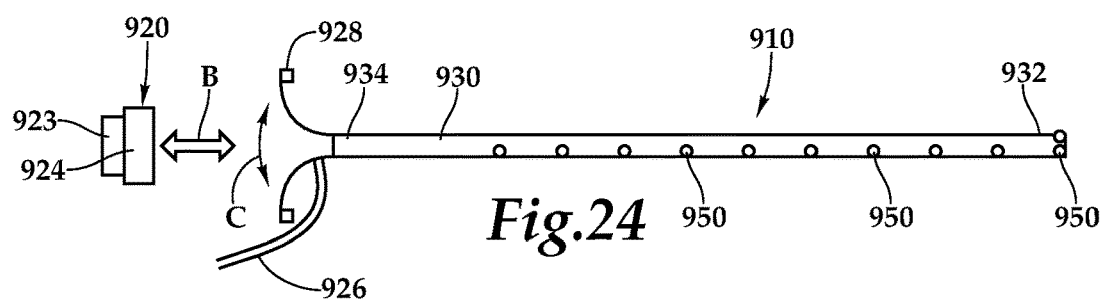

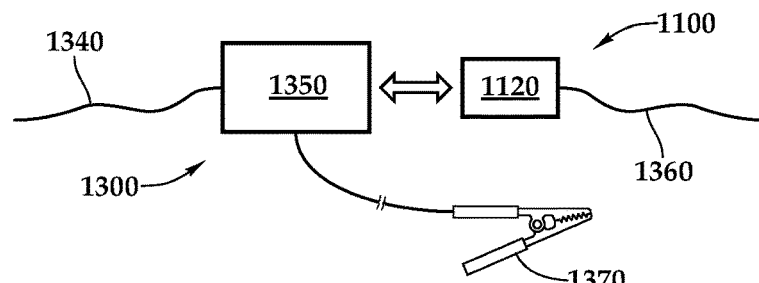
Fig.40
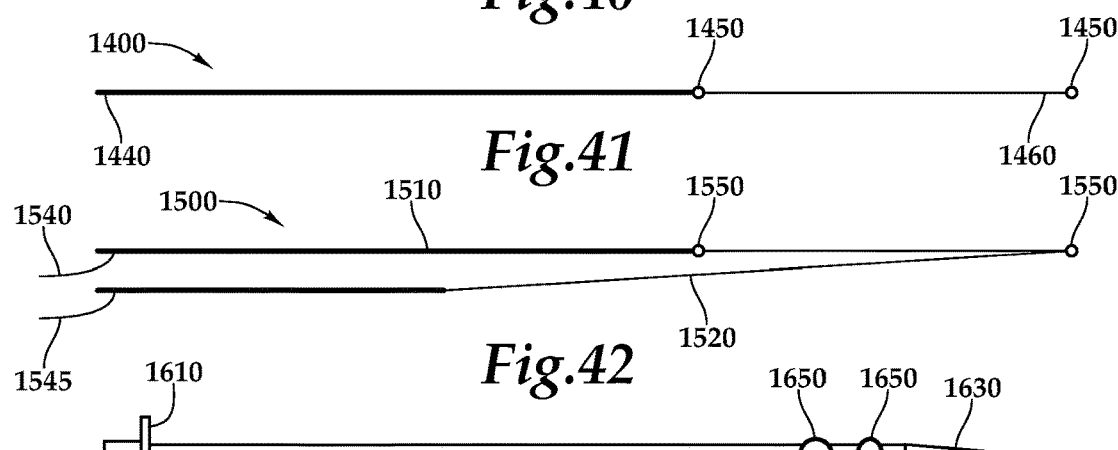
Fig.41
Fig.42
Fig.43
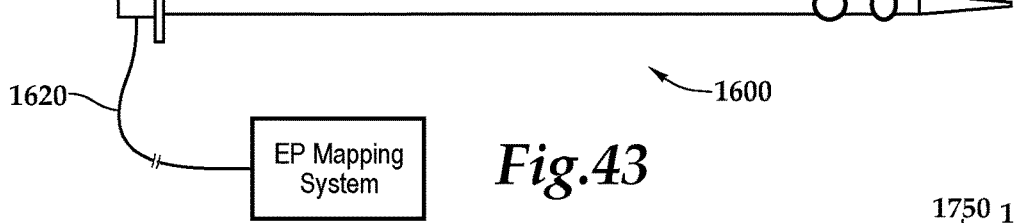
Fig.44
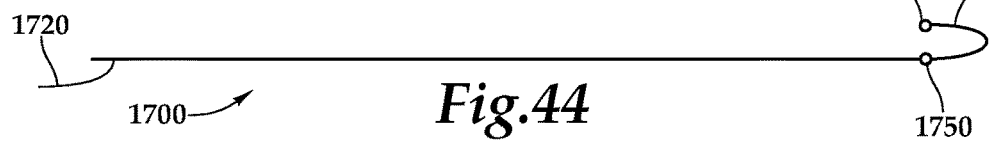
Fig.45
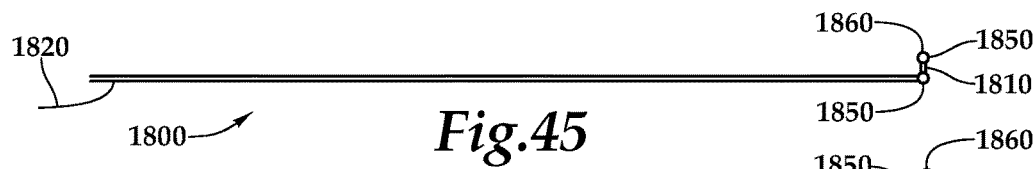
Fig.46
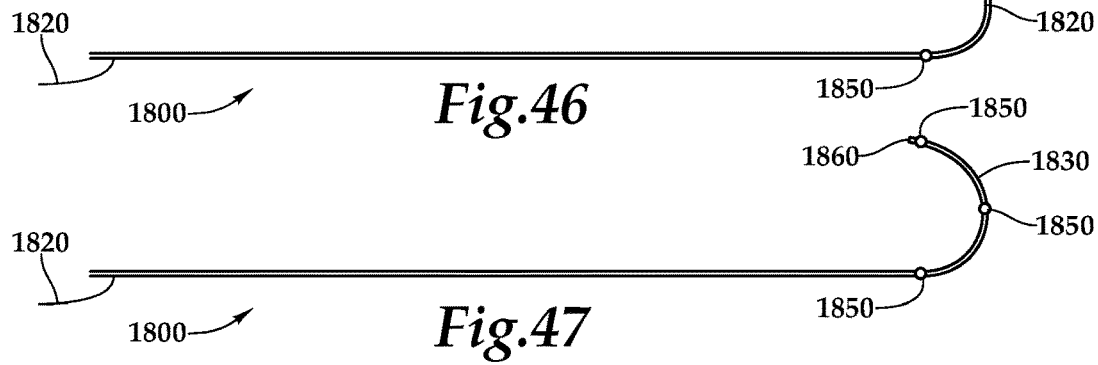
Fig.47

MODULAR ELECTROPHYSIOLOGY MAPPING SYSTEM AND METHOD

CROSS-REFERENCE TO RELATED APPLICATIONS

This application claims benefit under Title 35, United States Code § 119(e) of U.S. Provisional Application No. 62/437,847 filed on Dec. 22, 2016. This application is also a continuation-in-part of U.S. patent application Ser. No. 15/819,745 filed on Nov. 21, 2017 which claims benefit under Title 35, United States Code § 119(e) of U.S. Provisional Application No. 62/424,863 filed on Nov. 21, 2016 and U.S. Provisional Application No. 62/453,854 filed on Feb. 2, 2017. This application is also a continuation-in-part of U.S. patent application Ser. No. 15/713,307 filed on Sep. 22, 2017 which claims benefit under Title 35, United States Code § 119(e) of U.S. Provisional Application No. 62/398,394 filed on Sep. 22, 2016 and U.S. Provisional Application No. 62/516,556 filed on Jun. 7, 2017.

FIELD OF THE INVENTION

The following invention relates to visualization of subcutaneous interventional equipment, especially around a patient's heart, utilizing electrophysiology (EP) mapping systems. More particularly, this invention relates to percutaneous needles and other subcutaneous interventional equipment which is provided with sensors to allow for visualization of such subcutaneous interventional equipment on a display of an EP mapping system with an accurate location and orientation thereon, and with the equipment provided in modules which can be readily coupled to an EP mapping system and recognized by the EP mapping system for proper display of the equipment within the image presented on the display of the EP mapping system.

BACKGROUND OF THE INVENTION

Pacemaker and implantable cardiac defibrillators have a central role in arrhythmia management worldwide. In 2009, over a million new implants occurred in the United States alone. Fluoroscopy is traditionally the accepted method of visualization of the leads for placement within the heart. However this exposes the patient, operator and staff members to radiation. Certain patient populations may be more vulnerable to radiation, such as pregnant patients or pediatric patients.

Radiation exposure during implantation is significant. The reference radiation dose in the placement of pacemakers and implantable cardiac defibrillators (ICDs) to the operator are 4 mSv (1.4-17 mSv). For cardiac resynchronization therapy (CRT) usually utilizing the coronary sinus, the radiation dose is 22 mSv (2.2-95). Doses of 10-100 milliSievert (mSv) correspond to a definite increase in life time risk of fatal and nonfatal cancers. For 10 mSv the risk is $\frac{1}{1000}$ and for 100 mSv the risk increases to $\frac{1}{100}$. Equally important to patient safety is operator and staff safety, and reducing radiation exposure is an important objective.

Cardiac electrophysiology (EP) mapping systems use intracardiac magnetic sensors and electrodes to localize the position of the heart. The Biosense Webster Carto 3, provided by Biosense Webster, Inc. of Diamond Bar, Calif., uses magnetic sensors within a magnetic field for positional information of catheters within the heart. This system also uses a background electric field utilizing current to localize electrodes on non-magnetic sensor EP catheters.

The EN SITE system provided by St. Jude Medical, Atrial Fibrillation Division, Inc. of St. Paul, Minn., uses impedance to localize various catheters relative to a stable catheter located within the heart. There is a background circuit utilizing a high frequency transthoracic electric field between the catheters and body surface electrodes, which detect impedance changes relative to a stable cardiac catheter (usually located within the coronary sinus) to derive location information within the heart. At the time of writing, St. Jude had developed a system that also employed a magnetic field, and was currently under FDA review.

Pacemakers and implantable cardiac defibrillators are a central pillar for arrhythmia management. Fluoroscopy is the primary method of visualizing placement of traditional intracardiac leads, and for emerging technologies such as leadless pacemaker systems. However, fluoroscopy exposes the patient, operator and staff members to significant radiation which can increase the risk of various health problems such as malignancy. Radiation exposure for placement of pacemakers, defibrillators and especially cardiac resynchronization therapy can be significant.

Many pacemaker, ICD and CRT implantation procedures occurs in the cardiac electrophysiology suite, where the cardiac EP mapping sits dormant. Thus, a need exists to use EP mapping systems to allow lead placement procedures to be performed in a highly reliable fashion with imaging guidance from the EP mapping system without exposure to radiation. Since the number of patients requiring this therapy is large, there is potential for broad applicability, and possibly cost savings as the patient volume can be leveraged to reduce the per unit cost of the proposed technology.

A complication of pacemakers/ICDs/CRT and leadless pacemakers is pericardial effusion and pericardial tamponade. A magnetic sensor or electrode mounted pericardiocentesis needle in conjunction with a cardiac EP mapping system to directly visualize entrance into the pericardial space can be readily available to avert catastrophe. Permanent pacemaker/implantable cardiac defibrillators, cardiac resynchronization therapy and leadless pacemakers in conjunction with a cardiac electrophysiology mapping has the potential of reducing radiation exposure and increasing the precision of placement location of these permanent electrodes to increase safety for the patient, operator, and staff. This technology has broad applicability and the potential for wide spread adoption since the visual interface will be similar to current practices for operators.

Cardiac electrophysiology (EP) mapping systems have traditionally been for arrhythmia management exclusively. Such EP mapping systems have the potential to display more than just patient anatomical structures, and particularly cardiac structures, including visualization of subcutaneous interventional equipment, such as pericardiocentesis needles, sheaths, guide wires (such as J-wires) and other interventional equipment. By expanding EP mapping systems to be useful in visualizing subcutaneous interventional equipment, a variety of interventional procedures can be performed without requiring exposure to radiation for the patient and medical professionals, and to allow for visualization without requiring complex preparation steps, such as placement of intra-cardiac electrodes, in at least some instances.

SUMMARY OF THE INVENTION

With this invention, an interventional device is fitted with at least one, and preferably with a pair of electrodes utilizing impedance and/or electrical current data, or a magnetic sensor within a magnetic field to localize the device. In a first embodiment, the interventional device is depicted as a pericardiocentesis needle so that the needle tip can be visualized during pericardiocentesis or related procedures. This magnetic sensor or electrode in conjunction with existing cardiac electrophysiology mapping systems allows for direct/real time visualization of the entrance of the needle tip and dilator tip into the pericardial space. In addition, the cardiac electrophysiology mapping system can combine fluoroscopy, computer tomographic imaging and/or intravascular echo to further delineate epicardial/pericardial space and extracardiac structures during pericardiocentesis.

Electrophysiology mapping (hereafter EP mapping) systems are provided from multiple sources, and generally allow for an intra-vascular/intra-cardio catheter and/or electrode to have its location visualized within the heart. With this invention, a pericardiocentesis needle is outfitted in one of a variety of different manners, at least some of which are similar to the outfitting of catheters and/or electrodes within an EP mapping system which are placed intra-vascularly into or proximate to the interior of the heart. The pericardiocentesis needle is thus modified from prior pericardiocentesis needles to include at least one electrode thereon or some other sensor, such as a magnetic field sensor. This sensor, such as an electrode, is routed into the EP mapping system, such as in the same way that other electrodes or other sensors within an EP mapping system are integrated into the EP mapping system, such as the way that catheters and intra-venus electrodes of EP mapping systems are connected into such EP mapping systems for visualization thereof on a display of the the EP mapping system. One such EP mapping system is disclosed in U.S. Pat. No. 8,825,144, incorporated herein by reference in its entirety.

The methodology implemented by this mapping system is based on the principle that when electrical current is applied across two surface electrodes, a voltage gradient is created along the axis between the electrodes. Although any suitable number of electrodes may be utilized, typically six surface electrodes are placed on the body of the patient and in three pairs: anterior to posterior, left to right lateral, and superior (neck) to inferior (left leg). The three electrode pairs form three orthogonal axes (X-Y-Z), with the patient's heart being at least generally at the center.

These six surface electrodes are connected to the EP mapping system. In embodiments, such as those working with the St. Jude ENSITE EP mapping system, the various electrodes alternately send an electrical signal through each pair of surface electrodes to create a voltage gradient along each of the three axes, forming a transthoracic electrical field. Conventional electrophysiology catheters may be connected to the system and advanced to the patient's heart. As a catheter enters the transthoracic field, each catheter electrode senses voltage, timed to the creation of the gradient along each axis. Using the sensed voltages compared to the voltage gradient on all three axes, the three-dimensional position of each catheter electrode is calculated. The calculated position for the various electrodes can occur simultaneously and be repeated many times per second.

The EP mapping system can display the located electrodes as catheter bodies with real-time navigation. By tracking the position of the various catheters, the system provides non-fluoroscopic navigation, mapping, and creation of chamber models that are highly detailed and that have very accurate geometries. In the latter regard, the physician sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired.

In order to generate an accurate and highly detailed map of a patient's heart, a large amount of data is required. Accordingly, an electrode catheter may be swept across various surfaces of the heart while obtaining data as described above. In order to accelerate this mapping data acquisition and/or increase the volume of data available for mapping, a number of high-density electrode catheters have been developed or proposed. Generally, these include a number of electrodes in an array in relation to a catheter body so as to substantially simultaneously obtain many mapping data points for a corresponding surface of cardiac tissue proximate to the catheter body. For example, these electrodes may be deployed along the length of a section of the catheter body that has a coil or other three-dimensional configuration so as to provide the desired spatial distribution of the electrodes. Alternatively, the electrodes may be disposed on a number of structural elements extending from a catheter body, e.g., in the form of a basket or a number of fingers.

Once the mapping data has been acquired, software may be implemented to generate multiple surface images, which when combined, comprise a three-dimensional image of the patient's heart. This image can be displayed on a suitable output device in real-time so that the physician can "see" the patient's heart and the catheter for properly positioning the catheter at a work site within the patient's heart for a medical procedure (e.g., an ablation procedure).

The electrode or other sensor on the needle causes the location of the electrode relative to adjacent cardiac structures to be visualized on the display of the EP mapping system. By placing the electrode on the needle a known distance from a tip of the needle, and by knowing the orientation of the needle, the precise location of the tip of the needle can be known and visualized on the EP mapping system display. Knowing orientation of the needle can occur by having multiple electrodes on the needle, one distal and one proximal, so that the orientation of the needle is merely a line segment between the position of the two electrodes, or can be ascertained in some other fashion, such as by having a needle orientation sensor placed on the needle itself or other sensor physically attached to the needle. In one embodiment one of the electrodes can be the tip of the needle itself. By visualizing on the display the location of the tip of the pericardiocentesis needle in real time, a surgeon or other medical professional can precisely place the tip of the pericardiocentesis needle where desired relative to adjacent cardiac structures.

In certain environments, other imaging systems can be incorporated along with the EP mapping system, such as CT scans, MRI scans, ultrasound, fluoroscopy, etc. While the invention is described above in particular with regard to pericardiocentesis needles, other interventional devices have a transcutaneous nature can similarly be outfitted with electrodes or other sensors and integrated into the EP mapping system for visualization of location (and preferably also orientation) of such other devices. Such other devices include dilators, sheaths, catheters, stylets associated with needles and dilators, and other transcutaneous interventional devices. When EP mapping systems are referenced, these can be electric field based or magnetic field based, as described above (or some combination thereof).

In addition to needles such as pericardiocentesis needles, other interventional devices, especially for cardiac lead placement procedures are proposed, utilizing cardiac electrophysiology (EP) mapping systems to minimize radiation exposure, in conjunction with the various cardiac interventional devices. Such devices include sheaths and other lead placement devices mounted with magnetic field sensors or electrode sensors, while also optionally utilizing the electrodes of the pacemaker or implantable cardiac defibrillator (ICD) leads. As described above with this invention, and in a prior invention by the inventor herein, magnetic sensors or electrode sensors mounted on pericardiocentesis needles are disclosed in pending U.S. patent application Ser. No. 15/713,307, filed on Sep. 22, 2017, incorporated herein by reference in its entirety, and also with associated disclosure and drawings thereof included herein for convenience.

Other interventional devices, such as J-wires (or other navigation/guide wires), dilators or sheaths, can be similarly fitted with sensors, such as magnetic field sensors or electrodes to assist with the placement of cardiac leads and allow visualization of these instruments in a cardiac EP mapping system. Cardiac resynchronization therapy (CRT) can use catheters and sub-vessel selecting catheters mounted with magnetic sensors or electrode sensors as well. Shapeable coronary sinus wires equipped with electrodes and possibly magnetic sensors can sub-select branches of the coronary sinus. Leadless pacemakers can also be placed using catheters mounted with electrodes or magnetic sensors according to this invention.

As an option, these leads can be placed with a fluoroscopic or chest X-ray back drop utilizing landmarks for alignment with a cardiac EP mapping system. This will allow for a familiar visual experience for the cardiac electrophysiologist or cardiologist. Additional modalities utilizing echocardiography and/or CT scans can also be visualized on the cardiac EP mapping system. The cardiac EP mapping system allows for the combining of all or some of these imaging modalities which potentially allow for more precision in localization of lead placement within the cardiac chambers.

An electrode mounted coronary sinus wire can be visualized on an impedance and/or current based cardiac EP system. Leadless pacemakers are an emerging technology, and the electrodes of the leadless system are visualized by a cardiac EP mapping system. With this invention, the catheters and systems that place these leadless pacemakers are mounted with magnetic sensors or electrodes to allow for visualization of the catheter or non-catheter system in a cardiac EP mapping system. Electrode mounted catheters or systems can utilize impedance or current to visualize the catheter, which is then separately visualized from the leadless pacemaker electrodes.

In one design according to this invention, a sheath is mounted with a magnetic sensor and multiple electrodes to allow for visualization of the sheath as a surrogate for markers for the pacemaker/ICD lead in the EP mapping system. The lead enters the fastener, passes through the sheath base, tear away base and sheath body, until the distal tip is at a fixed distance past the sheath tip. The fastener is locked down onto the lead. An example of a fastener can be a rotating mechanism to reduce the aperture around the lead. A sliding mechanism or a locking switch using a cam mechanism could also be used. The sheath body would be quite flexible, especially towards the tip. The flexibility would ideally be similar to the pacing/ICD lead, yet relatively strong longitudinally. There can be differential flexibility, where the sheath body towards the tear away base could be relatively stiffer compared to the distal end which would be quite flexible. A magnetic sensor (or electrode) could be at the tip, with electrodes (or magnetic field sensors) along the body of the sheath, which would allow visualization of the distal portion of the lead within the EP mapping system. One option is to provide ten electrodes, but any number of electrodes could be utilized. Also, multiple magnetic sensors along the sheath body could be utilized. The electrodes and/or magnetic sensors could also be distributed on both sides of the sheath.

The fastener would lock the lead in place. There could be a detection mechanism for the lead relative to the sheath, to warn the operator that the sheath and lead need to be resecured. In this design, the sheath base, and fastener with cable can be detached. Once the lead is in the desired location, and deployed, the fastener can be loosened, and the sheath base/faster can be removed from the body of the sheath. This can be a plug mechanism, twisting mechanism or switch with quick release or any combination thereof.

The tear away base of the sheath can be broken and the sheath body (i.e. the tube) can be removed. Electrodes and magnetic sensor(s) could be on a specific side of the sheath to allow for the sheath to be easily torn away. If necessary, a commercially available cutter tool could be used to secure the lead and cut away the sheath body. The sheath can be perforated, or have a rail system to tear away or guide the cutter through the sheath. Alternatively a long stylet could be within the lead, and the entire sheath mechanism is removed in a proximal direction, while forward pressure is placed on the long stylet. This latter option for removal, would likely be more awkward for the operator and less desirable.

In another design, the electrode or magnetic sensor mounted sheath prototype has ten electrodes on a tube portion thereof, and a stop cock is optional. The silicone tube could be engineered as thin as possible to have a close fit with the lead. The flexibility could be similar to the pacemaker lead, and could also have differential flexibility along the length of the sheath. For example, the distal portion could be quite flexible, while the proximal portion could be less flexible. A pacing lead is inserted into the sheath. The sheath would be thinner, and can have similar pliability to a pacing lead, or have variable flexibility along the length of the lead. A 10 pin cable provides connection to the cardiac EP mapping system. After placement, the fastener to the pacemaker lead is loosened and removed from the lead and electrode and/or magnetic sensor mounted sheath tube.

In another embodiment, the sheath is an exoskeleton of electrodes and/or magnetics sensors that fit around the lead. The electrodes or magnetic sensors can fit on the spine or along the secondary attachments or splines which would fit around the lead. Once the lead is in place, the exoskeleton of electrodes and/or magnetic sensors can be removed from the patient. The secondary attachments or splines can be flexible and when removed to run parallel with the primary spine, thus potentially decreasing the diameter needed to place the lead. In this design, the electrodes or magnetic sensors could spiral around the cardiac pacing or implantable cardiac defibrillator lead.

Optionally, a secondary spine can be attached to the secondary attachments or splines which connect the pacemaker lead to the primary spine. The secondary spine is pushed/pulled to disattach the exoskeleton from the lead. After placement of the lead where desired, the exoskeleton of leads/magnetics sensors is removed from the patient, leaving the lead in place. The secondary attachments or splines can be flexible to straighten on removal from the patient.

As another option, there would be extra secondary attachments or splines through the length of the exoskeleton. A secondary spine could also be added to this version. In this version the lead lock of the exoskeleton to the cardiac lead may be optional based on how efficient the secondary attachments or splines attach to the lead without movement between the cardiac lead and electrodes/and or magnetic sensors.

The electrodes or magnetic sensors could be located anywhere along the secondary attachments or splines, or both prongs of the secondary attachments or splines. A secondary spine can be provided for easy disattachment of the secondary attachments or spines from the pacemaker lead. As one option, ten electrodes and/or magnetic sensors are provided at common spacing away from a distal tip.

As another variation, the exoskeleton can fit around the pacing/ICD lead, and have mounted electrodes and/or magnetic sensors. The exoskeleton can be a series of small wires, that fit around the pacing lead or ICD lead.

As another variation, the electrodes or magnetic sensors are placed upon a jacket that has a slot opening down the jacket of one side. The pacing lead or ICD lead fits into the jacket through this slot and locked in place by the fastener. The lead can later be displaced out of this slot and out of the jacket for removal of the exoskeleton in this variation.

Other interventional devices used in lead placement according to this invention include stylets mounted with magnetic sensors, J-wires equipped with a magnetic sensor or electrode(s), coronary sinus wires equipped with magnetic sensors, sheaths, dilators and luminal catheters equipped with electrode(s) or magnetic sensors to deliver permanent pacemaker leads, implantable cardiac defibrillator leads, coronary sinus leads or leadless pacemaker systems into the heart, with visualization through a cardiac EP mapping system.

For instance, a stylet is equipped with magnetic sensor(s) which fit into a pacemaker or implantable cardiac defibrillator lead. Stylets will go through IS-1 or IS-4 ports through the body of the lead. The diameter of the lumen is typically set by industry standard between the different pacemaker/defibrillator companies. A magnetic sensor could be placed at the tip, and possibly another sensor or sensors (electrode or magnetic) within the body of the stylet. The tensile properties should be similar to current stylets, which are bendable, yet firm enough to hold a shape. The wires for the magnetic sensor could be braided together to increase the strength of the stylet. A very small amount of stiff insulation could also be used. Ideally no insulation with the exception of around the magnetic sensor could be used to maintain a similar tactile experience to the operator. Since multiple stylets may be used in a single implant, they should be relatively disposable Also provided in one form of this invention is an interface cable between the EP mapping system and the magnetic sensor mounted stylet/permanent pacemaker. The interface cable connects to the magnetic sensor stylet, and is easily attachable or detachable, so that other stylets can be utilized. This can be a male/female connection. The interface cable can have alligator clip(s) or other clip(s) to easily attach to the pacing electrodes on the permanent pacemaker/implantable cardiac defibrillator lead. The interface cable then connects to the EP mapping system. The interface cable could potentially be re-sterilized.

Another interventional device according to an embodiment of this invention is, a magnetic sensor or electrode mounted on a thin filament wire, composed of two wires which are relatively flexible and still hold a shape if bent by the operator, or can be pre-shaped to navigate branch vessels within the coronary sinus. Another magnetic sensor or electrode could be at the tip of the thicker wire body, and the wire body would go through the permanent pacemaker lead and back to the interface cable. This wire can be steered by the operator to a branch vessel of the coronary sinus. As a variation on such a navigation wire, a magnetic sensor(s) double wire can be provided for coronary sinus navigation. In such a design, a double wire is utilized. The main wire travels adjacent to the left ventricular lead while the secondary wire is within the lumen of the left ventricular lead. The main wire houses the magnetic (or electrode) sensors, while the secondary wire is very thin except at the opposite end which is stiffer to allow for back loading into the left ventricular lead. The entire double wire is then moved as a single unit to cannulate the desired coronary sinus branch. Once cannulated, the left ventricular lead is advanced over the secondary wire similar to a "buddy wire" technique. The thicker portion of the secondary wire is cut by the operator at the proximal end of the lead, and the main wire body is removed from the patient, along with the very thin secondary wire from the lumen of the left ventricular lead. This design allows for less space constraints for the magnetic sensor(s) or electrodes.

As another interventional device, a plastic dilator can be provided which has a wire which feeds to the distal tip electrode which is tapered, or can be located just proximal to the distal tip, so that a J-wire would not interfere with the electrical properties of the electrode. Rather than electrodes, magnetic sensors could be located near the tip, to convey location within the magnetic field, and to confirm the presence of the dilator within the vascular space.

As a further interventional device according to this invention, a J-wire mounted with magnetic sensors or electrode(s) is provided to allow for visualization of access within the intravascular space. In such a design, a J-wire is equipped with either a magnetic sensor or electrode to allow for visualization within the intravascular system on a cardiac EP mapping system. It is likely a magnetic based cardiac EP mapping system would utilize a magnetic sensor whereas an electrical impedance or current based system would utilize an electrode(s). The J-wire could have one or more electrodes or magnetic sensors thereon.

As a still further interventional device according to this invention, luminal catheters with magnetic sensors or electrodes can be visualized with the cardiac EP mapping system to visualize the tip of the catheter within a coronary space, such as the coronary sinus. Such luminal catheters are equipped with electrodes and/or magnetic sensors that can go through a sheath, and be visualized in a cardiac EP mapping system. The luminal catheters can have various shapes to sub-select a branch of the coronary sinus. These luminal catheters could accommodate a pacing lead and magnetic sensor mounted wire to be inserted into the selected branch of the coronary sinus. The catheter can be larger, to accommodate a "leadless" pacemaker so that this device could be delivered using a cardiac EP mapping system.

One aspect of this invention is using the cardiac EP mapping system for other cardiac and non-cardiac procedures. A needle is mounted with electrode(s) and/or a magnetic field sensor for vascular access visualization with a cardiac EP mapping system. This magnetic sensor and/or electrode(s) can work with a magnetic sensor/electrode mounted J-wire, magnetic sensor/electrode mounted dilator, magnetic sensor/electrode mounted sheath, or other subcutaneous interventional equipment. Preferably, such equipment is provided with an easy mounting connector to connect to the EP mapping system and is modular, including information correlating with each item of equipment, such as size, shape and sensor position so that the EP mapping system can accurately include a depiction of the item on the display of the EP mapping system.

Such expansion modules for cardiac EP mapping systems, which will include connectors and software modules to accommodate these new additions, can include transthoracic echo probe(s), magnetic (or electrode) sensor mounted stylets, electrode connections for permanent pacemaker and implantable cardiac defibrillator leads, electrode or magnetic sensor mounted coronary sinus or coronary artery interventional wires, and cardiac/cardiac electrophysiology/vascular catheters. Anatomical visualization of the coronary arteries can be added into the above modules to allow for position information of the coronary arteries within the cardiac electrophysiology mapping system. Such systems can include coronary angiogram catheters, coronary/peripheral artery/venous interventional wires, coronary/peripheral artery/venous interventional balloon, and coronary/peripheral artery/venous stent systems equipped with electrodes and/or magnetic sensors, to be used concomitantly with the above cardiac EP mapping system modules. This allows for these interventions to be performed with reduced radiation exposure to patients, operator, and staff. A limited cardiac EP mapping system can be provided, which is tailored for cardiologists, cardiac interventionists, and possibly other medical professionals requiring vascular/non vascular access. This allows for widespread usage of the system in standard cardiac catheterization labs, operating rooms, and radiological suites.

In one particular example, a percutaneous needle can be equipped with electrode(s) and/or magnetic sensor, or magnetic sensor alone, to allow visualization of the vascular space while entering utilizing an EP mapping system. As one option, bipolar electrodes are mounted on the needle shaft. Wires travel along the needle shaft around an insulated needle, and are also protected by outer insulation. The distal electrode could be near the tip, but not at the tip, and a known distance from the tip, to allow a computer to calculate the location of the tip (and accurately display its location in the EP mapping system) based on orientation of the electrodes. The inner electrode wires could be distributed advantageously.

As another option, the needle is equipped with a distal unipolar electrode. The opposite electrode could consist of a surface electrode or intracardiac electrode. This design would allow for a thinner shaft, however may not be able to provide needle orientation. It would typically be visualized as a single point on the EP mapping system entering into the pericardial space. The tip can be beveled, blunted, rounded or other shape at the tip.

As another option for such a percutaneous needle module, there is an insulated needle (plastic, ceramic, carbon fiber or other material), with an electrode stylet which inserts through the needle, and with a proximal electrode on the needle shaft. The tip of the needle can be beveled, blunted, rounded or other shape at the tip. Such a configuration essentially provides two electrodes, with only one mounted to the needle.

As another option, electrodes can be replaced (or supplemented) with magnetic field sensors. An one option three sensors give locational data in three axes in a magnetic field used by EP mapping systems. The magnetic sensors could be located proximal to the tip, to allow for a thinner needle at the body relative to the tip, a tapered design. The tip of the needle could be calibrated to the magnetic sensors, to derive the three-dimensional location of the tip of the needle. The magnetic sensors could also be located closer to the needle hub, or possibly housed in the hub, depending on the size of the magnetic field. The tip can be beveled, blunted, rounded or other shape at the tip. The needle can also be equipped with both magnetic sensors and electrodes, if required by the cardiac EP mapping system.

As an option, the magnetic sensors could also be located closer to the needle hub, or possibly housed in the hub, depending on the size of the magnetic field around the thorax. The magnetic sensors and the needle tip could be a calibrated to place the tip of the needle a known fixed distance from such hub sensors, to allow for a "naked" needle, as it enters the body to the pericardial space. The distance between the magnetic sensor and needle tip would be long enough to allow for a "naked" needle, but short enough to avoid problems associated with any bending of the needle, thus shortening the needle tip distance to the magnetic sensors. The tip can be beveled, blunted, rounded or other shape at the tip.

An easy connector plug for the magnetic sensor and/or electrode mounted needle, J-wire end, magnetic sensor and/or electrode mounted dilator and sheath (or other interventional equipment can be made to easily connect and disconnect to the EP mapping system. The easy connecting system could be interchangeable with the magnetic sensor and/or electrode mounted needles/dilator/sheaths. They could also connect to one connector in a piggyback manner.

In a further embodiment, a module can include a basic interface with the cardiac EP mapping system and the user, which allows a trained echo technician or hospital staff member to utilize the cardiac EP mapping system. A simpler interface would allow non cardiac electrophysiologists to interface with the system, such as interventional cardiologists and cardiologists. An ultrasound interface within the cardiac EP mapping system would allow for a more familiar experience for non cardiac electrophysiologists, and staff.

An advanced module can be provided to accommodate modules such as sensor mounted pericardial needle percutaneous vascular access needles, J-wires, dilators, sheaths, transthoracic echo probe(s), magnetic sensor mounted stylets, electrode connections for permanent pacemaker and implantable cardiac defibrillator leads, electrode or magnetic sensor mounted coronary sinus or coronary artery interventional wires, and cardiac/cardiac electrophysiology/vascular catheters, during the mapping study for cardiac electrophysiologists.

In a further embodiment, a limited version of a cardiac EP mapping system could be made, which would consist of a magnet, computer, input for the echo probe and basic catheters. This could be used to supplement standard cardiac catheterization equipment, and be used with magnetic sensor and/or electrode mounted needles/J-wires/dilators/sheaths, magnetic sensor mounted stylets, electrode mounted coronary sinus wires, and electrode/sensor mounted catheters. An operating room and radiology suite version can also be provided.

In a further embodiment, a module is provided for combining CT coronary angiography to a cardiac EP mapping system. Combining CT scans and MRI scans to cardiac EP mapping systems are currently available. However combining CT coronary angiography to cardiac electrophysiology mapping systems is not currently available. Gating can be employed to accommodate the cardiac cycle. Orientation can be done using anatomical landmarks such as heart valves, which can be combined with transthoracic echo, intravascular echo, and positional information of cardiac catheters. After the correct orientation is achieved, the rest of the cardiac CT can be subtracted from the coronary arteries, and a coronary artery shell can be combined with echo and cardiac EP mapping contours to delineate anatomical location of the coronary arteries in a relatively swift fashion within the map that is displayed by the EP mapping system.

In a further embodiment, coronary angiogram catheters, coronary/peripheral artery/venous interventional wires, coronary/peripheral artery/venous interventional balloons, and coronary/peripheral artery/venous stent systems equipped with electrodes and/or magnetic sensors are provided with sensors and modularized for interfacing with the EP mapping system. Magnetic sensors and/or electrodes can be mounted advantageously on various curved catheters, including and not limited to judkins, multipurpose, amplatz, internal mammary and graft catheters. As an option, a magnetic sensor or electrode is mounted on a thin filament wire, composed of one or more wires which is relatively flexible and still holds a shape if bent by the operator, or can be pre-shaped to navigate branch vessels within the coronary or peripheral arteries or veins. Another magnetic sensor or electrode could be at the tip of the thicker wire body, and the wire body would go through the permanent pacemaker lead and back to the interface cable. This wire can be steered by the operator to a branch vessel of the coronary/peripheral artery/vein. The coronary sinus wire would taper from a thicker body to a thinner tip. In one embodiment, the body would be about 0.38 mm and would taper to 0.25 mm at the tip. At this magnitude an electrode tip may be more feasible. The thin filament(s) would be coated with a polymer for insulation, and exposed portions, likely at the tip and possibly just proximal to the tip, would act as electrodes. When multiple electrodes are utilized, the filaments can be intertwined to varying degrees to maintain softness or add stiffness.

Another embodiment of this coronary artery/peripheral artery/venous wire would have insulation at the tip, to maintain the softness of the wire, while just proximal to the tip, the wire would be exposed to function as an electrode for visualization on the EP mapping system.

Interventional balloons (which travel over the electrode and or sensor mounted wire) can be equipped with electrode(s) and or magnetic sensors. This can be within the wire, and/or on the surface of the balloon. The coronary/peripheral artery/venous stent systems (which travel over the electrode and or sensor mounted wire) could also be equipped with electrode(s) and or magnetic sensors for visualization on the EP mapping system.

OBJECTS OF THE INVENTION

Accordingly, a primary object of the present invention is to provide a permanent cardiac pacing/implantable defibrillator/coronary sinus lead or leadless cardiac pacemaker lead utilizing a cardiac electrophysiology (EP) mapping system to reduce or eliminate fluoroscopy during implantation.

Another object of the present invention is to provide a pacing/implantable defibrillator/coronary sinus stylet equipped with a magnetic sensor(s) or electrode(s) on the tip and/or along the body to be visualized in a cardiac EP mapping system.

Another object of the present invention is to provide an interface wire between the stylet and the cardiac electrophysiology mapping system equipped with an additional electrical connector for the permanent pacemaker/defibrillator/coronary sinus lead proximal and distal electrodes.

Another object of the present invention is to provide a wire for navigation within the vascular tree and coronary sinus utilizing magnetic sensors or electrodes for a cardiac EP mapping system.

Another object of the present invention is to provide a dilator/sheath equipped with electrodes or magnetic sensor to deliver pacing/defibrillator leads which can be visualized in a cardiac EP mapping system.

Another object of the present invention is to provide a dilator/sheath/catheter equipped with electrodes or magnetic sensor to deliver a "leadless" pacemaker using a cardiac EP mapping system.

Another object of the present invention is to provide a J-wire mounted with a magnetic sensor or electrode to allow visualization in a cardiac EP mapping system.

Another object of the present invention is to provide an electrode mounted coronary sinus wire or cardiac interventional wire, dilator, sheath and coronary sinus catheter which can utilize either impedance or current to give locational information for the cardiac electrophysiology mapping system.

Another object of the present invention is to provide a percutaneous needle mounted with electrodes and/or magnetic sensors for vascular access for visualization on cardiac EP mapping systems and modules for expansion and limited versions of cardiac EP mapping system.

Another object of the present invention is to provide a percutaneous needle mounted with electrodes and/or magnetic sensors for vascular access to by visualized by a cardiac EP mapping system with an easy connection system.

Another object of the present invention is to provide an expansion module for cardiac EP mapping systems to visualize pericardial needles, percutaneous vascular access needle, J-wires, dilators, sheaths, transthoracic echo probe(s), magnetic sensor mounted stylets, electrode connections for permanent pacemaker and implantable cardiac defibrillator leads, electrode or magnetic sensor mounted coronary sinus or coronary artery interventional wires, and cardiac/cardiac electrophysiology/vascular catheters.

Another object of the present invention is to provide a limited cardiac EP mapping system tailored for general cardiologists/interventional cardiologists/and possibly other medical practitioners who require vascular access to accommodate pericardial needle percutaneous or vascular access needles, J-wires, dilators sheaths, transthoracic echo probe(s), magnetic sensor mounted stylets, electrode connections for permanent pacemaker and implantable cardiac defibrillator leads, electrode or magnetic sensor mounted coronary sinus or coronary artery/venous interventional wires, and cardiac/cardiac electrophysiology/vascular catheters.

Another object of the present invention is to provide a CT coronary angiography module for cardiac EP mapping systems.

Another object of the present invention is to provide coronary angiogram catheters equipped with electrodes and/or magnetic sensors.

Another object of the present invention is to provide coronary/peripheral artery/venous interventional wires, coronary/peripheral artery/venous interventional balloons, and coronary/peripheral artery/venous stent systems equipped with electrodes and/or magnetic sensors for visualization and use with EP mapping systems.

Another object of the present invention is to provide an EP mapping system which can have modules attached thereto associated with an item of subcutaneous interventional equipment so that sensors on the item can be accurately interpret for display of position, orientation, shape and size of the item accurately within an image visualized on the display of the EP mapping system.

Another object of the present invention is to provide modules which allow various items of subcutaneous interventional equipment to be guided by a medical professional viewing an EP mapping system coupled to the item of subcutaneous interventional equipment.

Another object of the present invention is to make EP mapping equipment usable by medical professionals in support of procedures other than arrhythmia mapping.

Other further objects of the present invention will become apparent from a careful reading of the included drawing figures, the claims and detailed description of the invention.

BRIEF DESCRIPTION OF THE DRAWINGS

FIG. 15 is a perspective view of a sheath assembly with magnetic field sensors shown thereon as one form of sensors for visualizing a location of a tip of the sheath assembly according to one embodiment of this invention.

FIG. 16 is a perspective view of that which is shown in FIG. 15, but for a sheath having a curving contour.

FIG. 17 is a front elevation view of a variation of the needle of FIG. 3 with a syringe attached to a hub of the needle and with leads extending from the hub for interfacing into an EP mapping system.

FIG. 19 is a front elevation view of a sheath according to one embodiment of this invention, fitted with sensors and coupled to the EP mapping system of FIG. 18.

FIG. 20 is a front elevation view similar to that which is shown in FIG. 19, but after separation of a tube portion of the sheath from a base portion of the sheath.

FIG. 21 is a front elevation view of that which is shown in FIGS. 19 and 20, and further showing how at least portions of the tube can be cut away after lead placement, for removal thereof.

FIG. 22 is a front elevation view of a sheath similar to FIG. 19, but with the interconnection to the EP mapping system occurring through the tube of the sheath, rather than through the base of the sheath.

FIGS. 23 and 24 are front elevation views similar to FIGS. 20 and 21, except for the embodiment of FIG. 22, and with connection to the EP mapping system occurring directly through a proximal portion of the tube of the sheath.

FIG. 27 is a top plan view similar to that which is shown in FIG. 26, but after the base portion of the sheath has been separated from the tube portion of the sheath at the interface there between.

FIG. 40 is a connector system for connecting navigation wires or stylets or other interventional devices in an interchangeable fashion to a common interface which then includes a cable extension to the EP mapping system, such that different devices can utilize a common interface to facilitate ease of swapping of interventional devices during a lead placement procedure.

FIG. 41 is a front elevation view of a guide wire fitted with multiple sensors according to a further embodiment of this invention.

FIG. 42 is a front elevation view of a dual wire navigation wire system with sensors thereon for location verification according to this invention.

FIG. 43 is a front elevation view of a dilator with sensors thereon and coupled to an EP mapping system according to this invention.

FIG. 44 is a front elevation view of a J-wire fitted with sensors for use with an EP mapping system according to this invention.

FIGS. 45-47 are front elevation views of luminal catheters having various different sized curved tips and with different numbers and positions of sensors thereon, for use of the luminal catheters along with an EP mapping system according to this invention.

DESCRIPTION OF THE PREFERRED EMBODIMENT

Figure 1:
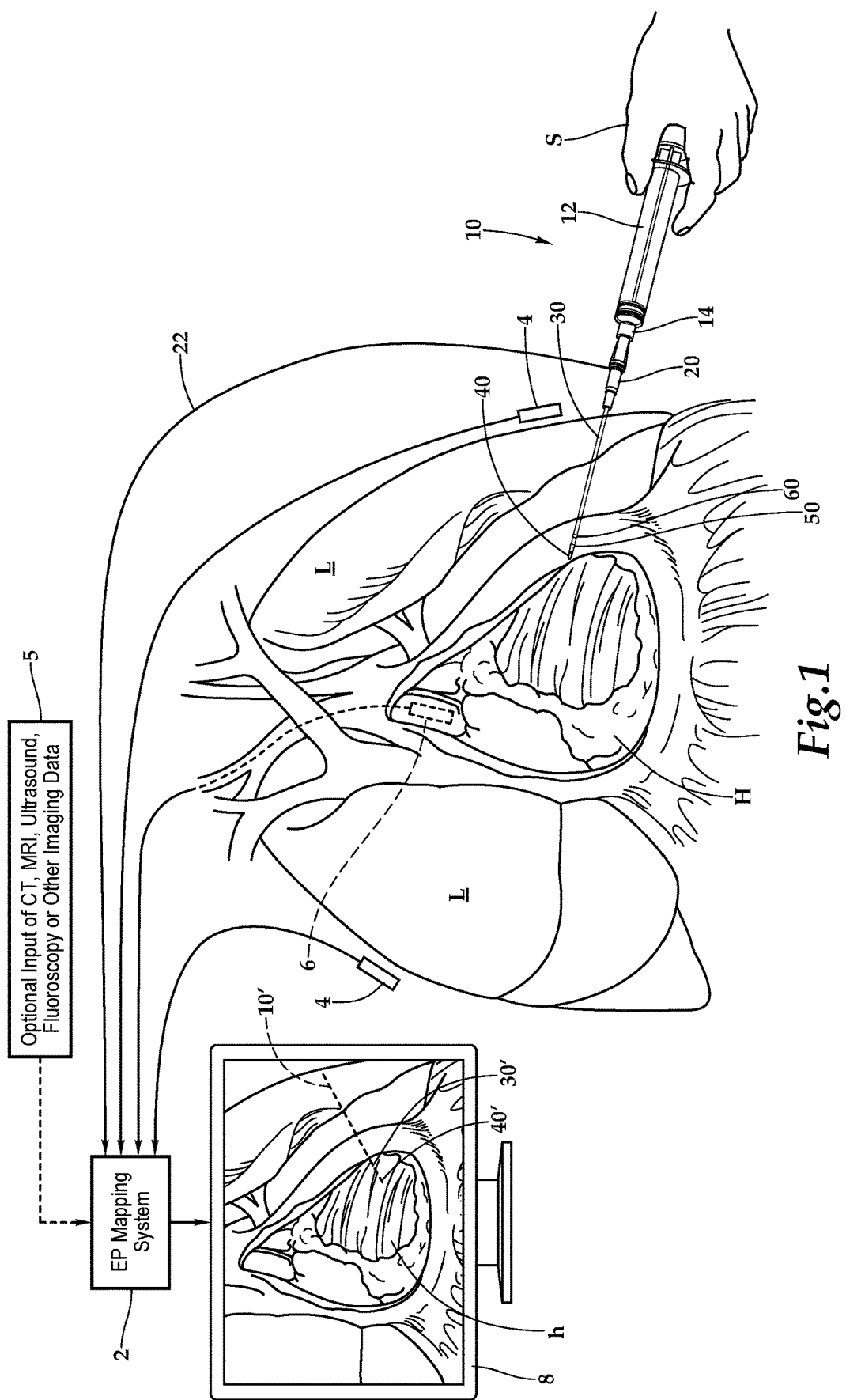
FIG. 1 is a schematic depiction of the system of this invention including a portion of a torso of a patient with a pericardiocentesis needle fitted with sensors in the form of electrodes shown engaging bodily structures proximate to the heart of a patient, and while the needle is visualized on a display of an EP mapping system, the EP mapping system relying primarily upon electrodes for generating the image displayed on the EP mapping system display.

Referring to the drawings, wherein like reference numerals represent like parts throughout the various drawing figures, reference numeral 910 is directed to an electrophysiology (EP) sheath (FIGS. 19-27) which provides one form of interventional device according to this invention. Other modularized interventional devices are shown in FIGS. 48-66 and 71-78. The sheath 910 provides support for a lead 960 to be routed to a particular desired location within or adjacent to a heart H of the patient. The sheath 910 includes sensors 950 thereon, such as in the form of electrodes or magnetic field sensors, which are coupled to an EP mapping system 2 (FIG. 18) which includes a display 8 which displays coronary structures as well as the sheath 910 (or other interventional structure) during the lead 960 placement procedure.

In particular, and with reference to FIGS. 19-27, basic details of the sheath 910 or described according to an exemplary embodiment. Other interventional devices utilizable with lead 960 placement are also generally described for use separately or in conjunction with the sheath 910. The sheath 910 includes a base 920 at a proximal end thereof. The base 920 supports an entrance 923 which can receive a lead 960 therein, as the lead 960 is threaded through the sheath 910. A tube 930 extends from the base 920, on a side thereof opposite the entrance 923 into the base 920. A stopcock assembly 940 can optionally be provided extending laterally from the base 920. A tube 930 extends from the base 920 on a side thereof opposite the entrance 923. The tube 930 provides a pathway along with the lead 960 can pass during placement of the lead 960 into a particular location within the heart H of a patient.

The tube 930 includes sensors 950 thereon, typically a plurality of such sensors 950 located along the tube 930. The sensors 950 can be electrodes or magnetic field sensors which are compatible with an EP mapping system 2 (FIG. 18), so that the tube 930 can be shown on a display 8 associated with the EP mapping system 2 adjacent to coronary structures adjacent to the heart H of a patient, along with other items such as a pericardiocentesis needle 10' having an electrode 30' adjacent to a tip 40'. The sheath 910 can have a variety of different configurations such as those depicted in FIGS. 19-27. Other interventional devices supporting lead placement can be visualized on an EP mapping system 2 by placing sensors, such as electrodes or magnetic field sensors thereon. Such other devices include exoskeletons 1010, stylets 1200, navigation wires 1400, dilators 1600, and luminal catheters 1800.

Another interventional device that can have sensors thereon to facilitate visualization within an EP mapping system 2 is a pericardiocentesis needle 10, such as that shown in FIGS. 1-17. Such a needle 10 (and other devices) are initially described in detail herein as background for the other interventional devices identified above.

Figure 2:
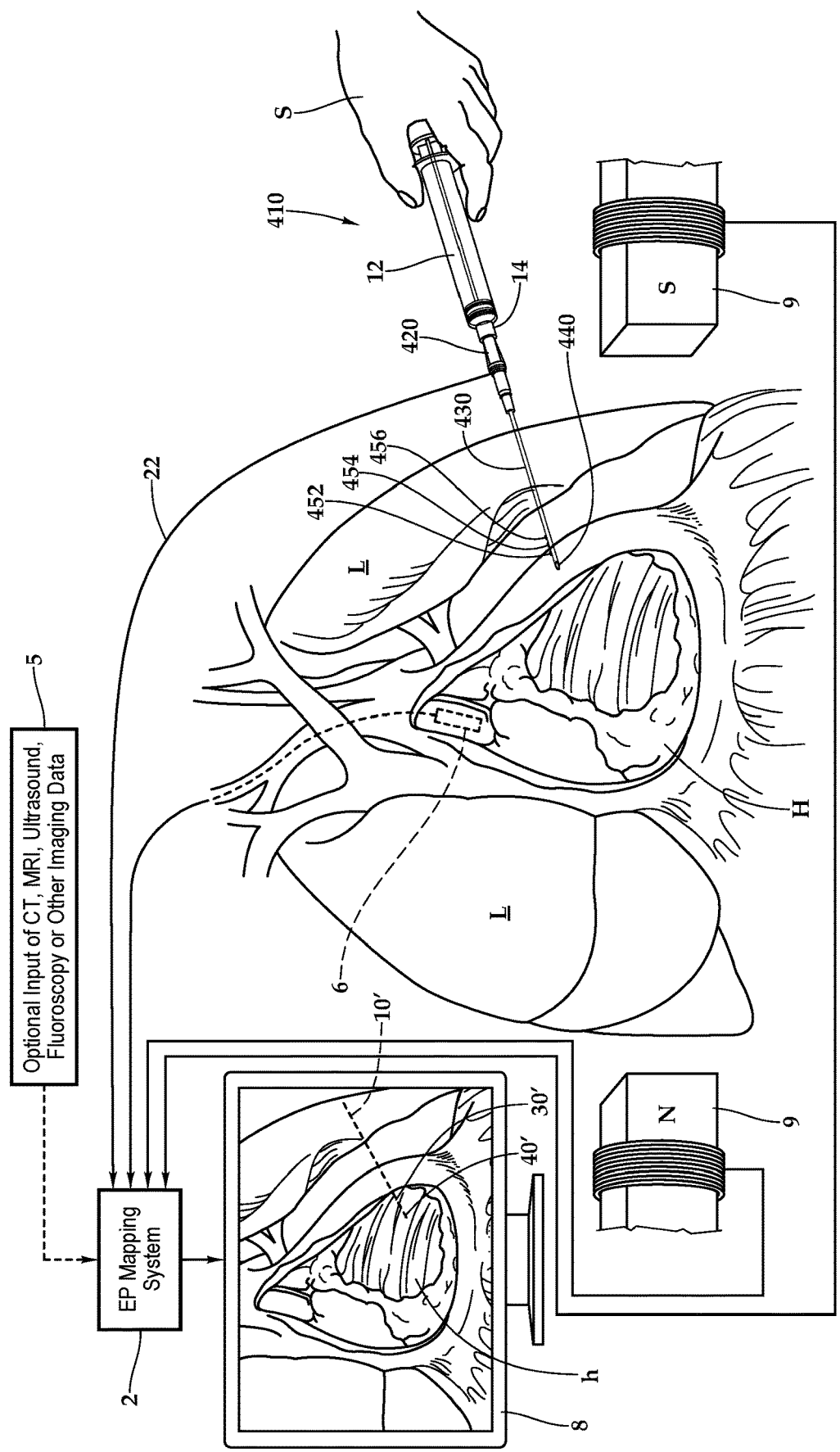
FIG. 2 is a schematic similar to that depicted in FIG. 1, but for an EP mapping system which primarily generates an image of cardiac structures based on placement of a magnetic field proximate to the patient and utilizing magnetic field sensors to localize the pericardiocentesis needle within the image displayed by the EP mapping system.

More specifically, and with particular reference to FIGS. 1 and 2, basic details of various EP mapping systems 2 are described, with which the needle 10 or other medical device of this invention is configured to inter-operably perform. The EP mapping system 2 can be any of a variety of different medical visualization systems, but most preferably those which utilize electric and or magnetic fields to determine the location of bodily structures, and in this case, particularly cardiac structures of a patient.

As a general outline, the EP mapping system 2 can include a plurality of electrodes 4 in the form of surface electrodes on a surface of the patient. FIG. 1 depicts two such surface electrodes 4, but typically more than two such surface electrodes 4 would be utilized. Also, an intracardiac electrode 6 is typically also passed intravenously to a position within or adjacent to the heart H of the patient.

As explained in detail herein-above, in one embodiment certain pairs of electrodes, such as the surface electrodes 4, switch between providing an excitation voltage resulting in the production of an electric field, and operating in a sensing mode wherever the electrodes sense voltage and/or current or other electrical properties at the locations of various electrodes. Together these electrodes, when switching between an excitation function and a sensing function, gather data about cardiac structures and other subcutaneous structures having different electrical properties, which data is converted into imagery suitable for presentation on the display 8 of the EP mapping system 2.

In one embodiment depicted in FIG. 2, the EP mapping system 2 either replaces the electrodes 4, 6 with magnetic field inducing elements such as magnets 9, or such magnetic field sources 9 augment an EP mapping system 2 which also includes electrodes 4, 6. Furthermore, cardiac structural data can be augmented with information from an auxiliary imaging source 5 and put into the EP mapping system 2. Such auxiliary input 5 can be provided from imaging devices such as computer tomography (CT), magnetic resonance imaging (MRI), ultrasound, fluoroscopy, or other imaging data.

Importantly with this invention, and as described below, the needle 10 or other transcutaneous medical device is fitted with electrodes 50, 60 or other sensors so that a position (and also preferably orientation) of the needle 10, and especially a tip 40 of the needle 10 can be visualized on the display 8 at an accurate position adjacent to heart H structures so that a position (and also preferably orientation) of the needle 10, and especially a tip 40 of the needle 10 can be visualized on the display 8 at an accurate position adjacent to the heart H and other bodily structures. On the display 8, the needle 10 appears as the needle 10' with the tip 40 appearing as a tip 40' and the shaft 30 of the needle 10 appearing as shaft 30'. A user, such as a surgeon S, can thus accurately position the needle 10 by viewing the display 8 of the EP mapping system 2 and moving the needle 10 to cause the tip 40 to be positioned where desired, while watching the display 8.

With continuing reference to FIG. 1, as well as FIG. 17, the needle 10 is described according to an initial exemplary embodiment. The needle 10 includes the hub 20 which supports the shaft 30 extending from the hub 20 to a tip 40. The hub 20 is configured to attach to other fluid handling structures, such as a syringe 12, such as through a luer fitting 14. The hub 20 also preferably has leads 22 which can extend to the EP mapping system 2, and which also connect to electrodes (or other sensors) on the needle 10. In this initial exemplary embodiment, the electrodes include a distal electrode 50 and a proximal electrode 60. By providing two electrodes 50, 60, when their position is determined a line segment between these two electrodes 50, 60 defines a central axis of the shaft 30 of the needle 10. Also, by knowing a distance that the tip 40 is spaced away from the distal electrode 50 (or other reference point), a position of the tip 40 can be precisely determined. This information can be superimposed into the imaging data set which is displayed in the display 8 of the EP mapping system 2, so that a needle 10', as well as a tip 40' of the shaft 30' can all be visualized (FIG. 1), even though no electrode is at the tip 40 of the needle 10.

While it is conceivable that the electrodes 50, 60 could have their own power supply and transmit signals associated therewith wirelessly to the EP mapping system 2, typically the electrodes 50, 60 are connected by a conducting wire 52, 62 from the electrodes 50, 60 through the leads 22 to the EP mapping system 2. FIG. 17 shows two such leads 22 which couple to the wires 52, 62 (FIG. 3) and which lead to the EP mapping system 2, such as along lead 22 (shown as a single line for convenience).

Figure 3:
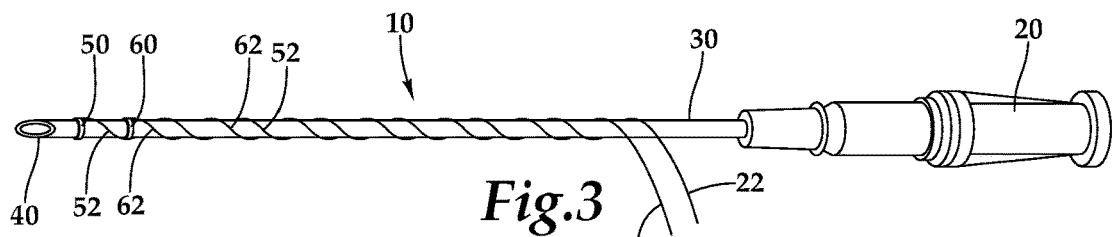
FIG. 3 is a perspective view of a pericardiocentesis needle according to a first embodiment of this invention.
Figure 5:
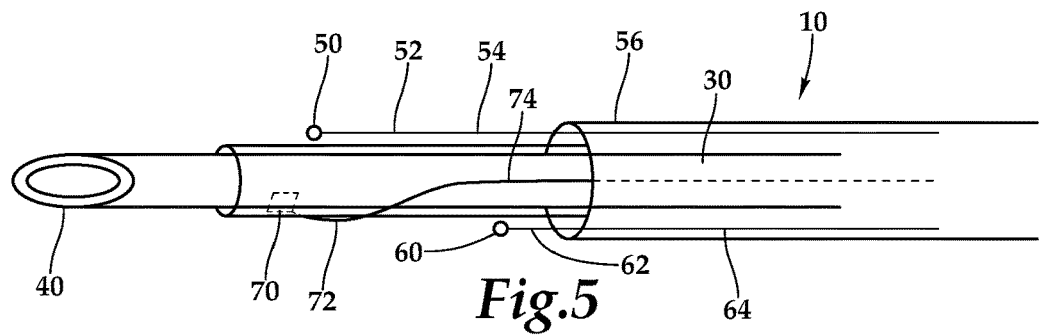
FIG. 5 is a detail of a portion of that which is shown in FIG. 3, and with electrodes shown schematically.

With particular reference to FIG. 3, a simplest form of the needle 10 with two electrodes 50, 60 coupleable to the EP mapping system 2 through external wires 52, 62 is disclosed. These wires 52, 62 are just left external to the shaft 30 of the needle 10 in this embodiment. Such an embodiment would typically perhaps only be used for testing, but could conceivably be utilized for therapeutic purposes. The wires 52, 62 might conceivably be left without any insulation jacket 54, 64 around the wires 52, 62, especially if the shaft 30 of the needle 10 is formed of a non-conducting material. However, typically these wires 52, 62 are encased within their own insulation jackets 54, 64 (FIG. 5). Also, these wires 52, 62 are preferably contained within an outer insulation 56 lining which holds the wires 52, 62 directly adjacent to the shaft 30.

Electrodes 50, 60 themselves could have any of a variety of different configurations, including configurations where they are flush with a surface of the shaft 30 of the needle 10, and embodiments where these electrodes 50, 60 extend outwardly, at least somewhat. In FIGS. 1-4, these electrodes 50, 60 are depicted as having a toroidal form and extending only very slightly away from the surface of the shaft 30. Most preferably, these electrodes 50, 60 are isolated from the shaft 30 of the needle 10 itself. For instance, and as depicted in FIG. 5, an inner lining of insulation can be provided directly adjacent to the shaft 30 of the needle 10. The electrodes 50, 60 are outboard of this innermost insulation lining. The wires 52, 62 are preferably provided with insulation jackets 54, 64 so that if these wires 52, 62 come into contact with each other, electric current is prevented from flowing therebetween. Finally, the outer insulation 56 is preferably provided to encase the wires 52, 62 and their associated insulation jackets 54, 64 are isolated from surrounding structures that the needle 10 might come in contact with. If the shaft 30 of the needle 10 is formed of non-conductive material, the innermost layer of insulation (FIG. 5) can be dispensed with.

The two electrodes 50, 60 are preferably provided a known distance apart from each other and with the distal electrode 50 a known distance away from the tip 40. For instance, the distal electrode 50 can be one inch away from the tip 40 and the proximal electrode 60 can be placed one inch away from the distal electrode 50. Such known distances between the electrodes 50, 60 and away from the tip 40 allow for accurate visualization of location and orientation of the tip 40 of the needle 10 on the display 8. As an example, if the shaft 30 of a needle 10 is extending along a central axis, with a proximal electrode 60 at an origin on the central axis, and the distal electrode 50 is at a one inch mark on this axis, it is known that the tip 40 will be at the two inch mark on this central axis. The coordinates of this central axis can be associated with what is fed to the display 8, and not only the positions of the electrodes 50, 60 can be provided, but also a virtual needle 10' can be animated and presented on the display 8, with the needle 10' extending right up to the tip 40'.

Bodily structures on the display 8 might hide the needle 10' at least somewhat. Known techniques with EP mapping systems 2 can be utilized to make sure that important structures can still be visualized. As one option, body structures "in front of" the portions of the needle 10' adjacent to the tip 40' can be cut away so that the tip 40' of the needle 10' can be seen. As another alternative, at least portions of the needle 10' can be shown in a phantom or broken line manner which perhaps becomes more pronounced or less pronounced based on a depth of the needle away from a view and perspective point, to represent depth. As another option, video editing tools can be utilized by a user to selectively remove bodily structures presented on the display 8 in a customizable fashion to display what the surgeon S or other medical practitioner wants to see, but remove enough detail so that important portions of the needle 10' can be clearly seen.

Figure 4:
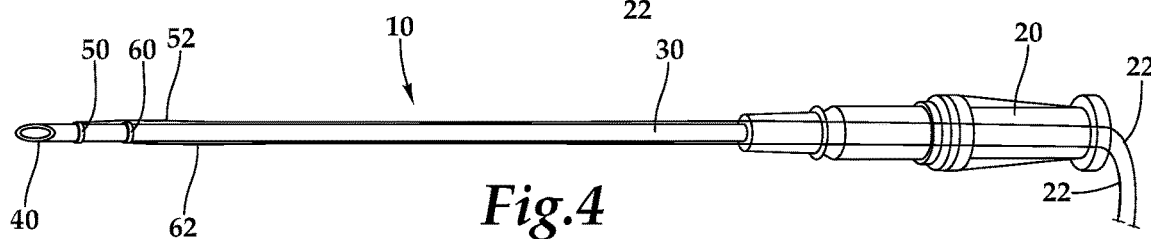
FIG. 4 is a perspective view of a modified version of that which is shown in FIG. 3.

In FIG. 4 a variation of the needle 10 is displayed where the wires 52, 62 are held adjacent to the shaft 30, such as by placement inboard of outer insulation 56 (FIG. 5). The wires 52, 62 coupled to the electrodes 50, 60 are routed through the hub 20 in this embodiment, where they transition into the leads 22 extending to the EP mapping system. FIG. 5 further depicts, somewhat schematically, how different layers of insulation including innermost insulation and outer insulation 56 are located inboard and outboard of the electrodes 50, 60 and with the outer insulation 56 stopping short of positions for the electrodes 50, 60 so that the electrodes 50, 60 are not blocked from sensing electrical characteristics of bodily structures adjacent to the needle 10 and sensing the electric field sufficiently precisely to allow the electrodes 50, 60 to be located within a three-dimensional space adjacent to the heart H of a patient, without disruption by the electrically insulative character of the other insulation 56.

Figure 6:
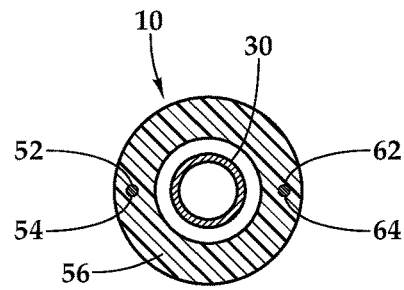
FIG. 6 is an end full sectional view of an embodiment of that which is shown in FIG. 3, which has both a proximal electrode and a distal electrode.

Electrodes in FIG. 5 are seen schematically, rather than with any particular geometric configuration. FIG. 6 depicts how the wires 52, 62 and associated insulation jackets 54, 64 are located outboard of the shaft 30 but inboard of outer insulation 56 which is wrapped around an outer side of the wires 52, 62, or has the wires 52, 62 embedded within the outer insulation 56.

FIG. 5 also shows an optional additional sensor in the form of a force sensor 70. This force sensor 70 can be a strain gauge mounted to the shaft 30 of the needle 10, or some other force sensor 70. The force sensor 70 detects compression forces between the tip 40 and the hub 20. For instance, and especially when the tip 40 is large or less sharp, the tip 40 does not penetrate bodily tissues unless sufficient force is applied. In some instances, it is desirable to penetrate some tissues, but not others. For instance, when performing pericardiocentesis, the skin and surface anatomy, and the pericardium are penetrated, but one does not want to penetrate the myocardium. The force sensor transmits a signal, typically along a wire 72 inside of an insulation jacket 74 to the EP mapping system 2 or to a separate display of needle force. The signal can be calibrated and used to keep the tip 40 of the needle 10 from penetrating structures that require more force than a threshold amount, by having the surgeon S monitor the force sensed by the force sensor 70 and keeping it below the threshold maximum force.

Figure 7:
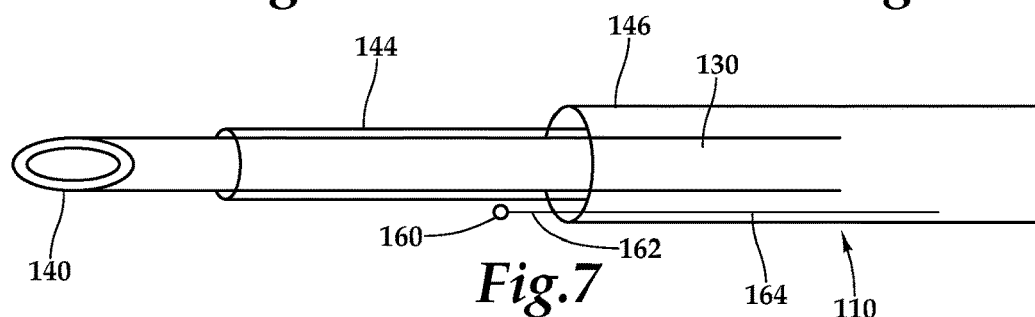
FIG. 7 is a perspective view of an embodiment of that which is shown in FIG. 3 which has a single electrode depicted schematically thereon, and where a tip of the needle can be an electrode.

With particular reference to FIG. 7, details of an alternative embodiment needle 110 are described. This alternative needle 110 is configured so that the tip 140 of the needle 110 can act as a distal electrode. The needle 110 includes a shaft 130 extending to the electrode tip 140. Shaft insulation 144 surrounds the shaft 130. Portions of the shaft 130 extending beyond the shaft insulation 144 generally act as an electrode. Preferably the shaft insulation 144 stops just short of the electrode tip 140, so that an approximation of a singular point can be associated with this electrode tip 140. Preferably in this embodiment, a proximal electrode 160 is also provided which is coupled to a wire 162 which preferably has its own insulation jacket 164. Outer insulation 146 can wrap around the wire 162 to hold the wire 162 adjacent to the shaft 130, but while preventing an electrical connection therebetween. The proximal electrode 160 would preferably be provided at a known distance away from the electric tip 140, so that the needle 110 would generally be effective in a manner similar to other multi-electrode needles such as the needle 10 (FIGS. 1-6).

Figure 9:
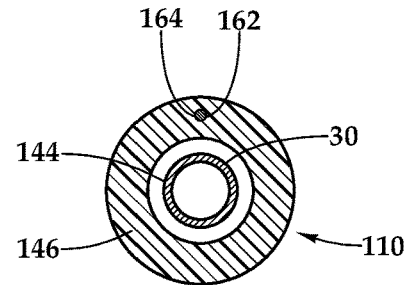
FIG. 9 is an end full sectional view of that which is shown in FIG. 7.

FIG. 9 depicts the embodiment of FIG. 7 in a full sectional end view, according to one embodiment where the wire 162 and insulation jacket 164 are embedded within the outer insulation 146, rather than merely having the outer insulation 46 wrapped outside of the wire 162.

Figure 8:
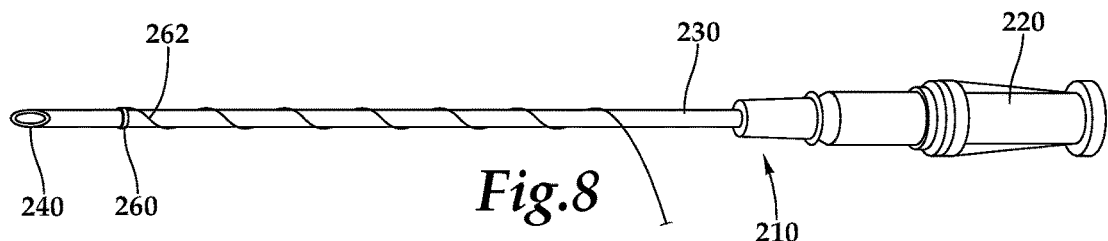
FIG. 8 is a perspective view of a modified version of that which is shown in FIG. 7.

FIG. 8 depicts a unipolar electrode needle 210. This unipolar electrode needle 210 includes a hub 220 with a shaft 230 of the needle 210 extending away from the hub 220 to a tip 240. A proximal electrode 260 is coupled to the shaft 230 a known distance away from the tip 240. A wire 262 extends from the proximal electrode 260 and is fed into the EP mapping system 2 (FIG. 1). Unipolar electrodes such as the proximal electrode 260 function by being coupled with some other electrode within the EP mapping system 2 or associated with some portion of the needle 210, or some other reference, so that meaningful information can be gathered with regard to the position (and preferably also orientation) of the needle 210.

In the embodiment depicted in FIG. 8, the wire 262 is merely wrapped around the exterior of the shaft 230, but could be covered with an outer insulation player, embedded within the shaft 230 or otherwise conveniently routed, or wiring could be dispensed with should be unipolar electrode 260 be fitted with a micro-mechanical power source of some form and a transmitter and other electronics to allow it to function as an electrode without an associated wire 262.

Figure 10:
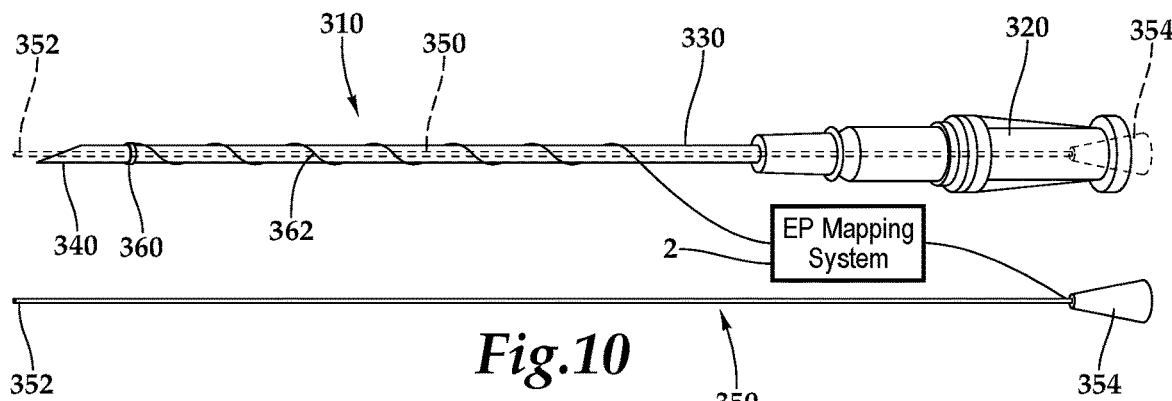
FIG. 10 is a perspective view of an embodiment of that which is shown in FIG. 3 where a single electrode is placed upon the needle and a stylet electrode is associated with the needle, the stylet electrode shown exterior to the needle and shown in broken lines placed within the needle.

With particular reference to FIG. 10, details of a needle/stylet 310 combination are described. In this embodiment a hub 320 supports a shaft 330 extending out to a tip 340, similar to the needle 10 depicted in FIG. 3. However, only one electrode in the form of a proximal electrode 360 is provided on this shaft 330 spaced a known distance away from the tip 340. Wire 362 preferably extends from this proximal electrode 360 and is fed to the EP mapping system 2. A stylet 350 is also coupled to the EP mapping system 2 and has a distal end 352 opposite a base 354. The stylet 350 is preferably sufficiently long that the distal end 352 of the stylet 350 can pass entirely through a hollow center of the shaft 330 and extend out of the tip 340. The stylet 350 is preferably formed of electrically conductive material so that the distal end 352 can act as an electrode in this embodiment. As an alternative (or in addition), one or more magnetic field sensors can be placed on the stylet to convey its position (and preferably also orientation within the EP mapping system 2).

Preferably the shaft 330 is formed of electrically non-conductive material. As an alternative, the stylet 350 can have an outer insulative jacket formed of electrically non-conductive material or an interior of the shaft 330 can be coated with or otherwise lined with electrically non-conductive material. Between the distal end 352 of the stylet 350 and the proximal electrode 360, the combined needle/stylet 310 can function similar to a dual electrode needle such as that disclosed in FIGS. 1-6. The stylet 350 is movable relative to the shaft 330. The distal end 352 of the stylet 350 can be provided as a blunt tip, or with a sharpened tip, and with the tip 340 of the shaft 330 configured either to be sharp or somewhat blunted, so the various different functionalities can be provided between the shaft 330 and stylet 350 as is known in the stylet and needle arts as they pertain to cardiac surgery and related medical procedures and devices.

Figure 11:
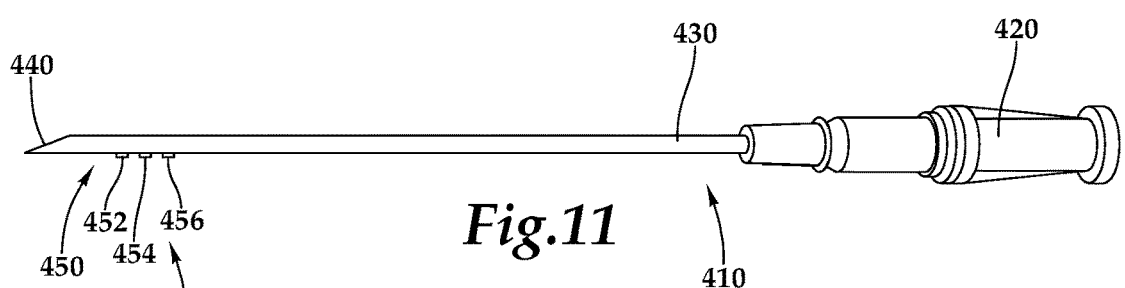
FIG. 11 is a perspective view of an embodiment of that which is shown in FIG. 3 which utilizes magnetic field sensors rather than electrodes, such as for use within the EP mapping system of FIG. 2.

With particular reference to FIG. 11, a needle 410 is disclosed which includes sensors which are preferably in the form of a magnetic field sensor set 450. The needle 410 includes a hub 420 upon which a shaft 430 is supported and extending out to a tip 440. The magnetic field sensor set 450 preferably includes three separate magnetic field sensors 452, 454, 456, such as sensors oriented in three mutually perpendicular orientations (e.g. X, Y and Z axes), so that the magnetic field from the sources 9 (FIG. 2) can be most accurately characterized at the location adjacent to this magnetic field sensor set 450. For simplicity, the sensors 452, 454, 456 are identified as boxes along a line, but could be oriented non-linearly and would most typically be solenoids or other coils with a generally cylindrical form.

Position (and preferably also orientation) can be ascertained based on a sensed intensity of the magnetic field relative to sources 9 (FIG. 2) of the magnetic field, and the position of bodily structures, and particularly cardiac structures which can be identified by electrodes, other magnetic sensors, other imaging systems, or combinations thereof. Thus, a position of the needle 410 fitted with the magnetic field sensor set 450 can be accurately determined and then displayed on the display 8 of the EP mapping system 2 (FIG. 2).

Figure 12:
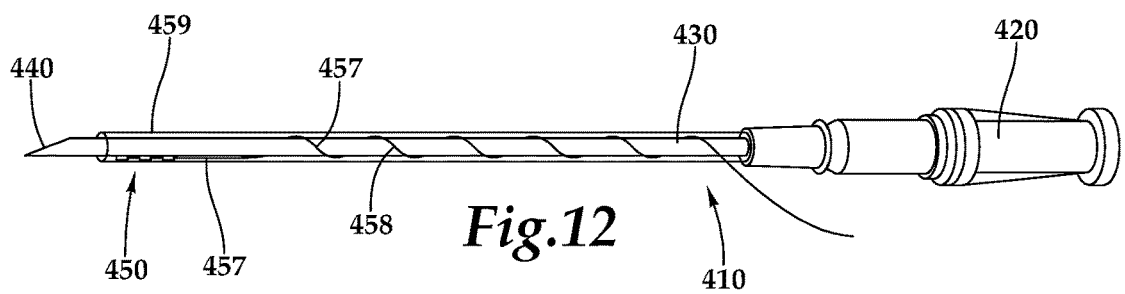
FIG. 12 is a perspective view of a modified version of that which is shown in FIG. 11.

Other details of the needle 410 are preferably similar to those disclosed above with respect to FIGS. 1 and 3-5. In this embodiment, for simplicity, no wires are shown, but typically, and as depicted in FIG. 12, the sensor set 450 would have at least one wire 457 extending therefrom (and optionally three wires in some embodiments) one to each individual sensor 452, 454, 456, and preferably with an insulation jacket 458 outboard of the wire 457 and within a jacket 459 surrounding the wires 457 and holding them adjacent to the shaft 430 of the needle 410, as depicted in FIG. 12, as one example.

Figure 13:
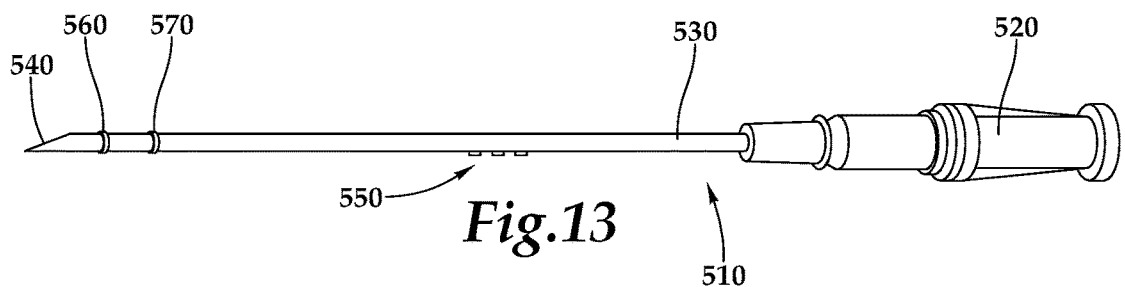
FIG. 13 is a perspective view of an alternative embodiment of that which is shown in FIG. 11 where the magnetic field sensors are located more proximal to a hub of the needle, and with optional electrodes are added to the needle so that a hybrid collection of magnetic field sensors and electrodes are provided together on a common needle, according to this embodiment.

With particular reference to FIG. 13, a hybrid needle 510 is disclosed that utilizes both magnetic field sensors 550 and at least one electrode 560, 570. In the embodiment depicted, a needle 510 includes a hub 520 with a shaft 530 extending therefrom to a tip 540. The shaft 530, includes a sensor, typically at any location thereon, but in the example depicted slightly closer to the hub 20 than to the tip 540, in the form of a magnetic field sensor set 550. Additionally, at least one electrode, and preferably both a distal electrode 560 and a proximal electrode 570 are also located upon the shaft 530. While wires are not depicted, they would typically extend from these sensors in the form of the magnetic field sensor set 550, as well as from the electrodes 560, 570. Information from the sensors is passed on to the EP mapping system 2 for most accurate visualization of the needle 510.

Figure 14:
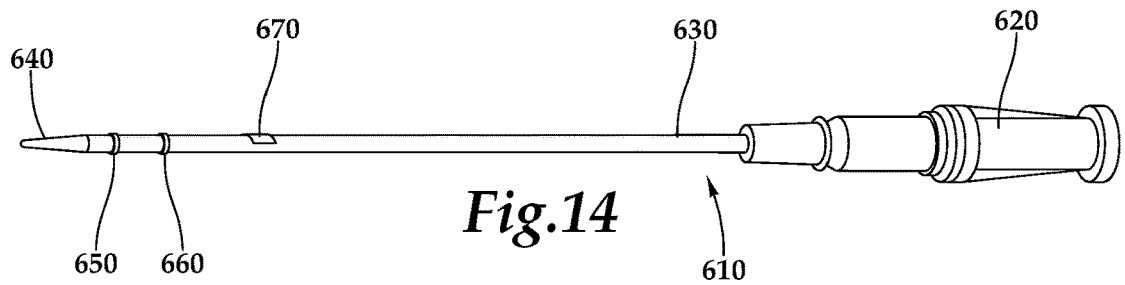
FIG. 14 is a perspective view of a dilator with electrodes thereon for visualization within an EP mapping system such as that disclosed in FIG. 1.

With particular reference to FIG. 14, an embodiment of this invention is depicted where a dilator 610 is fitted with electrodes 650, 660 as one form of sensor to allow for visualization of the dilator 610 within an EP mapping system 2. The dilator 610 includes a hub 620 with a shaft 630 extending therefrom to a tip 640. In this disclosed embodiment, two electrodes 650, 660 are coupled to the shaft 630 at known distances away from the tip 640. A force sensor 670 can also be provided. As one option, one of these electrodes 650 could be located at the tip 640. Typically wires extend from these electrodes 650, 660 and force sensor 670 and appropriate insulation is provided to keep these wires extending from the electrode 650, 660 from shorting out each other as they are routed back to the EP mapping system 2. With such a dilator 610, dilator placement can be most effectively controlled utilizing the EP mapping system 2, and particularly the display 8 thereof, to guide a surgeon S or other medical professional in the placing of the dilator 610 where desired.

With particular reference to FIGS. 15 and 16, two variations on a sheath, including a straight sheath 710 and a curved sheath 810 are disclosed. Shafts 730, 830 are either straight or curved, extending out to tips 740, 840. Hubs 720, 820 are provided opposite these tips 740, 840. With these sheaths 710, 810 valves 725, 825 are preferably provided at the hubs 720, 820 for placement of a dilator or other structure therethrough during a placement (also known as "introduction") procedure. Such devices are also referred to as introducers. A separate fluid control line typically interfaces with the hubs 720, 820, in the form of fluid manifolds 727, 827 to allow for fluid flow after placement of the sheaths 710, 810 where desired. Sensors, depicted in these embodiments as magnetic field sensor sets 750, 850 are provided upon the shafts 730, 830, and preferably adjacent to the tips 740, 840, which allow for a location of these sheaths, and particularly tips thereof, to be visualized through a display 8 of an EP mapping system 2 and for placement where desired. In addition to sheaths 710, 810 other medical devices can similarly be fitted with sensors to facilitate their viewing on a display 8 of an EP mapping system 2. Such other devices include catheters, scalpels, ablation tools, biopsy needles, shunts, drain tubes, etc.

While the magnetic field sensor or electrode (or set of two or more thereof, collectively considered as "the sensor") is shown attached to the needle body itself, in other embodiments the sensor could be on the hub of the needle or could be an accessory that is removably attachable to the needle. The accessory with the sensor can connect the needle to a syringe as an intermediate structure that acts as a syringe interface, or the accessory with the sensor can fit over the needle body itself. Similarly, the sensor could be within the syringe that is mounted on the needle. In each case, a cable would be routed back to the EP mapping system 2. The tip of the needle would be a known distance from this sensor and the EP mapping system 2 would display the needle in an accurate position and orientation by drawing the needle extending this known distance away from the actual position of the sensor on the hub, syringe or syringe interface.

Figure 18:
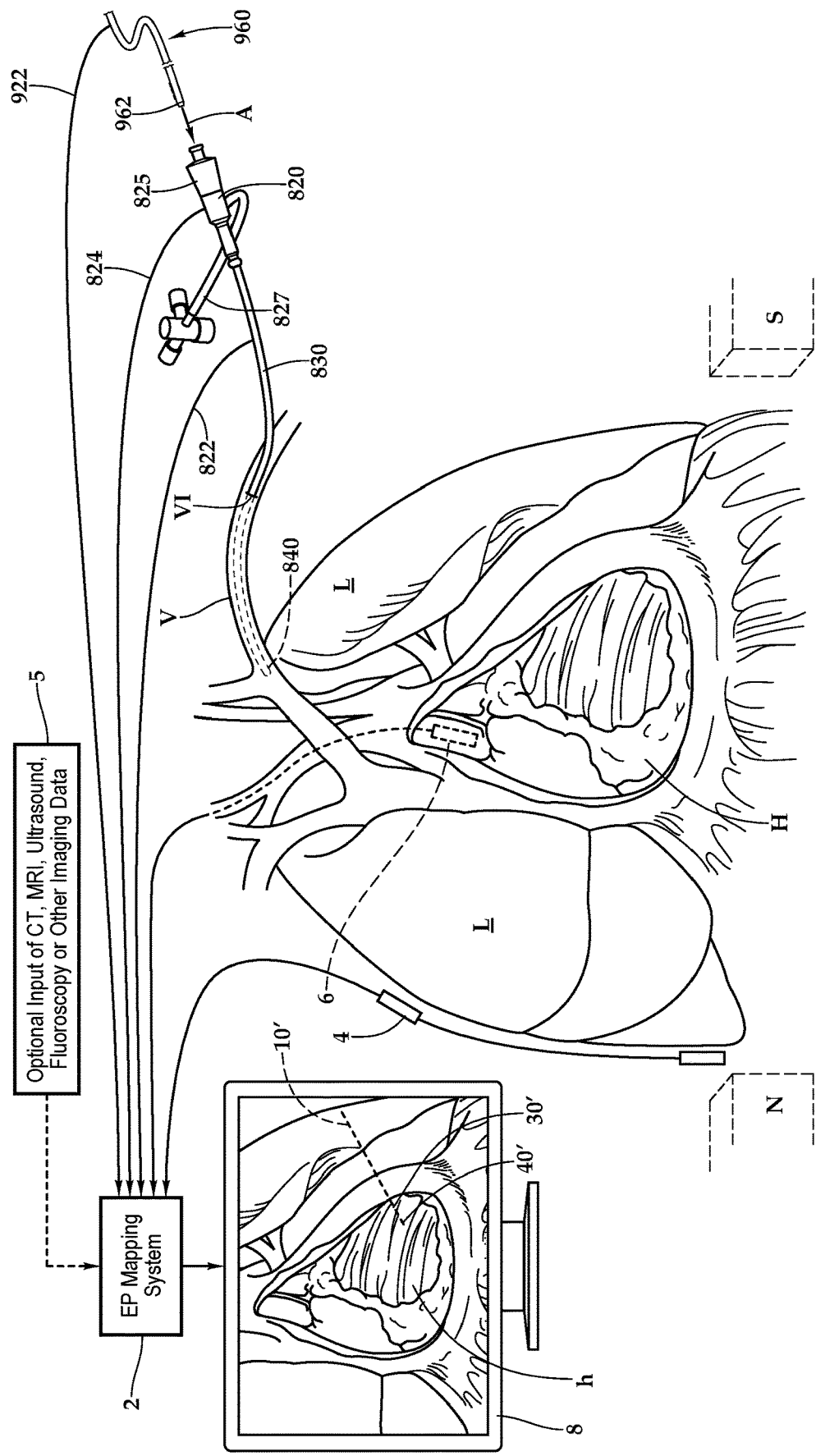
FIG. 18 is a schematic depiction similar to that which is shown in FIG. 1, but for a sheath passing into a subclavian vein, rather than for a pericardiocentesis needle.

With particular reference to FIG. 18, details of an EP mapping system 2 utilized during placement of a cardiac lead 960, such as a pacemaker lead, are described according to one embodiment which is exemplary of how the EP mapping system 2 can assist in coronary lead 960 placement. As depicted in FIG. 18, a subclavian vein V is utilized for accessing interior portions of the heart H for lead 960 placement. A sheath 810 is depicted with a tube 830 thereof passing through a vein incision VI and into the subclavian vein V. The sheath 810 also includes a base 820 with an entrance 825 through which the lead 960 can be placed. This sheath 810 also includes a stopcock subassembly 827 and a cable 824 or cable 822 which feed information to the EP mapping system 2 from sensors placed along the tube 830 of the sheath 810, either directly from the tube 830 along the cable a 822 or through the base 820 along the cable 824.

The sheath 810 has the tube 830 thereof inserted into the subclavian vein V and then routed appropriately to a desired final location. Sensors on the tube 830 of the sheath 810 help to determine if it is located in the proper portion of the heart H. Either the lead 960 is already located within the sheath 810 during its placement, or the sheath 810 is first placed where desired, and then the lead 960 is routed through the sheath 810 (along arrow A of FIG. 18) to place the lead 960 were desired.

The lead 960 includes a lead tip 962 opposite a proximal end 964. The lead tip 962 is configured to deliver electric therapy to the heart, such as placing impulses. The proximal end 964 of the lead 960 (FIGS. 26 and 27) can be coupled to a pacemaker or intracardiac defibrillator (ICD) as a source of electric signal to be routed along the lead 960. Other approaches besides that through the subclavian vein V can alternatively be utilized with similar equipment.

With particular reference to FIGS. 19-27, an alternative EP sheath 910 to the sheath 810 depicted in FIG. 18 is disclosed in various different embodiments. A primary aspect of this EP sheath 910 is that the base 920 thereof can be separated from the tube 930 thereof, such as after placement or after a first portion of placement of the sheet 910 has occurred.

The sheath 910 includes a base 920 with the tube 930 extending in elongate fashion from the base 920. The base 920 includes an entrance 923 on one side thereof, opposite the tube 930. A fastener 924 is located within the base 920. This fastener 924 is configured to releasably clamp to the lead 960 so that the lead 960 can be held adjacent to the sheet 910, such as in an environment where the lead 960 is first placed through the sheath 910 before the sheath 910 is placed into a coronary pathway adjacent to the heart H of the patient, so that the sheath 910 is supporting the lead 960 during placement.

A cable 926 extends from this base 920 as well, in the embodiments depicted in FIGS. 19 through 21. In the embodiments of FIGS. 22-27 the cable 926 connects to a proximal terminus 934 of the tube at 930, separate from the base 920. The base 920 includes an interface 928 on the side of the base 920 adjacent to the tube 930. This interface 928 can be removably attached to the base 920 (along arrow B of FIGS. 20, 21, 23 and 24). Such removable attachability can be by configuring the interface 928 and base 920 to form two halves of a threaded pair, with one having male threads and the other having matching female threads, or can be configured as a clamp with the base 920 having a closed orientation clamping down on to the interface 928 and an open orientation where the interface 928 is released by the base 920. In one embodiment, the interface 928 merely has a friction fit with the base 920 and can be separated with appropriate tension force applied therebetween. Other forms of fasteners could alternatively do utilized.

Preferably, the interface 928 can be broken open to cause the tube 930 to be split longitudinally into at least two separate pieces. Such tearing open is depicted along arrow C of FIGS. 21 and 24. Such separation can facilitate removal of the tube 930 after placement of the lead 960 where desired.

The sensors 950 are located on the tube 930 most preferably with one sensor 950 adjacent to a distal tip 932 of the tube 930. A plurality of sensors 950 are provided, preferably with constant space therebetween, along the tube 930 and extending at least part of the way toward the proximal terminus 932 of the tube 930. Each of these sensors 950 is coupled via a wire 927 through the proximal terminus 934, along the cable 926, through a junction 929, and then as exposed individual wires terminating at connectors 925 which can be plugged into the EP mapping system 2. Other wire routing systems could alternatively be utilized. Each wire 927 typically involves an electrically conductive pathway which typically includes some form of insulation surrounding each conductive pathway.

Each sensor 950 can be either an electrode or a magnetic field sensor. The EP mapping system 2 can be of a variety which is based entirely upon electrodes and the establishment of an electric field in the chest cavity of the patient surrounding the heart H, or can be a combination of electrodes and magnetic field sensors, and with a magnetic field established surrounding a torso of the patient. Through differing electric and magnetic properties of the tissues within and surrounding the heart H of the patient, variable magnetic field strength and/or impedance, or other electric field measurement can be taken and correlated to coronary structures or other structures. These coronary structures and related structures can then be displayed on the display 8 of the EP mapping system 2. By placing sensors 950 on the tube 930, the tube 930 can also be visualized on this display 8 at proper location adjacent to other bodily structures. A surgeon or other medical professional can thus view the display 8 and see where the tube 930 of the sheath 910 (or other interventional device) is located, and, by watching the display 8 in real time, can place the lead 960 and/or other interventional device precisely where desired.

Figure 25:
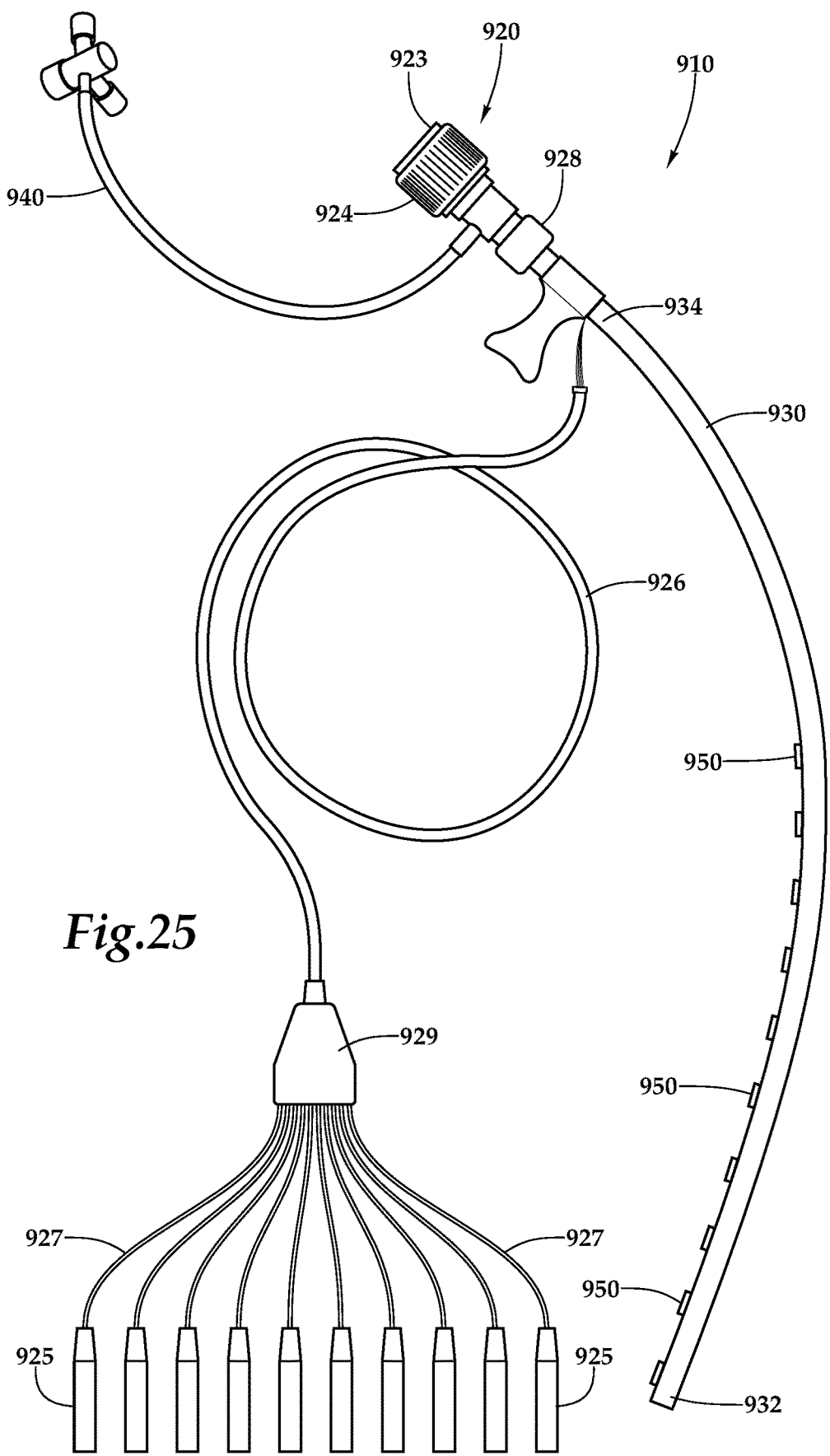
FIG. 25 is a top plan view of a sheath according to a further embodiment of this invention with details of a cable for interconnection to the EP mapping system and separation details at an interface between a base and a tube of the sheath.
Figure 26:
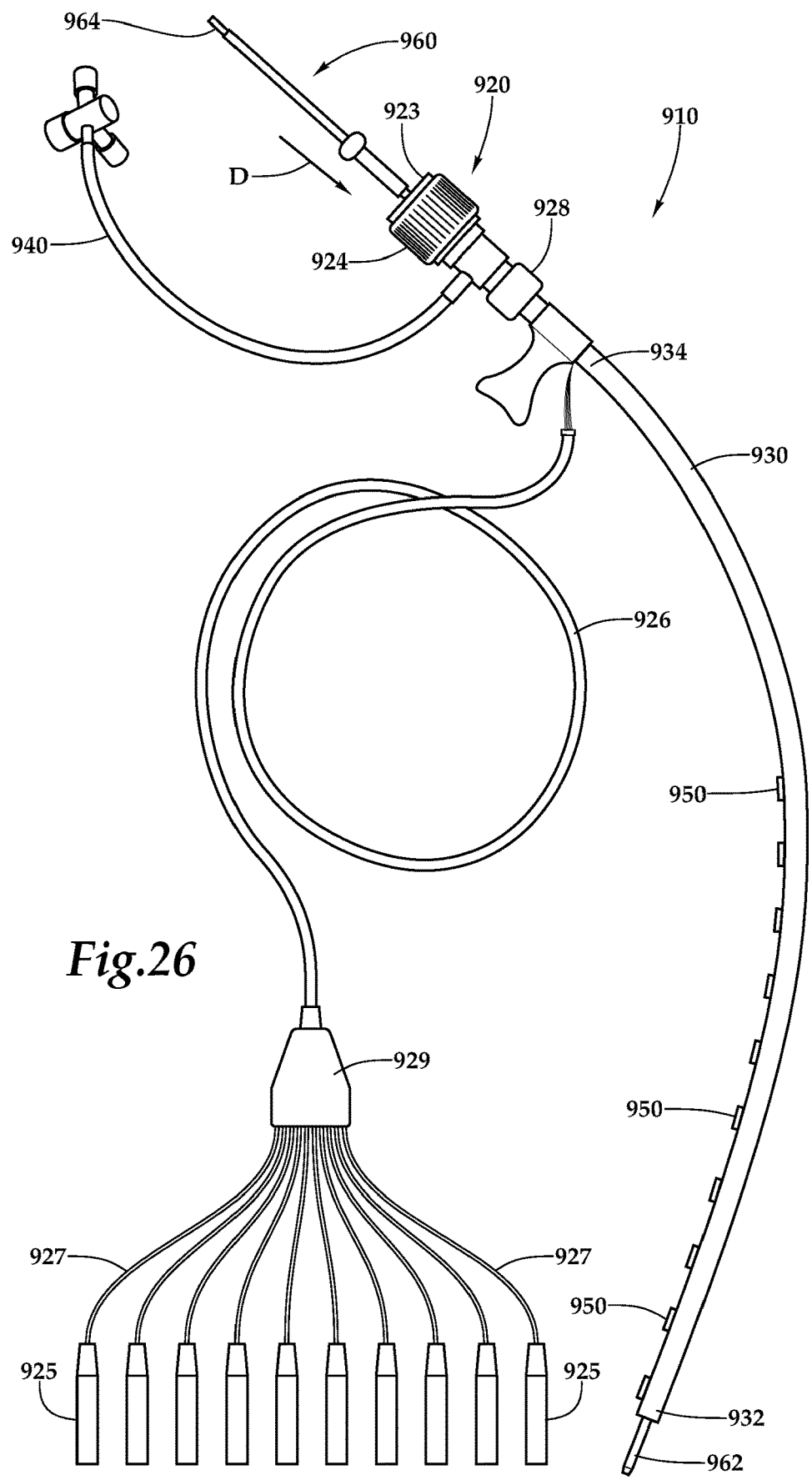
FIG. 26 is a top plan view similar to that which is shown in FIG. 25, but after a lead has been placed through the base and tube of the sheath.
Figure 27:
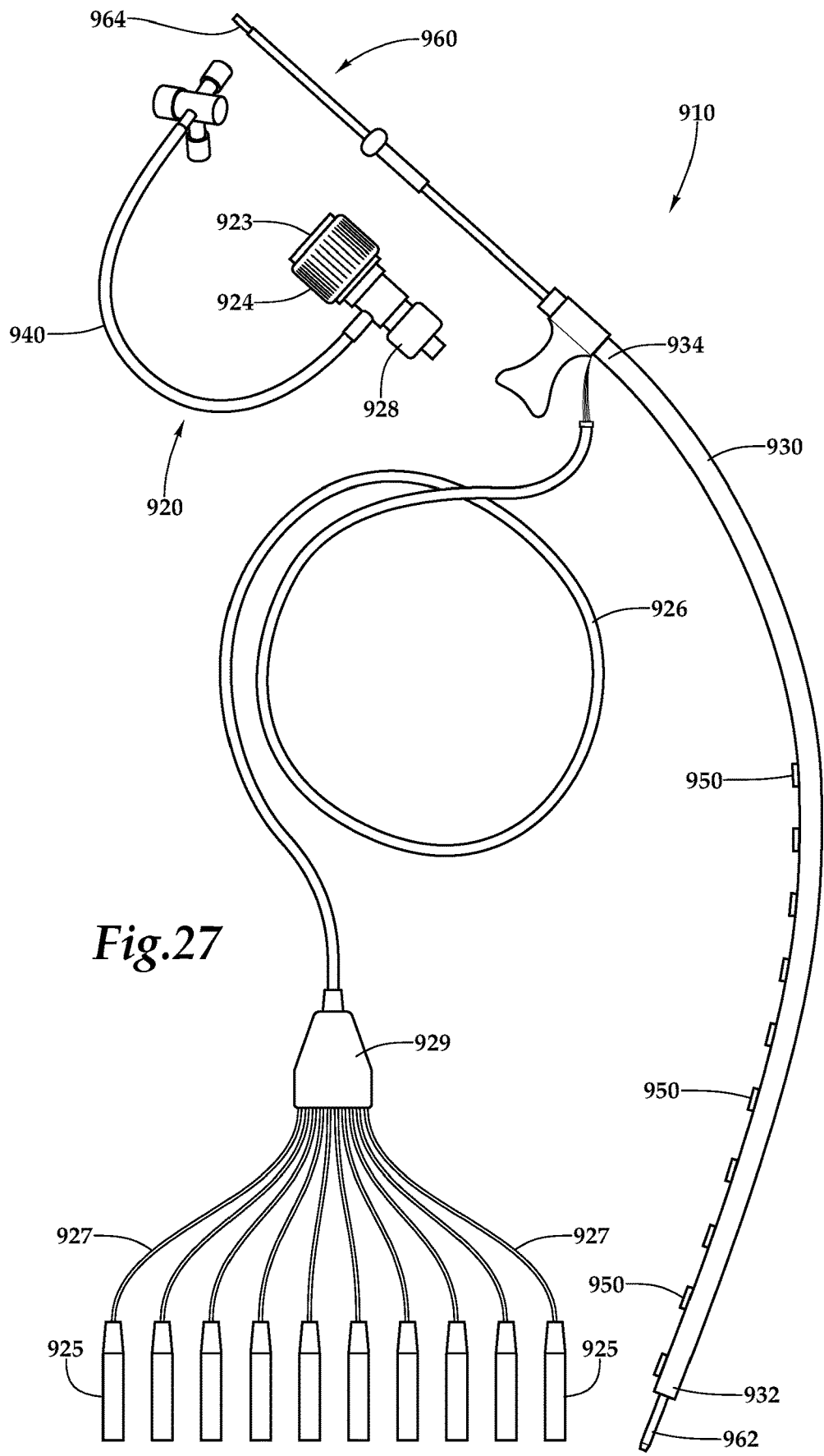

FIGS. 25 through 29 show a particular embodiment with ten sensors 950 along the tube 930. In FIG. 25, sheath 910 has not yet been loaded with the lead 960. In FIG. 26, the lead 960 has been routed (along arrow D) through the entrance 923 of the base 920, and then through the tube 930 and extending out the distal tip 932. In FIG. 27, the lead 960 is still in place within the sheath 910, but the base 920 and associated stopcock assembly 940 have been removed, leaving just the tube 930 upon the lead 960. The sensors 950 on the tube 930 identify the position of the lead 960.

With particular reference to FIGS. 28-33, various embodiments of an exoskeleton 1010 variation on the sheath 910 are described, according to an exemplary embodiment. The exoskeleton 1010 includes a base 1020 with the cable 1022 coupled thereto, and leading back to the EP mapping system 2. A spine 1030 extends in elongate fashion from the base 1020. The base 1020 can have an entrance passing therethrough, which allows the lead to pass through the base 1020, and the base 1020 can also act as a fastener to hold the lead tightly to the base 1020 after it has been routed through the base 1020. The spine 1030 has a series of splines 1040 extending laterally therefrom. These splines 1040 are formed of resilient material and can have the lead snapped between two fingers of each spline 1040.

Figure 28:
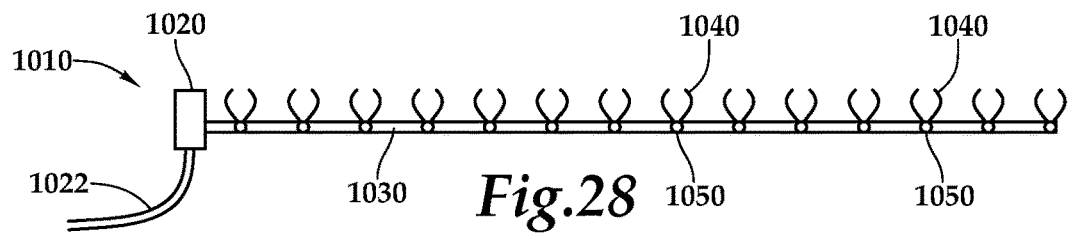
FIG. 28 is a front elevation view of an exoskeleton for attachment to a cardiac lead and for placement of EP mapping system sensors adjacent to the lead during placement within a cardiac space.
Figure 29:
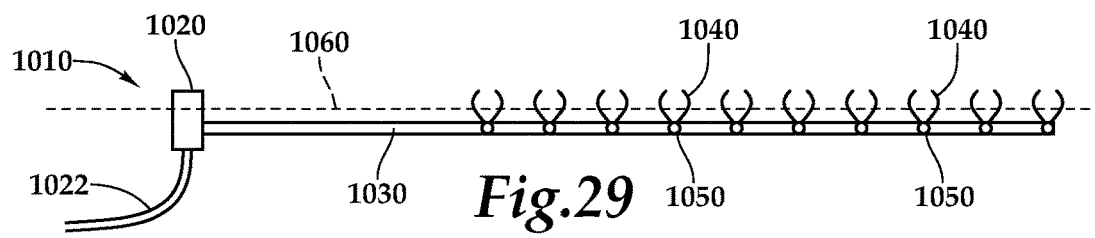
FIG. 29 is a front elevation view similar to that which is shown in FIG. 28, but with an optional additional spine of the exoskeleton shown in broken lines, and coupled to splines of the exoskeleton.

While the splines 1040 are shown with space therebetween maximized, they would typically be rotated 90° from that depicted, so that a widest spacing between fingers of the splines would be presented on either side of the lead after it passes through the entrance in the base 1020. Sensors 1050 are provided along the spine 1030. In the embodiment of FIG. 28, each spline 1040 also has a sensor 1050. In the embodiment of FIG. 29, the splines 1040 are concentrated near a distal end of the spine 1030, with one sensor 1050 for each spline 1040. Also in the embodiment of FIG. 29, a second optional spine 1060 (shown in broken lines) can be provided generally parallel with the main spine 1030. This second spine 1060 can also be attached to each of the splines 1040. Maneuvering the two spines 1060 in a differential fashion can cause the splines 1040 to more readily grip or release a lead passing through the splines 1040.

Figure 30:
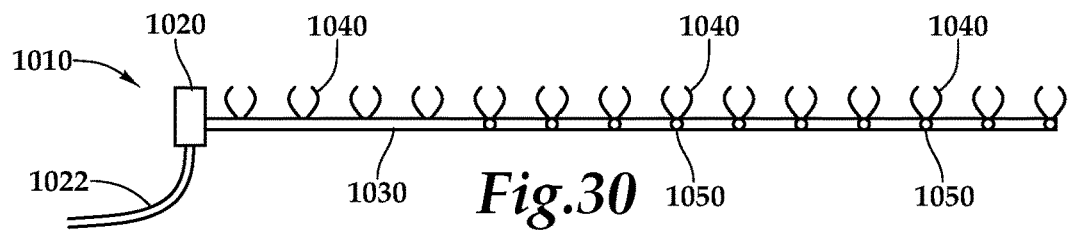
FIG. 30 is the front elevation view of the exoskeleton of FIG. 28, according to a modified embodiment with electrodes on only some of the splines.
Figure 31:
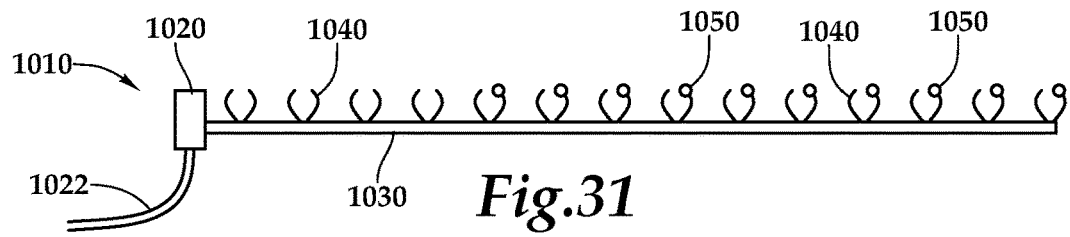
FIG. 31 is a front elevation view of an alternative embodiment of that was shown in FIG. 28, with the sensors located upon the splines rather than upon the spine.

In the embodiment of FIG. 30, the exoskeleton 1010 is shown with sensors 1050 on only some of the splines 1040. In the embodiment of FIG. 31, an exoskeleton 1010 is shown where the sensors 1050 are placed upon the splines 1040 rather than on the spine 1030, and only the splines 1040 closest to a distal end of the exoskeleton 1010 include the sensors 1050 thereon.

Figure 32:
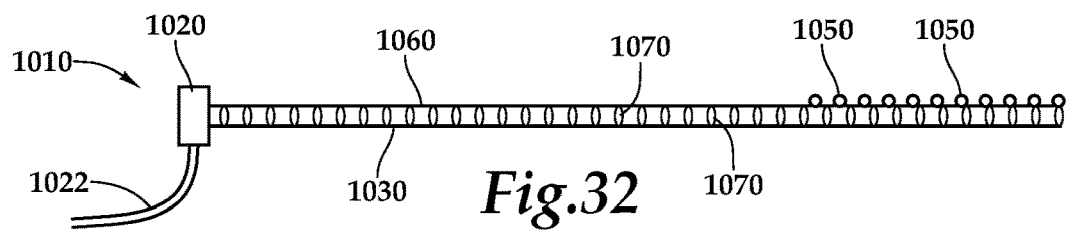
FIG. 32 is a front elevation view of an alternative embodiment of that which is shown in FIG. 28 with the splines replaced with thin wire loops which surround the lead during placement.

In the embodiment of FIG. 32, rather than having the splines 1040, a series of wire loops 1070 are provided. In this embodiment, a pair of spines 1030, 1060 are also provided, and the sensors 1050 are concentrated near a distal end of the exoskeleton 1010. Fine wires 1070 can be routed around the lead, such as during placement, and then the spines 1030, 1060 can be manipulated to remove the exoskeleton 1010 after the lead is placed where desired. Alternatively, the spines 1030, 1060 can be manipulated to cause the exoskeleton 1010 to tear apart, facilitating removal of the exoskeleton 1010.

Figure 33:
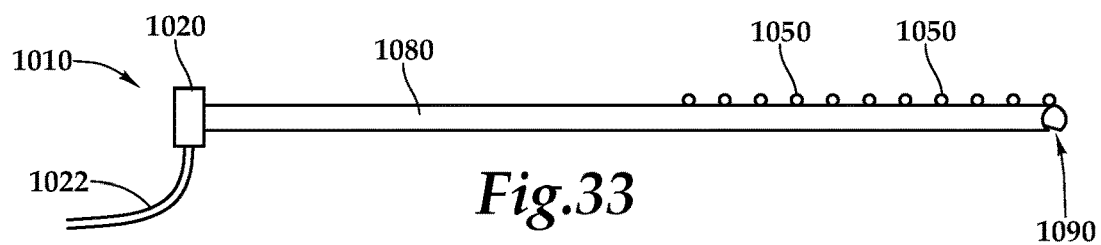
FIG. 33 is a front elevation view of an alternative embodiment of that which is shown in FIG. 28, in the form of a jacket with a slot having a continuous cross-sectional form, rather than the individual splines, and with sensors located upon this jacket.

In FIG. 33 an embodiment of exoskeleton 1010 is depicted where sensors 1050 are provided upon a generally tubular jacket 1080 which is open at a lower slot 1090 shown on an underside thereof. Such a jacket 1080 can be formed of resilient material and snapped onto the lead, or can have the lead snapped out of such a jacket when it is desired to move the lead out through the bottom slot 1090. In the embodiment depicted, the jacket 1080 circumscribes about ¾ of a circumference, so that the slot 1090 has a width similar to a diameter of the lead, with a slight friction fit as the lead snaps into and out of the jacket 1080 through the slot 1090.

Figure 34:
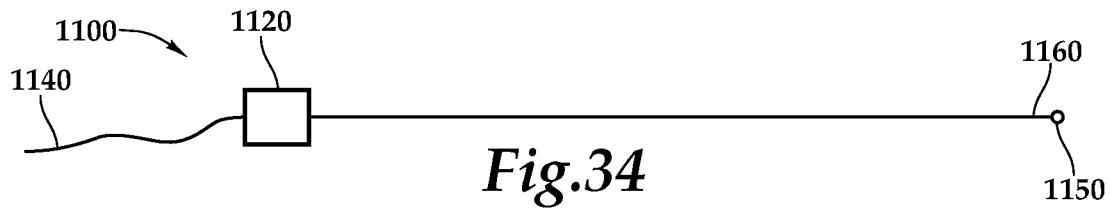
FIGS. 34-36 are front elevation views of a stylet for placement within other interventional devices, or navigation wires fitted with various arrays of sensors near distal tips thereof for visualization on the EP mapping system.
Figure 35:
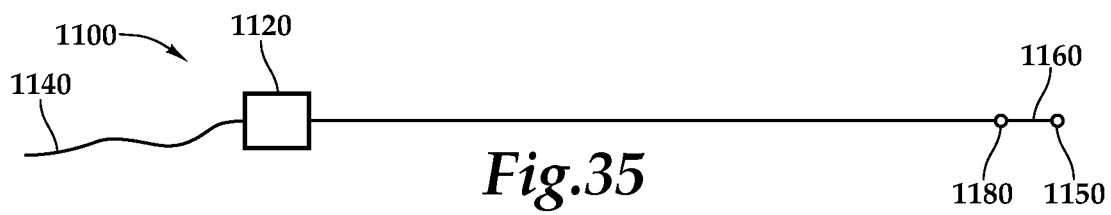
Figure 36:
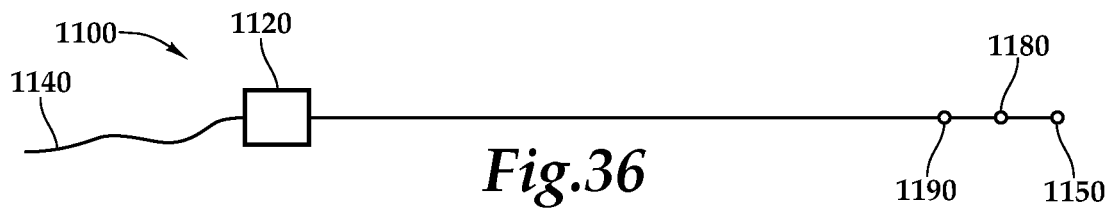

FIGS. 34-36 depict interventional devices in the form of thin elongate wires. These structures can either be navigation wires or stylets 1100. Stylets 1100 differ from navigation wires in that stylets 1100 are typically utilized through an interior of a tube, such as a catheter, tube of a sheath, lumen associated with a cardiac lead, or other tubular structure, while navigation wires are generally used separately without such a surrounding tubular structure.

The stylets 1100 each include a base 1120 with a cable 1140 extending from the base 1120 to an EP mapping system 2. The stylet itself extends from the base 1120 to a tip 1160. A sensor 1150 is provided at this tip 1160. In various embodiments, second sensor 1180 and/or third sensor 1190 can be provided. Sensors 1150, 1180, 1190 are preferably spaced a constant distance apart to allow for visualization of the location of the stylet 1100 with the EP mapping system 2.

Figure 37:
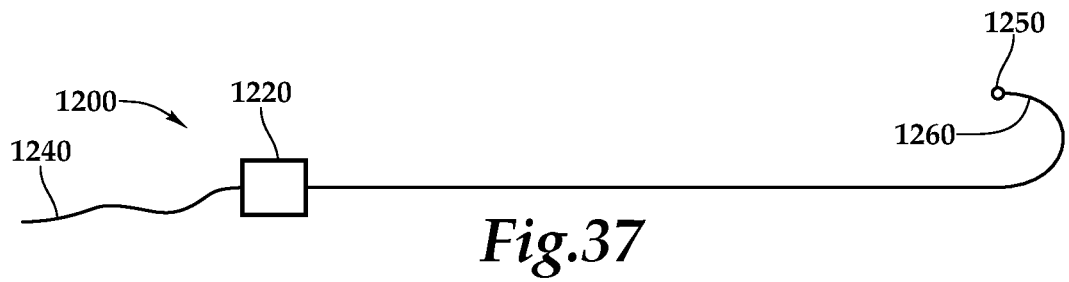
FIGS. 37-39 are front elevation views of stylets or navigation wires similar to those depicted in FIGS. 34-36, but with a curved tip and with various different numbers of sensors located near a distal end of these curved tip navigation wires.
Figure 38:
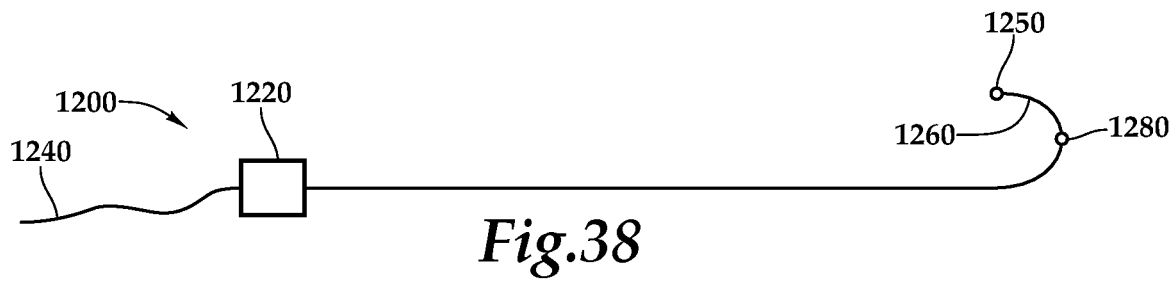
Figure 39:
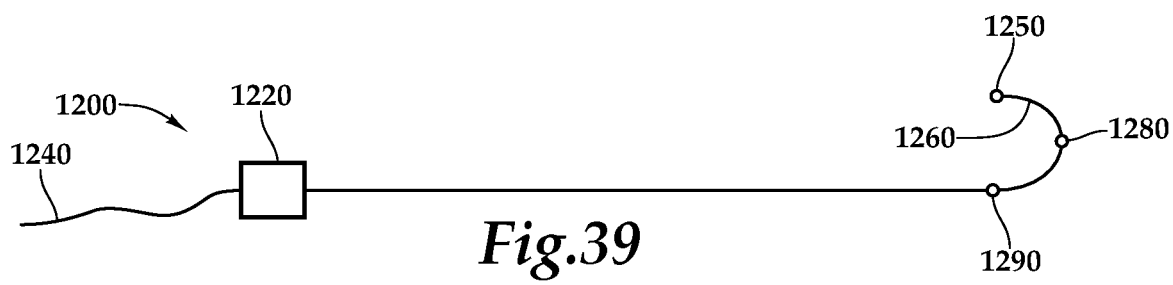
Figure 48:
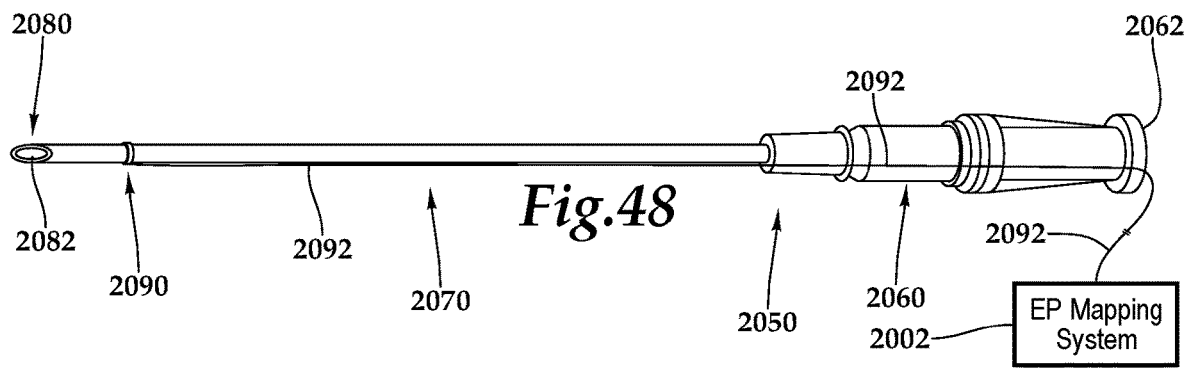
FIG. 48 is a perspective view of a percutaneous needle having one electrode thereon spaced from a tip of the needle, and with the tip of the needle also acting as an electrode for sensing of position and orientation of the percutaneous needle relative to patient anatomical structures upon a display of an EP mapping system.

FIGS. 37-39 show further stylets 1200 which feature pre-formed curved tips 1260 on ends thereof opposite a base 1220. A cable 1240 extends from the base 1220 to the EP mapping system 2. The curved tip 1260 includes a sensor 1250 at a tip thereof. In related embodiments, a second sensor 1280 and third sensor 1290 can be provided at uniform spacing, and typically along the curve adjacent to the tip 1260. The curved tip 1260 of the curved stylet 1200 can thus be seen through the EP mapping system 2.

With particular reference to FIG. 40, details of a connector for a multiple interventional device support tool are described. An interface connector 1300 is provided with a cable 1340 leading to the EP mapping system 2. A stylet coupling 1350 is connected to this cable 1340, as well as to a clip 1370 which can be connected directly to a coronary lead. Various devices, such as base 1120 of a stylet 1110 can be coupled, such as along arrow E to the coupling 1350. Other interventional devices, such as sheaths, dilators, guide wires, J-wire, or luminal catheters, which are fitted with electrodes, can alternatively be coupled, along arrow E, to the coupling 1350 of this interface 1300. A wire 1360 also extends to the stylet 1120 or other tool which is being connected.

With this removable interface 1300, it is not required that separate interventional devices be removed from and reattached to the EP mapping system 2 in an ad hoc fashion. Rather, the removable interface 1300 is wired to the EP mapping system 2, and each of the interventional devices, such as sheaths 910, exoskeletons 1010, stylets 1100, 1200, guide wires 1400, dilators 1600 and catheters 1800 can be configured to plug into and out of the coupling 1350 of the removable interface 1300, for quick and easy substitution of the interventional devices through a common interface and common standard, so that the EP mapping system 2 does not require any special reconfiguring to switch from taking input from one interventional device to take input from another interventional device.

With particular reference to FIGS. 41 and 42 details of various guide wires with EP mapping are closed. In FIG. 41 a basic navigation wire 1400 is provided. A cable 1440 extends back to the EP mapping system 2. Sensors 1450 are provided on this navigation wire 1400 which can be visualized through the EP mapping system 2. The sensors 1450 are generally concentrated adjacent to the tip 1460, so that the tip 1460 in particular can have its location and orientation most effectively visualized.

In FIG. 42, a variation dual navigation wire 1500 is disclosed. In some instances, separate lead wires need to be routed to separate coronary structures, such as two different chambers in the heart H. With the guide wire 1500 a main wire body 1510 is fitted with sensors 1550. A secondary wire body is provided parallel with the main wire body 1510 which is connected by thin elements together to a sensor at a distal tip beyond the sensor 1550. Each wire is connected by a separate cable 1540, 1545 back to the EP mapping system 2. The main wire travels adjacent to the left ventricular lead while the second wire is with in the lumen of the left ventricular lead. The main wire houses the sensors while the secondary wire is very thin except at the opposite end which is stiffer to allow for back loading into the left ventricular lead. The entire double wire is been moved as a single unit to cannulate the desired coronary sinus branch. Once cannulated, the left ventricular lead is advanced over the secondary wire similar to a "buddy wire" technique. The thicker portion of the secondary wire is cut by the operator at the proximal end of the lead, and the main wire body is removed from the patient, along with the very thin secondary wire from the lumen of the left ventricular lead. This design allows for less space constraints for the magnetic sensor(s) or electrodes.

With particular reference to FIG. 44, details of a dilator 1600 are disclosed which include sensors thereon for use with an EP mapping system 2. The dilator 1600 includes a distal tip 1630 with multiple sensors 1650 adjacent to the tip 1630. A base 1610 is provided at a proximal end, with a cable 1620 extending to the EP mapping system 2. The dilator 1630 can in one embodiment have a central tunnel through which a guide wire can pass. in another embodiment, the dilator 1600 is configured to pass through an interior of a sheath such as the sheath 910, or through other catheters or tubular structures, all the while providing position for the dilator 1600 due to the sensors 1650 placed thereon, interacting with the EP mapping system 2.

In FIG. 44 a J-wire 1700 is disclosed with a sharply curved distal end 1760 having at least one sensor 1750 thereon, and with at least one other sensor a known distance away from the sensor 1750 at the distal tip 1760. A cable 1720 extends from the J-wire 1700, leading back to the EP mapping system 2. The EP mapping system 2 can thus display the position of the J-wire 1700 due to interaction of the sensors 1750 with the EP mapping system 2.

FIGS. 45-47 show three different variations of luminal catheters 1800 having distal tips 1860 having different curvatures associated there with. Multiple sensors 1850 are provided at this curving distal end 1860 of these different variations on the luminal catheters 1800. A cable 1820 connects to the luminal catheters 1800, which is electrically coupled to the sensors 1850 and leads back to the EP mapping system 2. The sensors 1850 allow the luminal catheter 1800 to have at least it's curving tip visualized on the display 8 of the EP mapping system 2. Sensors 1850 could also be provided along other portions of the luminal catheters 1800 for more complete visualization if desired.

The invention disclosed herein is further described in use, following this exemplary protocol:

1. Extrathoracic electrode or magnetic patches and magnet is placed around the patient based on cardiac electrophysiology mapping systems.

2. Cardiac and extra-cardiac structures can be visualized by multiple means and loaded into the cardiac electrophysiology mapping system without necessarily the need for placement of intracardiac catheters.
   a) Transthoracic echo equipped with magnetic sensor or electrodes can visualize cardiac structures, blood vessels, and extracardiac structures, which can be interfaced with the cardiac electrophysiology mapping system. Details of such technology are described in the inventor's co-pending U.S. patent application Ser. No. 15/813,717, filed on Nov. 15, 2017, incorporated herein by reference in its entirety.
   b) A posterior-anterior fluoroscopy image could be loaded into the cardiac electrophysiology mapping system.

Since there are multiple fluoroscopic vendors, a common format could be utilized such as JPEG provided by the fluoroscopic system, or a camera can take a picture of the fluoroscopic video display, which can be downloaded into the mapping system. A PA view in the EP mapping system can be matched to the fluoroscopic image and can be "locked" into a PA map (where the angle of view cannot be changed on this particular map), and landmarks such as the clavicle and subxiphoid process can be used for reference. A reusable magnetic sensor can be placed at various reference locations to size the image to the locked view PA file. This would create a familiar image for the cardiac electrophysiologist to navigate the magnetic sensor mounted stylets in the pacing or ICD leads into the cardiac structure.

A fluoroscopic image taken from a camera can be loaded into the mapping system. This view can be matched and locked into the mapping system. The fluoroscopic background gives the cardiac electrophysiologist a familiar visual reference, without needing to activate the fluoroscope. If a high quality camera is utilized, any fluoroscopic vendor could be used, and will be familiar to each individual operator. This technology exists in current mapping systems. If radiation exposure was of less concern, CT scan dicom file can be loaded and various land marks could be used to tag the subclavian vein, superior vena cava and concerned cardiac structures.

3. Venous access can be obtained with or without the assistance of the cardiac electrophysiology mapping system. The usual practice is to obtain venous with minimal or no use of fluoroscopy. A transthoracic echo equipped with a magnetic sensor/electrodes or CT scan can visualize salient venous structures for the cardiac electrophysiology mapping system. A magnetic sensor or electrode mounted needle could be used to directly visualize the entrance of the needle into the intravascular space using the cardiac electrophysiology mapping system. Venous access can be confirmed with the magnetic sensor J-wire, or a traditional J-wire using fluoroscopy can be utilized. A dilator and sheath is placed over the J-wire which can be equipped with a magnetic sensor or electrodes. However standard sheaths could also be utilized.

4. Permanent pacing leads or defibrillators leads with magnetic sensor mounted stylet, with electrodes connected to the mapping system could be directly visualized as it travels through the vascular tree and navigated to various locations in the right atria or right ventricle.

5. The stylets can be shaped and replaced to steer the permanent pacing/ICD lead to the desired location which is visualized using the cardiac electrophysiology mapping system.

6. Once leads are in place, leads are deployed, and stylets are removed. Standard technique is used to secure the device and leads.

7. For placement of a coronary sinus lead:
a) Once vascular access obtained, a standard EP catheter can be used to cannulate the coronary sinus. This could also be a catheter equipped with a magnetic sensor (but without ablation capabilities) to establish a matrix around the coronary sinus.
b) Sheath with magnetic sensor or electrodes are placed over the EP catheter and into the coronary sinus.
c) Usual practice is to visualize the coronary sinus tree by injecting radio contrast into the sheath under fluoroscopy. Using the standard left anterior oblique view of the heart, branch vessels of the coronary sinus can be visualized. A JPEG file can be made of the desired image, and transferred to the EP mapping system either by direct communication or by a high resolution camera. The matching view in the electrophysiology mapping system and the fluoroscopic image can be "locked" together into a map (where the angle of view cannot be changed on this particular map). Sizing can be used by calibrating the EP catheter and coronary sinus sheath to the fluoroscopic image. Standard EP catheters, magnetic sensor mounted sheaths, luminal catheters, magnetic sensor mounted stylets within permanent leads and magnetic sensor mounted coronary sinus wires could be visualized on this "locked" two dimensional map in the cardiac electrophysiology mapping system with the background of the fluoroscopic image.

An image of a catheter within the coronary sinus can be imported into a cardiac electrophysiology mapping system, and this view locked in place. This allows for the coronary sinus wire to be fed into the selected branch without the need for active fluoroscopy. A coronary sinus catheter is visualized in place which can have mounted electrodes or magnetic sensor, which will show the location of the tip as it is maneuvered within the coronary sinus in the EP mapping system, with the locked image as a background. A coronary sinus wire mounted with an electrode or magnetic sensor is also visualized on the EP mapping system with the locked image as a background. The left ventricular lead is visualized since the electrodes are also visualized by the EP mapping system.

i. Luminal catheter with magnetic sensor or electrodes can sub-select a desired branch using the cardiac electrophysiology mapping system.

ii. Desired branch is cannulated with the magnetic sensor mounted coronary sinus wire.

iii. Left ventricular pacing lead is placed over the coronary sinus magnetic sensor mounted wire and into the desired coronary sinus branch. All sheaths and coronary sinus wire removed from the patient by a slitter, which can be oriented to run parallel with the coronary sinus sheath. Coronary sinus pacing lead secured using standard techniques.

For "leadless" pacemakers, which are placed by the femoral vein, a catheter mounted with either electrodes or magnetic sensor can be utilized to visualize the location of the catheter using a cardiac electrophysiology mapping system.

Figure 67:
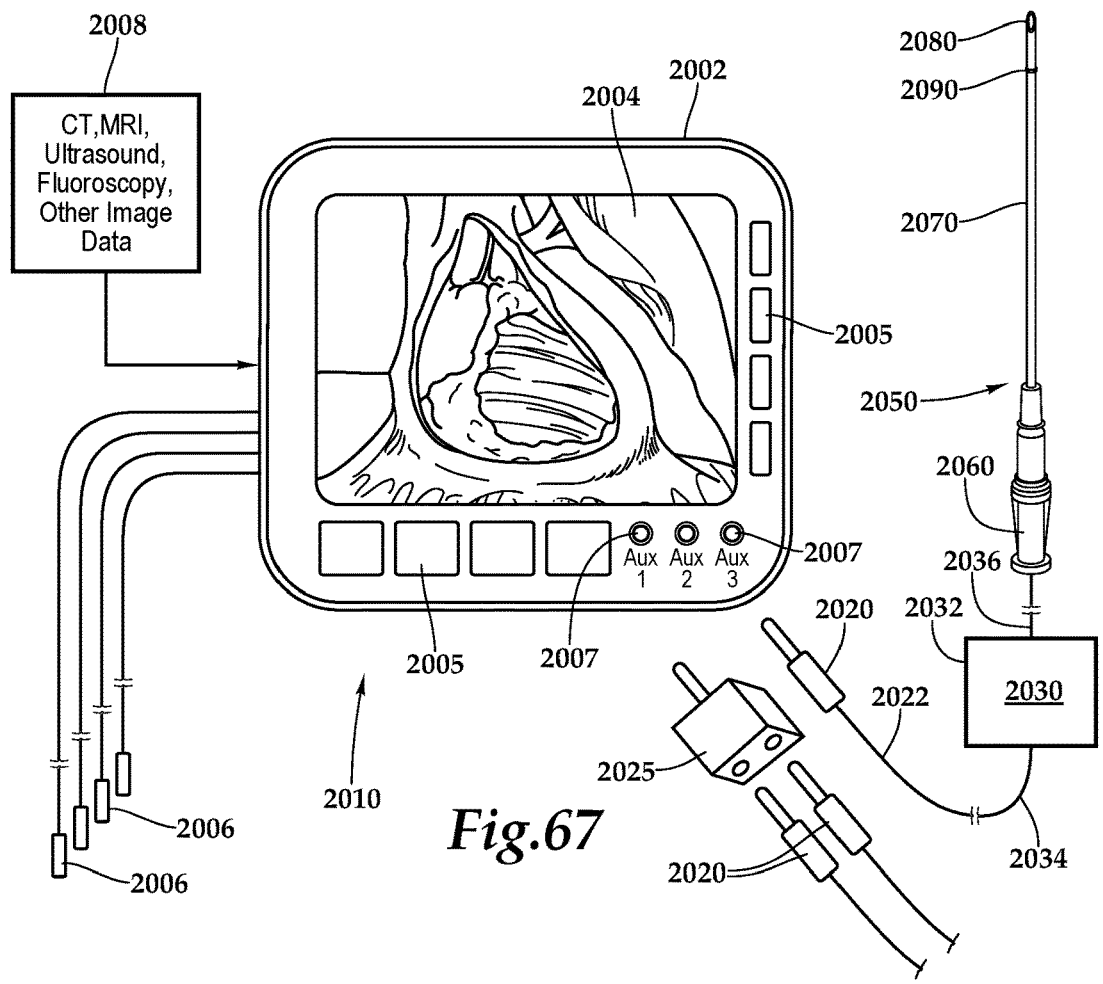
FIG. 67 is a schematic depiction of an EP mapping system and associated display and showing how a module such as a percutaneous needle module can be coupled to the EP mapping system for display of the items associated with the module on the display of the EP mapping system.
Figure 68:
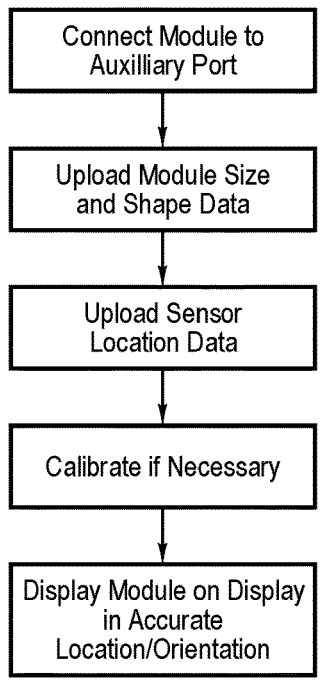
FIG. 68 is a flow chart identifying steps in the process of using the EP mapping system with subcutaneous interventional equipment items associated with a module coupled to the EP mapping system.

With particular reference to FIGS. 67 and 68, a modular approach to integration of items of subcutaneous interventional equipment with an EP mapping system 2002 are described, according to an alternative embodiment. In this embodiment, the EP mapping system 2002 includes a display 2004 where patient anatomical structures can be visually depicted. In this embodiment, buttons 2005 are provided, such as for adjustment of the display or otherwise operating the EP mapping system 2002. Electrodes 2006 couple to different portions of the patient's body, which can also be in the form of other sensors, such as magnetic field sensors, which are appropriately placed adjacent to the body of the patient so that the anatomically correct visualization appears on the display 2004 of the EP mapping system 2002. Data from other imaging systems 2008 can also be integrated into the EP mapping system 2002.

Figure 69:
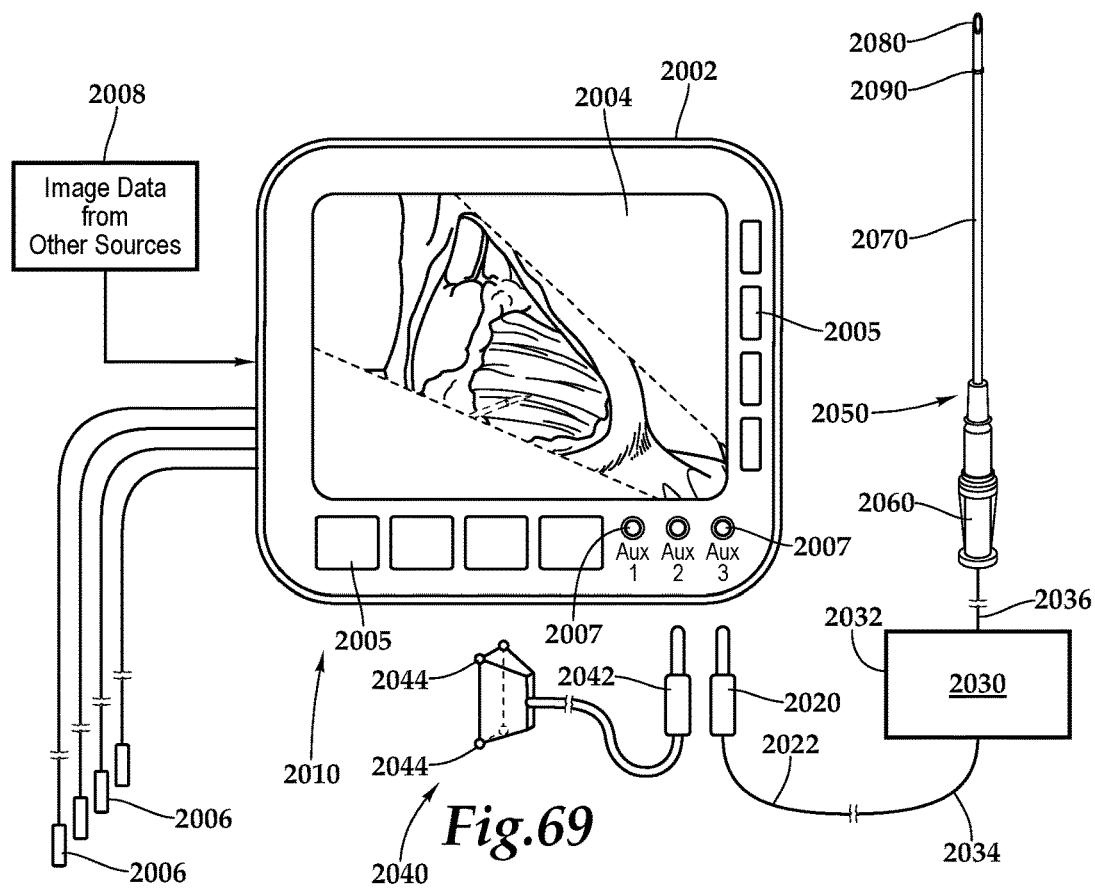
FIG. 69 is a schematic depiction similar to that which is shown in FIG. 67, but further including transthoracic ultrasound therewith.

With this invention further interfaces are provided, such as in the form of multiple auxiliary ports 2007. These auxiliary ports 2007 are configured so that a module can be coupled thereto. Such coupling would occur in this embodiment through a connector 2020 having a cable 2022 or other wire leading to other portions of the module. A typical module would be some item of subcutaneous interventional equipment. In FIG. 69 this module is depicted as including a percutaneous needle 2050 having a hub 2060 supporting a shaft 2070 extend to a tip 2080, and with at least one electrode 2090 mounted on the shaft 2070.

For the EP mapping system 2002 to be able to accurately display the item of subcutaneous interventional equipment, such as the percutaneous needle 2050, details about the item are required. These details typically include one or more of the shape of the item, the size of the item, where the electrode 2090 or other sensor is located upon the item, and potentially other details (such as which portions of the item are most important to display). The electrode 2090 or other sensor on the percutaneous needle 2050 or other item of subcutaneous interventional equipment is used along with the EP mapping system 2002 to measure impedance relative to other electrodes 2006 within the EP mapping system 2002. Such impedance that is sensed can be used as is known with EP mapping system technology, to identify a location of the percutaneous needle 2050 or other item of subcutaneous interventional equipment.

With multiple electrodes 2090 or other sensors, two points on the item, such as the percutaneous needle 2050, can be identified and visualized adjacent to anatomical structures. Knowing the spacing between the electrodes, and other details such as the distance from the electrode 2092 to the tip 2080, allows for the location of the tip 2080 to be determined relative to anatomical structures. Furthermore, with the module containing information such as shape and size information for the percutaneous needle 2050 or other item of subcutaneous interventional equipment, the entire item, such as the percutaneous needle 2050, can be depicted with accurate position, orientation, size and shape. Some of this information can be derived by the EP mapping system 2002 based on the position of the electrodes 2090 or other sensors, and some of this information can be provided from a collection of information stored within the module and associated with the particular item, such as the percutaneous needle 2050. This stored relevant data associated with the percutaneous needle 2050 or other item within some alternative module, is preferably stored within a tool specific details repository 2030 located within the module, such as between the connector 2020 and the percutaneous needle 2050 or other item within the module. As an alternative, such data could be preloaded into the EP mapping system 2002 or could be provided from some other source, such as an online internet database of such information.

According to one embodiment of this invention, when utilizing an item of subcutaneous interventional equipment associated with a module, this module is first connected to the EP mapping system by placement of the connector 2020 into one of the auxiliary ports 2007 or otherwise interfacing the item with the EP mapping system 2002. Various data from the module and associated with the item of subcutaneous interventional equipment is uploaded into the EP mapping system 2002. The EP mapping system 2002 can then utilize at least one electrode 2090 or other sensor, along with the electrodes 2006 or magnetic field associated with the EP mapping system 2002, and (through impedance measurements and/or magnetic field intensity measurements) identify location data for the electrode 2090 or other sensor (or sensors) relative to other anatomical structures sensed by the EP mapping system 2002.

In one embodiment, a calibration step can be included, such as by placing a tip or other portion of the item at a known location relative to the patient, to determine if the EP mapping system 2002 is accurately placing this tip relative to patient anatomical structures on the display 2004. If a variance is detected, calibration can occur to eliminate this variance. If no variance is detected, confirmation is provided to the operator that the system is properly calibrated.

As one example, the tip of a percutaneous needle, after penetrating the skin, could be brought adjacent to a known distinctive portion of a bone adjacent to where the needle passes through the skin of the patient. This known anatomical location on the particular bone of the patient would be visualized on the display 2004 of the EP mapping system 2002. If the tip of the percutaneous needle 2050 is shown on the display 2004 directly adjacent to the known anatomical detail of the bone of the patient, the system is properly calibrated, and the operator has confidence that the tip is actually located where the EP mapping system is displaying the tip.

If a variance exists, the operator can select the calibrate button (and select the proper position for the tip on the display), and the EP mapping system 2002 will adjust to the position of the percutaneous needle 2050 or other item to be displayed, with the tip 2080 touching the known anatomical structure on the bone of the patient. Further calibration steps can be executed until reliable accurate results are being returned, so that the highest level of confidence can be provided that the item of subcutaneous interventional equipment is actually located where it is being depicted by the EP mapping system 2002. The item can then continue to be used with confidence in performing the interventional procedure for which the item is to be used. This interventional procedure can be guided by the medical professional viewing the display 2004 of the EP mapping system 2002. Exposure of the patient and medical professionals to nuclear radiation is avoided while the navigational guidance is provided.

Figure 70:
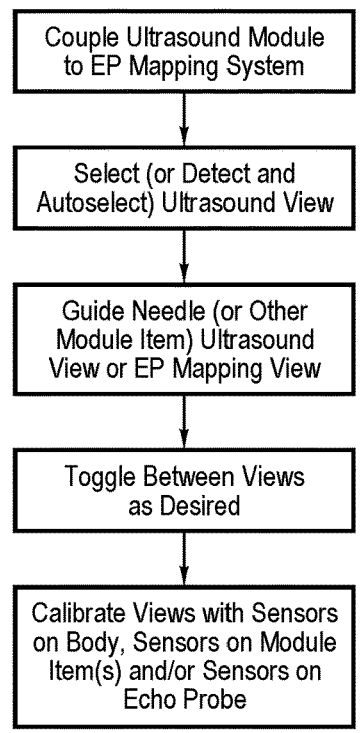
FIG. 70 is a flow chart of steps associated with use of the EP mapping system with transthoracic ultrasound and other modules including items for subcutaneous intervention, usable together with the EP mapping system.

In a variation of this EP mapping system 2002 depicted in FIGS. 69 and 70, the system is further augmented by utilization with a transthoracic echo probe including an ultrasound module 2040. This module 2040 is configured with a connector 2042 which can be coupled to one of the auxiliary ports 2007 on the EP mapping system 2002 as well as sensors 2044, typically in the form of electrodes (or magnetic field sensors) on known portions of the ultrasound module 2040. Other items of interventional equipment associated with other modules can be simultaneously coupled to other auxiliary ports 2007 of the EP mapping system 2002 (or through an adapter 2025, such as shown in FIG. 67).

The ultrasound module 2040 can provide for further calibration, in that it can provide further visualization utilizing ultrasound echo probe technology. In one embodiment, at least one of the buttons 2005 associated with the EP mapping system 2002 can be selected so the display 2004 changes from depicting typical EP mapping system images to displaying typical echo probe images from the echo probe module 2040. This can be done simultaneous with utilization of another module, such as a module including a percutaneous needle 2050, so that needle 2050 location can be verified with the ultrasound module 2040 simultaneously and utilizing the display 2004 of the EP mapping system 2002. Calibration between data from the echo probe 2040 and from other portions of the EP mapping system can occur separately from or simultaneously with calibration of position of the percutaneous needle 2050 or other items associated with some other module also coupled to the EP mapping system. Such an echo probe module 2040 also allows for potential accurate display of information in an EP mapping system without requiring an intra-cardiac electrode to be placed within the heart of the patient, or otherwise requiring a complex interventional procedure nearby to place electrodes for operation of the EP mapping system. Utilization of such an echo probe module 2040 along with the mapping system 2002 is further disclosed in co-pending U.S. patent application Ser. No. 15/813,717, filed on Nov. 15, 2017, incorporated herein by reference in its entirety.

The process of utilizing such an ultrasound module 2040 along with EP mapping system is disclosed in the flowchart of FIG. 70 including coupling of the ultrasound module 2040 to EP mapping system 2002, and a step of selecting the display for EP mapping system 2002 to display either EP mapping data or ultrasound data. The percutaneous needle 2050 or other item of subcutaneous interventional equipment can also be attached to the EP mapping system 2002, and, typically after calibration, can be utilized either with an ultrasound module or an EP mapping system view on the display 2004 of EP mapping system 2002. If desired, views can be toggled back-and-forth between EP mapping system views and ultrasound echo probe views as desired by the operator.

With particular reference to FIGS. 48-66 and 71-78, various different items are disclosed which define examples of subcutaneous interventional equipment suitable for having a module configured so that the items can be coupled to the EP mapping system 2002 for utilization therewith as discussed above. In FIGS. 48-51 the percutaneous needle 2050 described above with regard to FIGS. 67 and 69 is further described. This percutaneous needle 2050 typically has a configuration similar to that known in the prior art, with the modification that it is configured to include at least one electrode 2090 near a tip 2080 thereof. The tip 2080 thereof itself also acts as an electrode. A wire 2092 extends from the electrode 2090, and wiring typically also is electrically coupled to the tip 2080, such as through the shaft 2070 all formed together with the tip 2080 of an electrically conductive substance, for connecting back to other portions of the module (FIGS. 67 and 69) and through the connector 2022 EP mapping system 2002.

In one embodiment, this needle 2050 includes a hub 2060 with a valve at a proximal end of the hub 2060. This valve 2062 allows for a stylet (or catheter or guide wire or other structure) to be passed therethrough if desired. A syringe can optionally also be coupled to this valve 2062 should fluid introduction through the tip 2080 of the needle 2050 be desired. Various other items could also optionally be passed through the needle 2050 from the valve 2062 to the tip 2080.

The needle 2050 with the shaft 2070 typically includes at least one layer of insulation to electrically isolate the inner tube of the shaft 2070 from wires 2092 extending from the electrode 2090. If the inner tube of the shaft 2070 is formed of an electrically non-conductive material, some of this installation can be avoided. If the wire 2092 carries its own insulation, such as in the form of an installation jacket on the wire 2092, some of this installation can be avoided. If multiple electrodes are included on the needle 2050, multiple layers of insulation can be provided or the wires routed to avoid each other.

Figure 49:
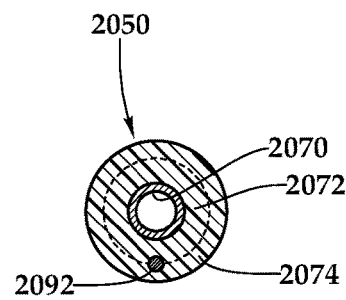
FIG. 49 is a sectional view of a shaft of the needle of FIG. 48 and showing positions of inner and outer insulation surrounding a shaft of the needle, and as well as a wire coupled to the electrode.
Figure 50:
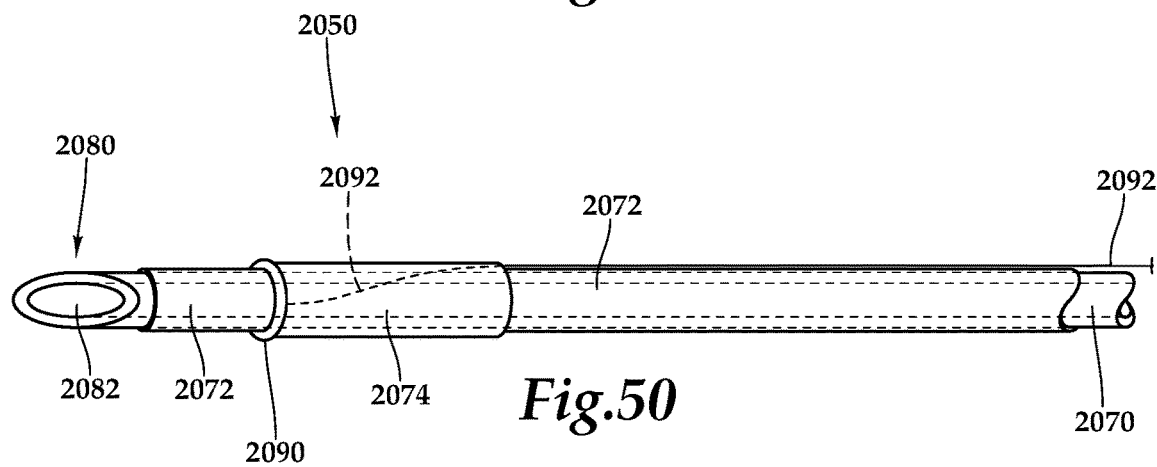
FIG. 50 is a perspective view of a detail of a portion of that which is shown in FIG. 48, with portions of the outer insulation cutaway and with portions of the inner insulation cut away, in one embodiment of that which is shown in FIG. 48.
Figure 51:
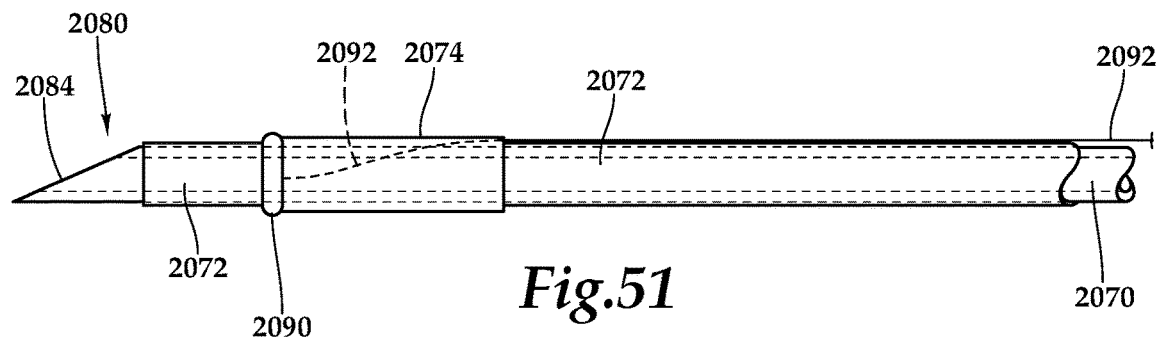
FIG. 51 is a front elevation view of that was shown in FIG. 50.
Figure 52:
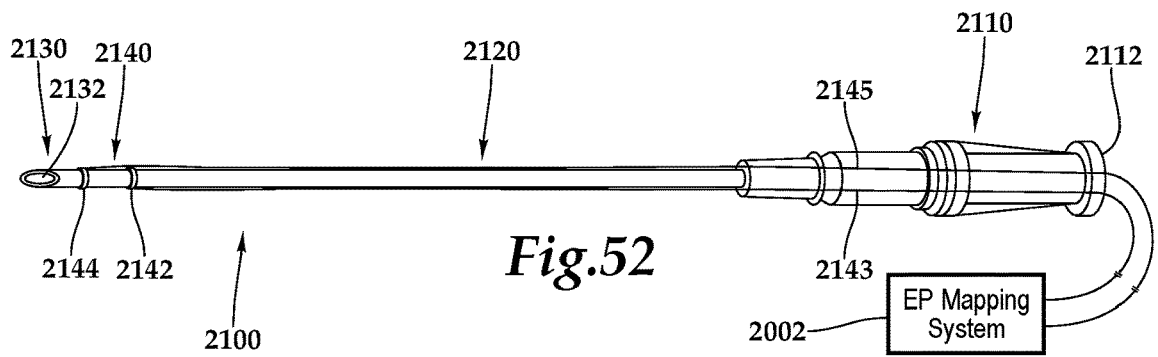
FIG. 52 is a perspective view of a percutaneous needle having a pair of electrodes thereon spaced for a tip of the needle, and with the needle coupled to an EP mapping system for visualization of position and orientation of the needle thereon.
Figure 53:
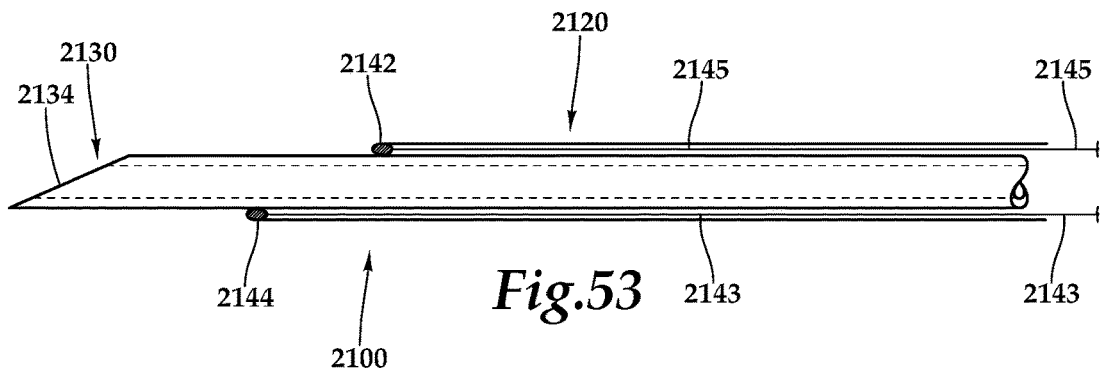
FIG. 53 is a front elevation view sectional detail of that which is shown in FIG. 52, for the showing position of electrodes and wires leading from electrodes relative to a tip of the needle of FIG. 52.
Figure 54:
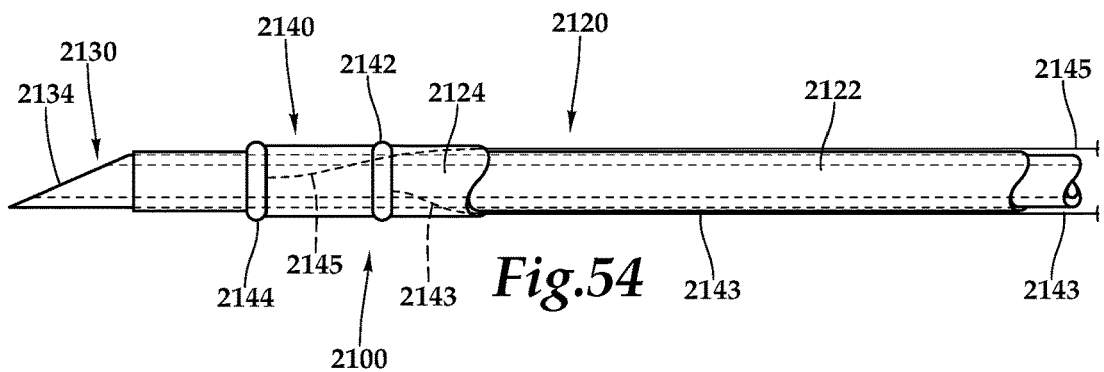
FIG. 54 is a front elevation view of that which is shown in FIG. 53, with different portions thereof cutaway relative to FIG. 53.
Figure 55:
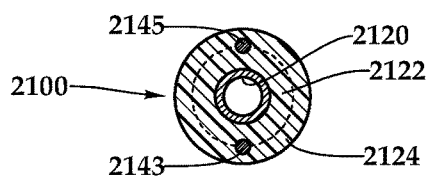
FIG. 55 is an end sectional view of that which is shown in FIG. 54 revealing how insulation and wires coupled to electrodes are configured relative to the shaft of the needle of FIG. 54.
Figure 56:
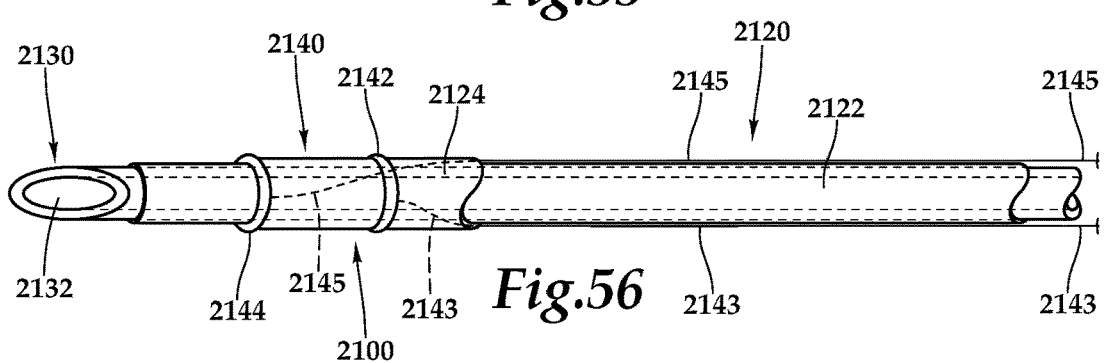
FIG. 56 is a perspective view of a tip portion of that which is shown in FIG. 52, with portions of the outer insulation and inner inflation cut away to reveal details thereof.
Figure 57:
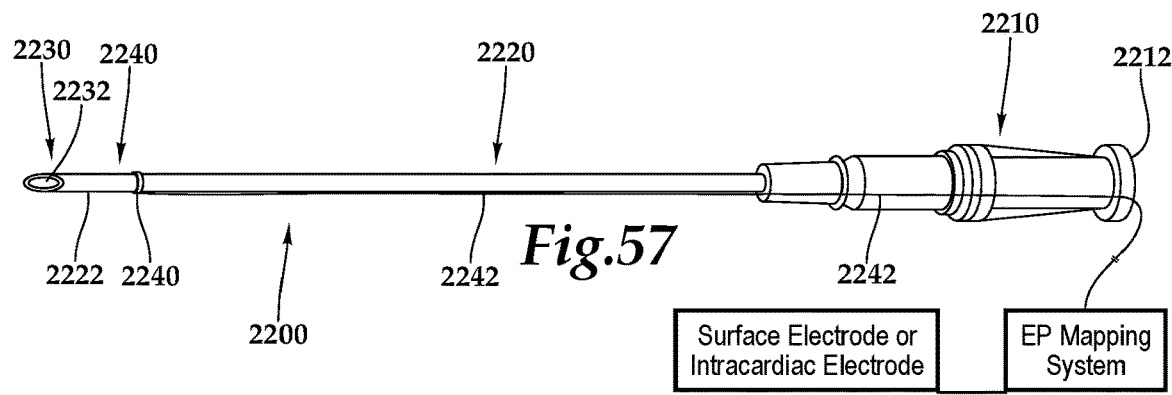
FIG. 57 is a perspective view of a percutaneous needle fitted with a unipolar electrode and with the needle coupled to an EP mapping system for visualization of position and orientation of the needle therein.
Figure 58:
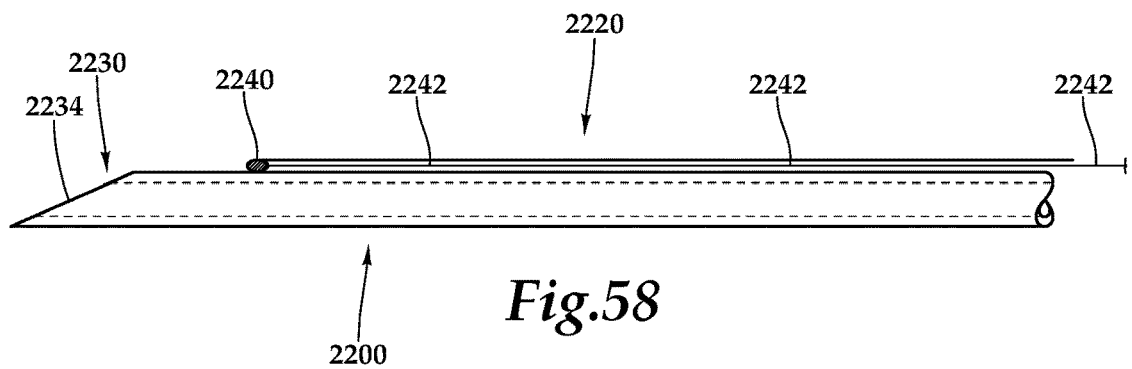
FIG. 58 is a front elevation view of a portion of that which is shown in FIG. 57, with portions of the insulation cut away to reveal electrode and wire details.
Figure 59:
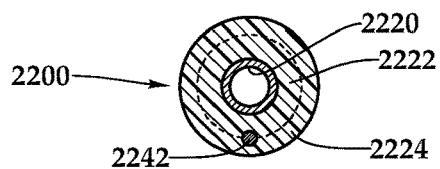
FIG. 59 is a full sectional end view of that which is shown in FIG. 57, revealing a position of inner and outer layers of insulation relative to the shaft of the needle and a wire extending from the electrode.
Figure 60:
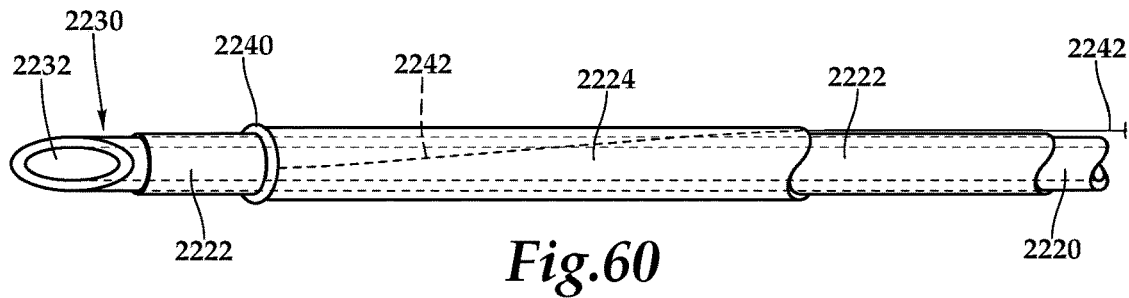
FIG. 60 is a perspective view of that which is shown in FIG. 58 and with portions of the insulation cut away.
Figure 61:
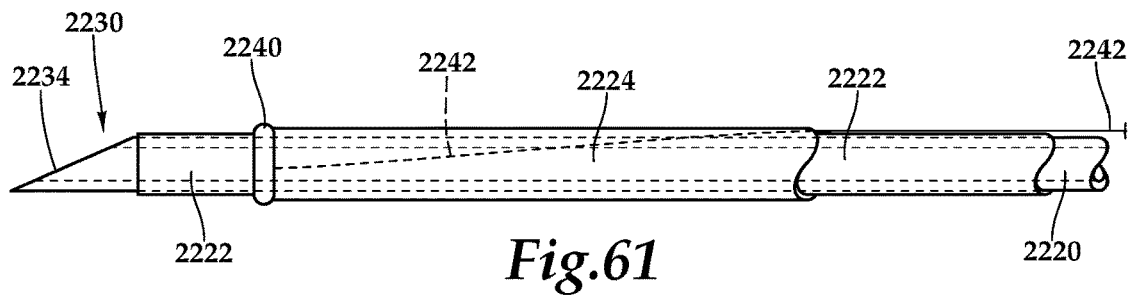
FIG. 61 is a front elevation review of that which is shown in FIG. 60.

In this FIG. 48-51 environment, two layers of insulation are provided including inner insulation 2072 and outer insulation 2074 (separated by the dashed line shown in FIG. 49). A wire 2092 extending to the electrode 2090, is placed between the inner insulation 2072 and the outer insulation 2074. In this embodiment, the electrode 2090 itself is toroidal in shape, so that it can come into contact with adjacent tissues on all sides of the needle 2050. In alternative embodiments, the electrode 2090 could end at a point rather than at such a toroid. The wire 2092 can spiral helically about the shaft 2070 of the needle 2050, but is depicted herein as having a straight path extending from the electrode 2090 back to the hub 2060. In this embodiment, the inner insulation 2072 extends to the distal end stopping just short of the tip 2080 and extends proximally all the way back to the hub 2060. The outer insulation 2074 extends from the electrode 2090 proximally back to the hub 2060. This leaves the tip 2080 exposed and able to function as an electrode by coming into contact with adjacent tissues.

The tip 2080 includes an opening 2082 and bevel 2084. Various different tip 2080 configurations can alternatively be provided as opposed to the beveled tip which is shown. Diameter of the opening 2082 could be greater or smaller. The gauge of the needle 2050 can be greater or smaller as well, affecting a diameter of the tip 2080. The tip 2080 is shown being sharp, such as to facilitate puncturing of the skin and other bodily structures. In alternative embodiments, the tip 2080 could be more blunt, such as to only be able to penetrate the weakest of bodily structures and not damage other structures.

With particular reference to FIGS. 50-56, a percutaneous needle 2100 is disclosed which includes two electrodes 2140 adjacent to a tip 2130 at a distal end of a shaft 2120, extending distally from the hub 2110. The hub 2110 includes a valve 2112 thereon similar to a valve 2062 of the percutaneous needle 2050 (FIGS. 48-51). The shaft 2120 can be configured with installation including inner insulation 2122 and outer insulation 2124. The tip 2130 includes an opening 2132 and bevel 2134. These details of the insulation 2122, 2124 and tip 2130 can we generally similar to those of the needle 2050 (FIGS. 48-51).

Electrodes 2140 include a proximal electrode 2142 and a distal electrode 2144. The proximal electrode 2142 has a wire 2143 associated therewith extending back to the hub 2110. Electrode 2144 has a separate wire 2145 associated therewith extending back to the hub 2110. The wires 2143, 2145 can pass on to the EP mapping system 2002, or can have their signals combined together with some pre-processing before passing on to the EP mapping system 2002. These two electrodes 2142, 2144 are preferably each toroidal, extending circumferentially about the shaft 2120 of the needle 2100. The inner insulation 2122 isolates the electrodes 2142, 2144 from the inner conduit of the shaft 2120 of the needle of 2100. Outer insulation covers the wires 2143, 2145. The wires 2143, 2145 are routed to avoid touching each other by staying on opposite sides of the needle 2100, or can be provided with insulating jackets to prevent electrical contact there between.

With particular reference to FIGS. 57-61, details of a unipolar electrode percutaneous needle 2200 are described, as an alternative to the needle 2050 (FIGS. 48-51). Details of this unipolar electrode needle 2200 match those of the needle 2050 except where specifically distinctly disclosed. A hub 2210 supports a valve 2212 thereon and with a shaft 2220 extending distally from the hub 2210 to a tip 2230. Inner insulation 2222 and outer insulation 2224 is provided on the shaft 2220. A tip 2230 includes an opening 2232 and a bevel 2234. A single electrode 2240 is provided spaced from the tip 2230.

In this embodiment, rather than having the tip 2230 function as an electrode, a separate surface electrode or intracardiac electrode is provided and coupled to the EP mapping system 2002, either through other portions of the EP mapping system 2002 or as part of the module that provides of this unipolar electrode percutaneous needle 2200. Preferably, the inner insulation 2222 keeps electrode 2240 from contacting the electrically conductive portions of the shaft 2220, and the outer insulation 2224 protects the wire 2242 associated with the electrode 2240 or an exterior thereof. Other portions of the EP mapping system 2002 can function as part of the module that provides this unipolar electrode percutaneous needle 2200, such as electrode 2006 (FIG. 67) functioning as the reference electrode. If the wire 2242 is provided with its own insulating jacket, the outer insulation 2224 could be avoided. As another alternative, the electrode 2240 could be just provided with a small amount of the inner insulation 2222 adjacent to the electrode 2240, but not extending significantly along the length of the needle 2200. Insulation adjacent to the electrode 2240 could conceivably be embedded somewhat into the shaft 2220 of the needle 2200, to minimize diameter of the needle 2200. Thus, in this embodiment with much of the insulation 2222, 2224 avoided, a potential for a smaller diameter needle 2200 is provided.

Figure 62:
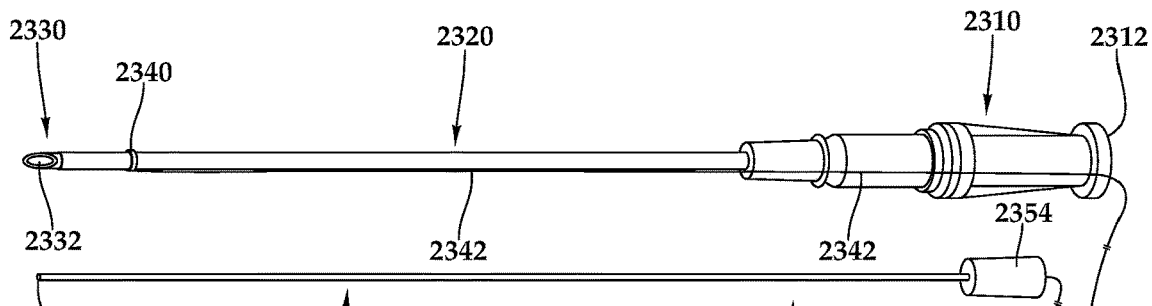
FIG. 62 is a perspective view of a percutaneous needle and associated electrode stylet which can fit through a hollow center of the shaft of the needle and extend out the tip of the needle so that the stylet provides one electrode of a two electrode positioning system for this percutaneous needle, and with one electrode on the needle shaft spaced from the tip, the needle coupled to an EP mapping system for visualization thereon.
Figure 63:
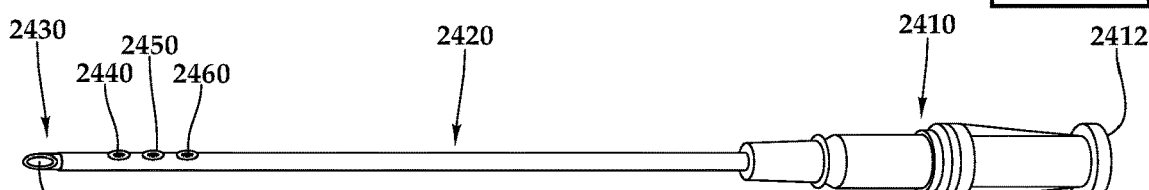
FIG. 63 is a perspective view of a percutaneous needle having a set of magnetic field sensors located thereon for use in proper positioning and orienting of the needle within an EP mapping system.
Figure 64:
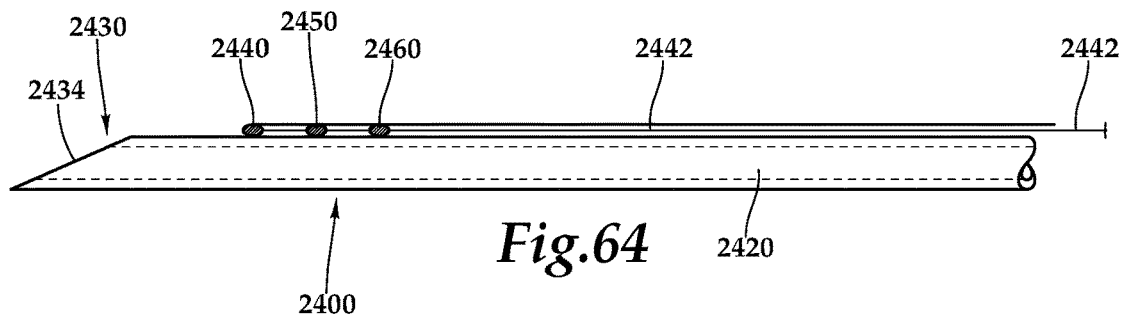
FIG. 64 is a front elevation view of a tip portion of that which is shown in FIG. 63, with portions thereof cut away to reveal details of the magnetic field sensors and at least one wire extending therefrom for interfacing with an EP mapping system.
Figure 65:
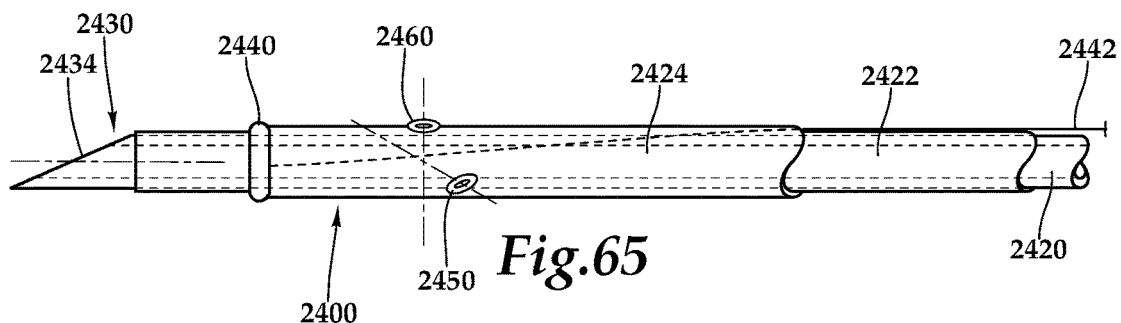
FIG. 65 is a front elevation view of that which is shown in FIG. 64 and with the set of magnetic field sensors in the form of three sensors oriented in three mutually perpendicular orientations according to one embodiment of this invention.

With particular reference to FIG. 62, details of a single electrode percutaneous needle system 2300 are disclosed, according to an alternative embodiment. In this system 2300, a needle portion including a hub 2310, shaft 2320 and tip 2330, as well as electrode 2340 are similar to those depicted in FIG. 48 with regard to the needle 2050. However, rather than having the tip 2330 act as a second electrode, a stylet 2350 is provided which can pass through the valve 2312 in the hub 2310, through the shaft 2320 and out of the tip 2330. This stylet 2350 extends from its own hub 2354 to a tip 2352.

The shaft 2320 is preferably formed of an electrically conductive material. Examples include plastic, ceramic, carbon fiber, or other non-electrically conductive material. A tip 2352 of the stylet 2350 sticking out of the needle 2330 acts as a second electrode along with the electrode 2340. A line 2360 associated with the stylet 2350 and a line 2342 of wiring for the electrode 2340 are both fed back to the EP mapping system 2002 so that positional information can be provided. At least some of the insulation on the shaft 2320 can be dispensed with when the shaft 2320 is formed of a non-electrically conductive material, and when the wire 2342 includes an insulating jacket thereon. Without any such insulation, the potential for a thinner needle within the system 2300 is provided.

With particular reference to FIGS. 63-66, details of a percutaneous needle 2400 are described in an embodiment where sensors associated therewith are not in the form of electrodes, but rather in the form of magnetic field sensors. The needle 2400 includes a hub 2410 with a valve 2412 thereon and with a shaft 2420 extending from the hub 2410 to a tip 2430. This tip 2430 includes an opening 2432 and a bevel 2434, or can have other tips as disclosed elsewhere herein. In this embodiment three magnetic field sensors are provided including an X-axis sensor 2440, a Y-axis sensor 2450 and a Z-axis sensor 2460. In one embodiment, these magnetic field sensors are in the form of coils wrapped around central axes aligned with either the X-axis, Y-axis or Z-axis. In one embodiment, these coils are oriented as depicted and FIG. 65, with the X-axis magnetic field sensor in the form of a toroid surrounding the shaft 2420 of the needle circumferentially, and with the Y-axis sensor 2450 and Z-axis sensor 2460 placed on sides of the shaft 2420.

Different layers of insulation 2422, 2424 can be provided as desired to protect and/or isolate these magnetic field sensors 2440, 2450, 2460 and wires associated therewith from the underlying shaft 2420 or other portions of the needle 2400. In this embodiment, a single wire 2440 is shown coupled to the multiple sensors 2440, 2450, 2460. As an option, signals can be sampled from each of the three magnetic field sensors 2440, 2450, 2460 sequentially. Alternately, three separate wires 2442 can be provided as conductors within a single outer covering, or could be three separate wires maintaining spacing from each other or with their own insulating jackets.

Figure 66:
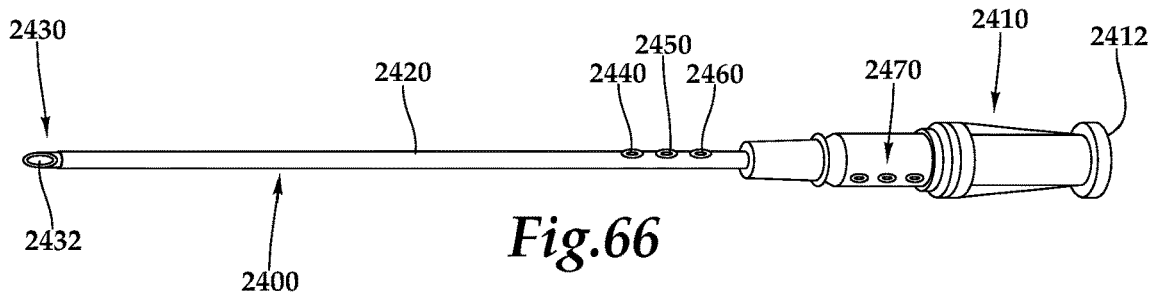
FIG. 66 is a perspective view of that which is shown in FIG. 63 showing various alternative locations for placement of the magnetic field sensors thereon.

As depicted in FIG. 66, while the sensors 2440, 2450, 4260 are preferably placed near the tip 2430, they can actually be placed closer to the hub 2410 or on the hub 2410 itself in the form of a sensor set 2470 on the hub 2410. Data associated with such a needle 2400 would include spacing between the sensors 2440, 2450, 2460 and the tip 2430 of the needle 2400, and spacing from other relevant portions of the needle 2400, so that the tip 2430 can be accurately displayed on the display 2004 of the EP mapping system 2002. Such accurate display can thus occur even with a bare needle 2400 having no sensors other than on the hub 2410. When the sensors are in the form of magnetic field sensors, typically a magnetic field is also provided external to the body of the patient and position within this magnetic field is identified by measurements taken by these sensors 2440, 2450, 2460. With three mutually perpendicular sensors, position and orientation can be accurately identified for proper placement of the needle 2400 or other item within the depiction visualized on the display 2004 of the EP mapping system 2002.

With particular reference to FIGS. 71-78, other items generally in the form of subcutaneous interventional equipment are fitted with sensors, such as in the form of electrodes or magnetic field sensors and configured within a module for coupling to an EP mapping system 2002, both for visualization of the location of the interventional equipment items and also potentially to provide further locations for electrodes 2006 or other sensors to facilitate enhanced operation of the EP mapping system.

Figure 71:
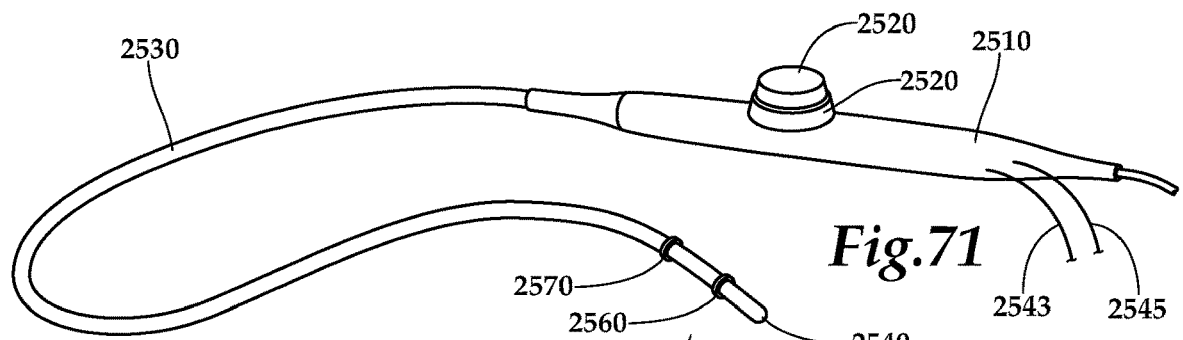
FIG. 71 is a perspective view of an echo probe module for use within a gastric system of a patient and including electrodes thereon for allowing the system to be visualized within (or enhance visualization of) the EP mapping system according to an embodiment of this invention.

In FIG. 71 a gastrointestinal echo probe is disclosed with a control body 2510 at one end with multiple dials 2520 thereon for control thereof, and with a length 2530 extending therefrom to a tip 2540. A distal electrode 2560 and a proximal electrode 2570 are provided near the tip 2540 of the probe 2500 so it can be coupled to an EP mapping system 2002, such as through sensor wires 2543, 2545 coupled to the electrodes 2560, 2570. A location of the tip 2540 can thus be accurately visualized on the display 2004 of the EP mapping system 2002.

Figure 72:
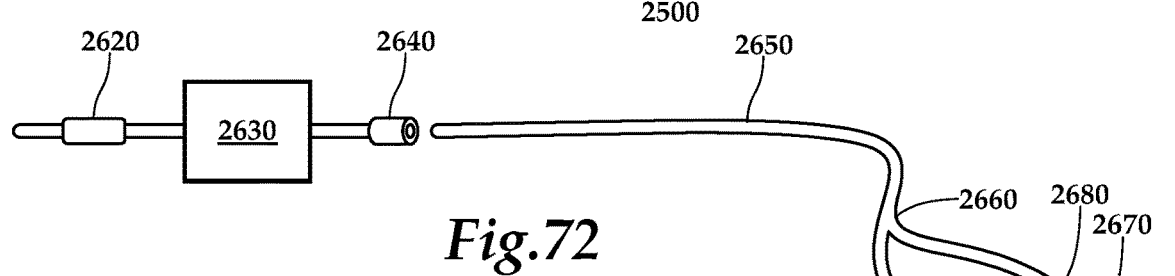
FIG. 72 is a perspective view of one form of cardiac lead wire with electrodes located thereon and configured as a module coupled to an EP mapping system for visualization thereof.

In FIG. 72 a cardiac lead is disclosed which can be coupled to an EP mapping system for visualization on a display 2004 for the EP mapping system 2002. The lead could be for a pacemaker or for an intracardiac defibrillator (ICD) or other similar leads. A connector 2620 allows for coupling to the EP mapping system 2002. Repository 2630 provides data associated with the leads 2600, such as the distance from the electrodes or other sensors thereon to tips 2690 of the leads. A lead proximal end connector 2640 allows for connection to a proximal end of the lead 2600. This connector 2640 is preferably similar to a port on a pacemaker or ICD, so that a proximal end of the lead 2600 can connect to the EP mapping system 2002 the same way that it connects to a pacemaker or ICD. After the lead 2600 has been placed in a desirable location, it can be disconnected at this connector 2640 and connected to the pacemaker or ICD to complete the interventional procedure.

In this embodiment, the lead 2600 includes a split 2660 into two different arms with each arm having a proximal electrode 2680 and a distal electrode 2670. These electrodes 2670, 2680 can be visualized along with the entire lead 2600 on a display for an EP mapping system 2002. Thus, the tips 2690 of the lead 2600 can be placed precisely where desired utilizing the EP mapping system. Once placement of been completed, the proximal end of the lead 2600 can be disconnected from the EP mapping system and connected to a pacemaker or ICD device.

Figure 73:
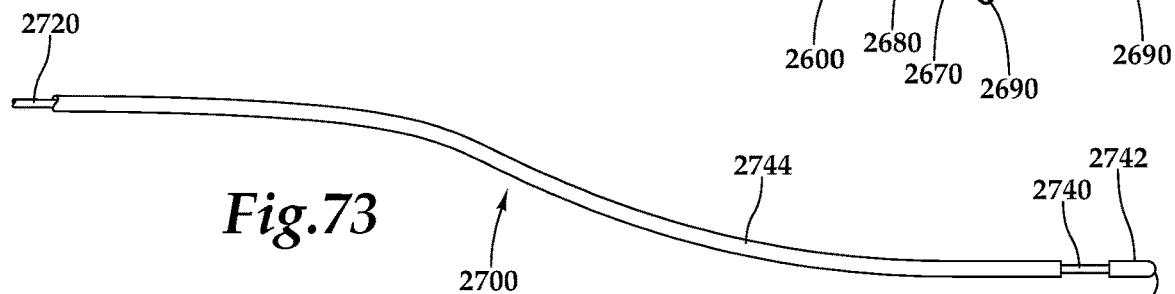
FIG. 73 is a perspective view of a cardiac lead in a simple configuration including at least one electrode and configurable for use of that electrode both as a pacemaker or ICD lead and also for coupling to an EP mapping system for visualization of position of the lead within the EP mapping system.
Figure 74:
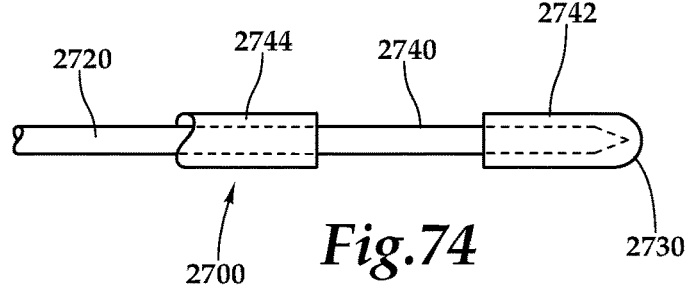
FIG. 74 is a detailed elevation view of a tip of that which is shown in FIG. 73.

In FIG. 73 a simpler lead 2700 is depicted. In this embodiment, a conductor 2720 extends to a tip 2730 and has an insulating jacket with a tip portion 2742 and a body portion 2744 thereon. A gap 2740 in the insulation defines in electrode for this simple lead 2700. In this embodiment, rather than providing separate electrodes for the EP mapping system 2002, the electrode 2740 associated with the lead, and used for pacing or ICD function is first used within the EP mapping system 2002 as an electrode for proper placement of the lead 2700, such as in the form of a unipolar electrode along with a separate body electrode. Thus, the lead 700 can be potentially fitted with no additional electrodes (or just one additional electrode) and still be utilized within an EP mapping system 2002 for placement thereof.

Figure 75:
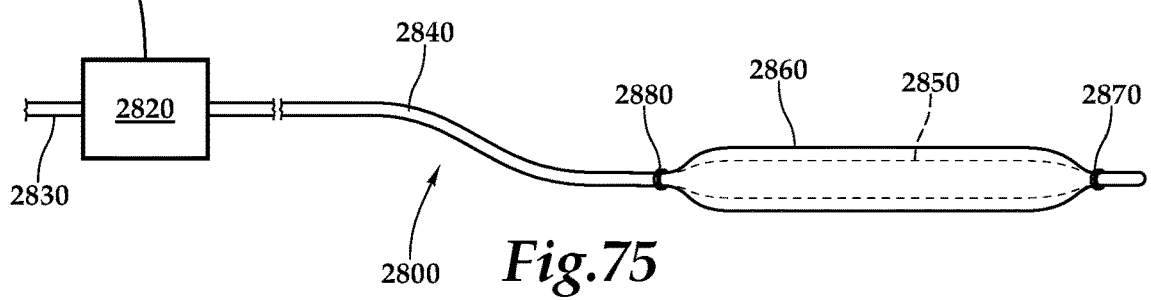
FIG. 75 is a perspective view of an angioplasty balloon including electrodes thereon and configured to be within a module coupleable to an EP mapping system for visualization of the angioplasty balloon within the EP mapping system.

In FIG. 75 an angioplasty balloon module 2800 is depicted. The balloon 2800 includes a connector 2810 and repository 2820 for connecting to an EP mapping system 2002 and for containment of data specific to the angioplasty balloon 2800, such as location of sensors thereon relative to other important reference points on the angioplasty balloon 2800. Line 2830 is also associated therewith which leads to control apparatus for controlling the angioplasty balloon 2800.

An elongate access cannula (or other appropriate structure) 2840 extends to the angioplasty balloon which is depicted with an expanded state 2860 and a collapsed state 2850. Ends of the balloon 2850, 2860 are bounded by a distal electrode 2870 and a proximal electrode 2880. Wires would be routed from these electrodes 2870, 2880 back to the EP mapping system 2002 through the connector 2810. Position of the angioplasty balloon 2800 can thus be identified with the EP mapping system 2002, and once placed where desired, inflation can occur. In addition to angioplasty balloons 2800, other expandable intraluminal devices (e.g. stents) can similarly be fitted with electrodes or other sensors so that their location can be identified during placement and utilization thereof with an EP mapping system 2002.

Figure 76:
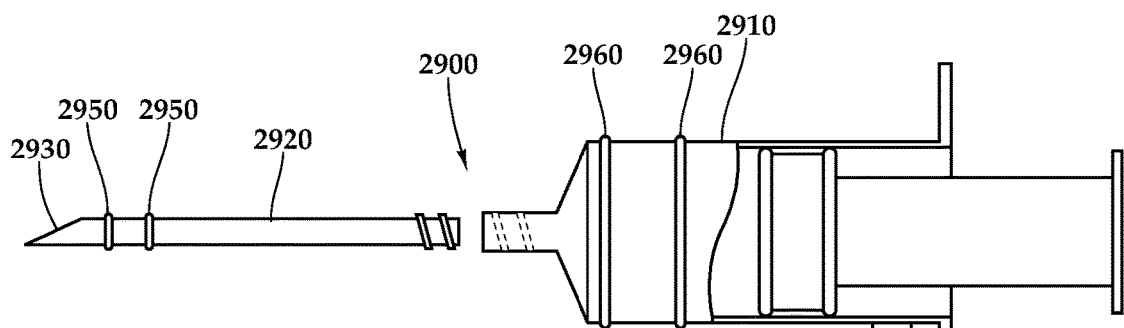
FIG. 76 is a front elevation view of a percutaneous needle coupleable to a syringe and showing how electrodes can be placed on the needle or on the syringe and further be configured within a module coupleable to an EP mapping system for visualization thereon.

In FIG. 76 a percutaneous needle 2900 is shown along with a syringe 2910 and a shaft 2920 removably attachable to the syringe 2910. In this embodiment, a tip 2930 of the needle includes a pair of electrodes 2950 adjacent thereto as one alternative, similar to that depicted in FIGS. 52-56. As an alternative, electrodes 2960 placed upon the syringe can be utilized. The syringe 2910 is coupleable to the EP mapping system 2002 through appropriate connectors, and with a repository including information such as a length of the shaft 2920 of the needle, position of the electrodes 2950, 2960, etc.

Figure 77:
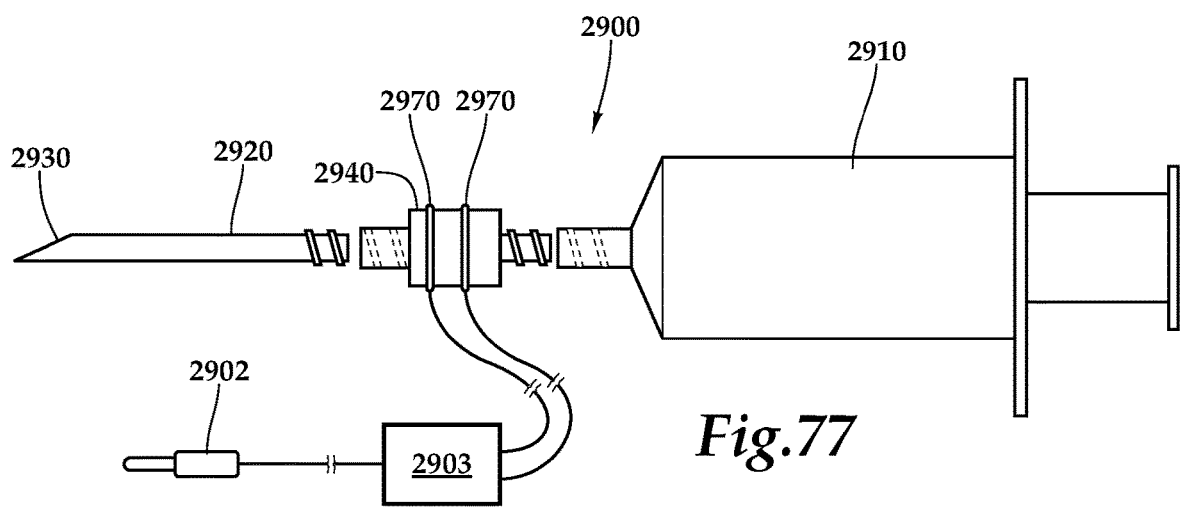
FIG. 77 is a front elevation view of an alternative embodiment of that which is shown in FIG. 76, where an interface between the needle and the syringe is provided with electrodes on this interface and with the interface provided as a module coupleable to an EP mapping system for visualization of the needle coupled to the interface.

In FIG. 77 an interface 2940 is provided between the syringe 2910 and the needle 2920. This interface 2940 includes the electrodes 2970 thereon. The interface includes electrodes 2970, coupled through a repository 2903 to a connector 2902, which can interface with an EP mapping system 2002. Such an interface 2940 allows for utilization of a syringe 2910 and needle 2920 with an EP mapping system, even without any modification to the syringe 2910 or needle 2920, but merely interposing the interface 2940 there between. Standard luer lock fittings are shown for attachment of the syringe 2910 to a needle 2920, but other attachment methodologies could similarly be utilized. Repository 2903 can include data such as how far it is from the interface 2940 to the tip 2930 of the needle 2920, so that the tip 930 the needle 920 can be accurately presented in terms of position and orientation on the display 2004 of the EP mapping system 2002.

Figure 78:
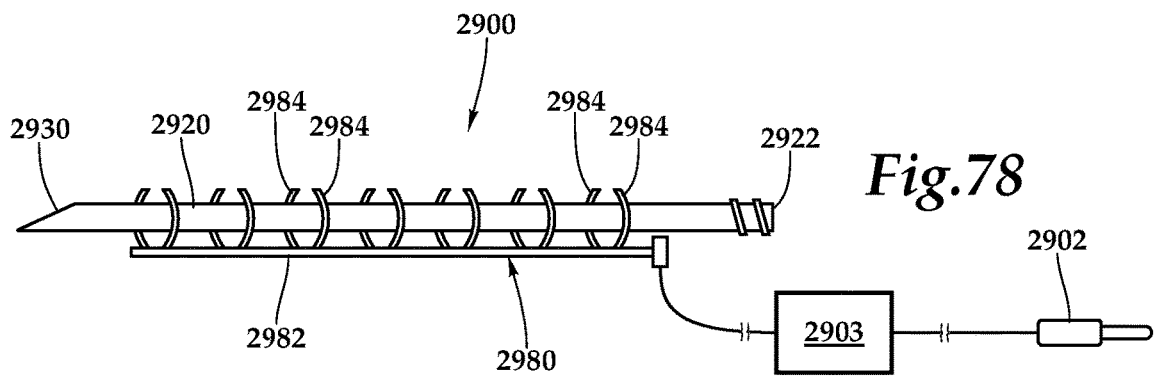
FIG. 78 is a perspective view of a percutaneous needle with an electrode carrying spine removably attachable to the needle depicted thereon, with the spine of electrodes configured within a module coupleable to an EP mapping system for visualization of the needle within the EP mapping system.

In FIG. 78 a needle shaft 2920 is depicted similar to that depicted in FIGS. 76 and 77. Rather than placing electrodes embedded within our formed with the shaft 2920 of the needle 2900, a separate shaft 2982 is provided with prongs 2984 extending therefrom which can snap onto the shaft 2920. This exoskeleton 2980 includes the shaft 2982 supporting these prongs 2984. The shaft 2982 extends back to the repository 2903 and on to a connector 2902. The shaft 2920 can thus have its position and orientation accurately depicted on the display for an EP mapping system 2002 by having this exoskeleton 2980 attached to the shaft 2920 of the needle 2900. Other details of this embodiment are further depicted in FIG. 28 above and related figures for other embodiments. By having this exoskeleton coupled to the EP mapping system through a repository including data about the particular exoskeleton and where it is located upon the shaft 2920 of the needle 2900, the tip 2930 thereof can be accurately represented as to location and orientation upon the display 2004 of the EP mapping system 2002.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A system for visualizing subcutaneous interventional equipment, comprising combination:
    at least one sensor located upon an item of subcutaneous interventional equipment;
    an electrophysiology mapping system including electrodes and a display, said display visualizing subcutaneous patient anatomical structures;
    said at least one sensor coupled to said electrophysiology mapping system to communicate subcutaneous interventional equipment location information and allow said item of subcutaneous interventional equipment to have its position be visualized on said display accurately relative to adjacent patient anatomical structures; and
    wherein said item of subcutaneous interventional equipment includes a repository of item specific information therein which is removably coupled both to the electrophysiology mapping system along with the item of subcutaneous interventional equipment, the information including shape of the item of interventional equipment, size of the item of subcutaneous interventional equipment and location of said at least one sensor upon said item of subcutaneous interventional equipment.

2. The system of claim 1 wherein said at least one sensor on said item of subcutaneous interventional equipment includes a wire extending therefrom and coupled, at least indirectly to the electrophysiology mapping system.

3. The system of claim 1 wherein said at least one sensor is located at a tip of said item of subcutaneous interventional equipment.

4. The system of claim 1 wherein said at least one sensor is located a known distance from said tip of said item of subcutaneous interventional equipment.

5. The system of claim 1 wherein said at least one sensor includes a unipolar electrode, and wherein a separate reference electrode is also associated with said item of subcutaneous interventional equipment.

6. The system of claim 1 wherein said at least one sensor includes a plurality of sensors on said item of subcutaneous interventional equipment, said plurality of sensors including a plurality of electrodes located at known positions upon said item of subcutaneous interventional equipment.

7. The system of claim 1 wherein said at least one sensor includes a plurality of sensors on said item of subcutaneous interventional equipment, said plurality of sensors including a plurality of magnetic field sensors located at known positions upon said item of subcutaneous interventional equipment.

8. The system of claim 1 wherein said item of subcutaneous interventional equipment includes a percutaneous needle extending to a tip and with said at least one sensor located a known distance away from said tip.

9. The system of claim 1 wherein said item of subcutaneous interventional equipment includes a guide wire including said at least one sensor at a known position upon said guide wire for accurate placement of said guide wire within an image visualized upon said display of said electrophysiology mapping system.

10. The system of claim 1 wherein said item of subcutaneous interventional equipment includes a vascular catheter with said at least one sensor located at a known position upon said vascular catheter for accurate placement of said vascular catheter within an image visualized upon said display of said electrophysiology mapping system.

11. The system of claim 1 wherein said item of subcutaneous interventional equipment includes an angioplasty balloon with said at least one sensor located a known position upon said angioplasty balloon for accurate placement of said angioplasty balloon within an image visualized upon said display of said electrophysiology mapping system.

12. A method for visualizing an item of subcutaneous interventional equipment, including steps of:

removably connecting at least one sensor located upon the item of subcutaneous interventional equipment to an electrophysiology mapping system, the electrophysiology mapping system including electrodes and a display for visualization of patient anatomical structures in a subcutaneous space; and said connecting step including communicating to the electrophysiology mapping system from a repository of item specific information, details of the item of subcutaneous interventional equipment including shape of the item of subcutaneous interventional equipment and location of said at least one sensor upon said subcutaneous interventional equipment, for accurate placement of said subcutaneous interventional equipment upon an image visualized on said display of said electrophysiology mapping system.

13. The method of claim 12 wherein said connecting step includes connecting a plurality of sensors to said item of subcutaneous interventional equipment; and wherein said connecting step includes communicating information from each of said sensors to said electrophysiology mapping system for accurate orientation of the item of subcutaneous interventional equipment within an image presented on the display of the electrophysiology mapping system.

14. A system for visualizing subcutaneous interventional equipment, comprising combination:

at least one sensor located upon an item of subcutaneous interventional equipment;

an electrophysiology mapping system including electrodes and a display, said display visualizing subcutaneous patient anatomical structures;

said at least one sensor coupled to said electrophysiology mapping system to communicate subcutaneous interventional equipment location information and allow said item of subcutaneous interventional equipment to have its position be visualized on said display accurately relative to adjacent patient anatomical structures; and wherein said item of subcutaneous interventional equipment includes a repository of items specific information therein which is removably coupled to the electrophysiology mapping system along with the item of subcutaneous interventional equipment, the information including at least one detail taken from a group of details including a shape of the item of interventional equipment, a size of the item of interventional equipment, and a location of said at least one sensor upon said item of subcutaneous interventional equipment.

* * * * *